United States Patent
Nikoozadeh et al.

(10) Patent No.: US 11,531,096 B2
(45) Date of Patent: *Dec. 20, 2022

(54) HIGH PERFORMANCE HANDHELD ULTRASOUND

(71) Applicant: VAVE HEALTH, INC., Redwood City, CA (US)

(72) Inventors: Amin Nikoozadeh, San Carlos, CA (US); Jung Woo Choe, Redwood City, CA (US); Stefan Craciun, San Carlos, CA (US)

(73) Assignee: VAVE HEALTH, INC., Redwood City, CA (US)

( * ) Notice: Subject to any disclaimer, the term of this patent is extended or adjusted under 35 U.S.C. 154(b) by 708 days.

This patent is subject to a terminal disclaimer.

(21) Appl. No.: 16/494,731

(22) PCT Filed: Mar. 23, 2018

(86) PCT No.: PCT/US2018/024059
§ 371 (c)(1),
(2) Date: Sep. 16, 2019

(87) PCT Pub. No.: WO2018/175905
PCT Pub. Date: Sep. 27, 2018

(65) Prior Publication Data
US 2021/0405172 A1 Dec. 30, 2021

Related U.S. Application Data

(63) Continuation-in-part of application No. 15/470,798, filed on Mar. 27, 2017, which is a
(Continued)

(51) Int. Cl.
*G01S 7/52* (2006.01)
*A61B 8/08* (2006.01)
(Continued)

(52) U.S. Cl.
CPC .......... *G01S 7/5208* (2013.01); *A61B 8/4444* (2013.01); *A61B 8/4494* (2013.01);
(Continued)

(58) Field of Classification Search
None
See application file for complete search history.

(56) References Cited

U.S. PATENT DOCUMENTS

| 839,442 A | 12/1906 | Jesse |
| 4,413,629 A | 11/1983 | Durley, III |

(Continued)

FOREIGN PATENT DOCUMENTS

| CN | 1231835 A | 10/1999 |
| CN | 102525557 A | 7/2012 |

(Continued)

OTHER PUBLICATIONS

European Application No. 18771485.2 Search Report dated Nov. 23, 2020.
(Continued)

*Primary Examiner* — Katherine L Fernandez
(74) *Attorney, Agent, or Firm* — Wilson Sonsini Goodrich & Rosati

(57) ABSTRACT

A handheld ultrasound device may comprise components configured to provide decreased size, weight, complexity, and power consumption. The handheld ultrasound device may comprise a beamformer configured to implement and compress a flag table in place of a delay table. These improvements can decrease the amount of memory used to generate ultrasound images, which can decrease the size, weight, and power consumption of the handheld ultrasound device. Ultrasound image data on a handheld imaging probe can be compressed on the handheld imaging probe prior to transmission from the probe in order to decrease the amount
(Continued)

of data transmitted from the probe. The compressed data may comprise compressed pixels to maintain spatial image resolution. The compression circuitry may comprise an amount of memory related to a dynamic range of the compressed data that is independent of the dynamic range of the input data, which can decrease memory, power consumption, and latencies.

23 Claims, 20 Drawing Sheets

Related U.S. Application Data continuation-in-part of application No. 15/470,793, filed on Mar. 27, 2017, now Pat. No. 10,469,846, which is a continuation-in-part of application No. 15/470,700, filed on Mar. 27, 2017, now Pat. No. 10,856,843, which is a continuation-in-part of application No. 15/467,656, filed on Mar. 23, 2017, now abandoned, said application No. 15/470,700 is a continuation-in-part of application No. 15/467,656, filed on Mar. 23, 2017, now abandoned.

(51) Int. Cl.
*A61B 8/00* (2006.01)
*G06T 9/00* (2006.01)
*G01S 15/89* (2006.01)
*G16H 30/40* (2018.01)
*G06T 7/00* (2017.01)
*G06V 10/25* (2022.01)

(52) U.S. Cl.
CPC ........ *A61B 8/5207* (2013.01); *G01S 15/8915* (2013.01); *G06T 7/0012* (2013.01); *G06T 9/00* (2013.01); *G06V 10/25* (2022.01); *G16H 30/40* (2018.01); *G06T 2207/10132* (2013.01)

(56) References Cited

U.S. PATENT DOCUMENTS

| | | |
|---|---|---|
| 4,589,284 A | 5/1986 | Breimesser et al. |
| 5,396,890 A | 3/1995 | Weng |
| 5,590,658 A | 1/1997 | Chiang et al. |
| 5,603,323 A | 2/1997 | Pflugrath et al. |
| 5,640,960 A | 6/1997 | Jones et al. |
| 5,778,177 A | 7/1998 | Azar |
| 5,795,297 A | 8/1998 | Daigle |
| 5,817,024 A | 10/1998 | Ogle et al. |
| 5,845,004 A | 12/1998 | Banjanin et al. |
| 5,851,186 A | 12/1998 | Wood et al. |
| 5,865,749 A | 2/1999 | Doten et al. |
| 5,891,030 A | 4/1999 | Johnson et al. |
| 5,944,659 A | 8/1999 | Flach et al. |
| 5,964,709 A | 10/1999 | Chiang et al. |
| 5,983,123 A | 11/1999 | Shmulewitz |
| 6,117,085 A | 9/2000 | Picatti et al. |
| 6,135,961 A | 10/2000 | Pflugrath et al. |
| 6,142,946 A | 11/2000 | Hwang et al. |
| 6,241,673 B1 | 6/2001 | Williams |
| 6,248,072 B1 | 6/2001 | Murkin |
| 6,248,073 B1 | 6/2001 | Gilbert et al. |
| 6,306,089 B1 | 10/2001 | Coleman et al. |
| 6,368,279 B1 | 4/2002 | Liu |
| 6,436,040 B1 | 8/2002 | Collamore et al. |
| 6,440,071 B1 | 8/2002 | Slayton et al. |
| 6,440,072 B1 | 8/2002 | Schuman et al. |
| 6,464,636 B1 | 10/2002 | Kinicki et al. |
| 6,471,651 B1 | 10/2002 | Hwang et al. |
| 6,530,887 B1 | 3/2003 | Gilbert et al. |
| 6,592,521 B1 | 7/2003 | Urbano et al. |
| 6,669,633 B2 | 12/2003 | Brodsky et al. |
| 6,755,789 B2 | 6/2004 | Stringer et al. |
| 6,780,154 B2 | 8/2004 | Hunt et al. |
| 6,783,493 B2 | 8/2004 | Chiang et al. |
| 6,969,352 B2 | 11/2005 | Chiang et al. |
| 7,022,075 B2 | 4/2006 | Grunwald et al. |
| 7,115,093 B2 | 10/2006 | Halmann et al. |
| 7,141,020 B2 | 11/2006 | Poland et al. |
| 7,199,738 B2 | 4/2007 | Han et al. |
| 7,223,242 B2 | 5/2007 | He et al. |
| 7,257,379 B2 | 8/2007 | Ozluturk et al. |
| 7,294,106 B2 | 11/2007 | Birkenbach et al. |
| 7,371,218 B2 | 5/2008 | Walston et al. |
| 7,394,410 B1 | 7/2008 | Wegener |
| 7,458,935 B2 | 12/2008 | Cerofolini |
| 7,729,742 B2 | 6/2010 | Govari |
| 7,833,159 B2 | 11/2010 | Ahn et al. |
| D629,113 S | 12/2010 | Wodecki |
| 7,867,168 B2 | 1/2011 | Little et al. |
| 7,891,230 B2 | 2/2011 | Randall |
| D639,434 S | 6/2011 | Wodecki et al. |
| 7,984,651 B2 | 7/2011 | Randall et al. |
| 7,987,303 B2 | 7/2011 | Bartlett |
| 8,043,221 B2 | 10/2011 | Marteau et al. |
| 8,066,642 B1 | 11/2011 | Little et al. |
| 8,079,263 B2 | 12/2011 | Randall et al. |
| 8,488,013 B2 | 7/2013 | Jia et al. |
| 8,500,645 B2 | 8/2013 | Cohen et al. |
| 8,535,227 B2 | 9/2013 | Halmann et al. |
| 8,551,000 B2 | 10/2013 | Chiang et al. |
| 8,628,474 B2 | 1/2014 | Chiang et al. |
| 8,717,843 B2 | 5/2014 | Cerofolini |
| 8,852,103 B2 | 10/2014 | Rothberg et al. |
| 9,022,936 B2 | 5/2015 | Rothberg et al. |
| 9,028,412 B2 | 5/2015 | Rothberg et al. |
| 9,033,879 B2 | 5/2015 | Urness et al. |
| 9,033,884 B2 | 5/2015 | Rothberg et al. |
| 9,061,318 B2 | 6/2015 | Rothberg et al. |
| 9,067,779 B1 | 6/2015 | Rothberg et al. |
| 9,149,255 B2 | 10/2015 | Rothberg et al. |
| 9,151,832 B2 | 10/2015 | Little et al. |
| 9,155,521 B2 | 10/2015 | Rothberg et al. |
| 9,198,637 B2 | 12/2015 | Rothberg et al. |
| 9,229,097 B2 | 1/2016 | Rothberg et al. |
| 9,242,275 B2 | 1/2016 | Rothberg et al. |
| 9,247,924 B2 | 2/2016 | Rothberg et al. |
| 9,268,014 B2 | 2/2016 | Rothberg et al. |
| 9,268,015 B2 | 2/2016 | Rothberg et al. |
| 9,290,375 B2 | 3/2016 | Rothberg et al. |
| 9,327,142 B2 | 5/2016 | Rothberg et al. |
| 9,337,901 B2 | 5/2016 | Takahashi |
| 9,339,253 B2 | 5/2016 | Peszynski et al. |
| 9,351,706 B2 | 5/2016 | Rothberg et al. |
| 9,383,435 B2 | 7/2016 | Osawa |
| 9,392,996 B2 | 7/2016 | Chamberlain et al. |
| 9,394,162 B2 | 7/2016 | Rothberg et al. |
| 9,402,601 B1 | 8/2016 | Berger et al. |
| 9,476,969 B2 | 10/2016 | Rothberg et al. |
| 10,469,846 B2 | 11/2019 | Choe et al. |
| 10,681,357 B2 | 6/2020 | Choe et al. |
| 10,856,843 B2 * | 12/2020 | Choe .................. G01S 15/8915 |
| 2002/0110196 A1 | 8/2002 | Nguyen et al. |
| 2002/0195910 A1 | 12/2002 | Hus et al. |
| 2002/0196465 A1 | 12/2002 | Ohta |
| 2003/0078501 A1 | 4/2003 | Barnes et al. |
| 2003/0080747 A1 | 5/2003 | Huelss |
| 2003/0097071 A1 | 5/2003 | Halmann et al. |
| 2003/0139664 A1 | 7/2003 | Hunt et al. |
| 2003/0139671 A1 | 7/2003 | Walston et al. |
| 2003/0167004 A1 | 9/2003 | Dines et al. |
| 2003/0181811 A1 | 9/2003 | Amemiya et al. |
| 2003/0187353 A1 | 10/2003 | Ng et al. |
| 2004/0015079 A1 | 1/2004 | Berger et al. |
| 2004/0140965 A1 | 7/2004 | Wang et al. |
| 2004/0225220 A1 | 11/2004 | Rich |
| 2006/0010296 A1 | 1/2006 | Dent |
| 2006/0058655 A1 | 3/2006 | Little |
| 2006/0072799 A1 | 4/2006 | McLain |
| 2006/0184042 A1 | 8/2006 | Wang et al. |
| 2007/0016023 A1 | 1/2007 | Phelps et al. |

(56) References Cited

U.S. PATENT DOCUMENTS

| | | |
|---|---|---|
| 2007/0242567 A1 | 10/2007 | Daft et al. |
| 2008/0114247 A1 | 5/2008 | Urbano et al. |
| 2008/0114248 A1 | 5/2008 | Urbano et al. |
| 2008/0114255 A1 | 5/2008 | Schwartz et al. |
| 2008/0137482 A1 | 6/2008 | Kang et al. |
| 2008/0208061 A1 | 8/2008 | Halmann |
| 2008/0214938 A1 | 9/2008 | Solomon et al. |
| 2008/0242992 A1 | 10/2008 | Criton |
| 2008/0262347 A1 | 10/2008 | Batchelder et al. |
| 2009/0177086 A1 | 7/2009 | Steen |
| 2010/0022822 A1 | 1/2010 | Walshe et al. |
| 2010/0022882 A1 | 1/2010 | Duckworth et al. |
| 2010/0027857 A1 | 2/2010 | Wang |
| 2010/0056956 A1 | 3/2010 | Dufresne et al. |
| 2010/0160786 A1 | 6/2010 | Nordgren et al. |
| 2010/0168576 A1 | 7/2010 | Poland et al. |
| 2010/0249596 A1* | 9/2010 | Magee ............... G10K 11/346 367/121 |
| 2010/0268042 A1 | 10/2010 | Wang et al. |
| 2010/0277305 A1 | 11/2010 | Garner et al. |
| 2010/0280315 A1 | 11/2010 | Pan |
| 2010/0280419 A1 | 11/2010 | Donskoy et al. |
| 2010/0305449 A1 | 12/2010 | Wegener et al. |
| 2011/0071397 A1 | 3/2011 | Wodnicki et al. |
| 2011/0245670 A1 | 10/2011 | Tashiro et al. |
| 2011/0286630 A1 | 11/2011 | Harder et al. |
| 2012/0013758 A1 | 1/2012 | Frederiksen et al. |
| 2012/0022379 A1 | 1/2012 | Gubbini et al. |
| 2012/0108975 A1 | 5/2012 | Marteau et al. |
| 2012/0265027 A1 | 10/2012 | Lee et al. |
| 2012/0289836 A1 | 11/2012 | Ukimura et al. |
| 2013/0023767 A1 | 1/2013 | Mammone |
| 2013/0165796 A1 | 6/2013 | Tashiro |
| 2013/0184587 A1 | 7/2013 | Eom et al. |
| 2013/0226001 A1 | 8/2013 | Steen et al. |
| 2013/0261463 A1 | 10/2013 | Chiang et al. |
| 2013/0338498 A1 | 12/2013 | Emelianov et al. |
| 2013/0345566 A1 | 12/2013 | Weitzel et al. |
| 2014/0005547 A1 | 1/2014 | Balasubramanian |
| 2014/0024942 A1 | 1/2014 | Halmann et al. |
| 2014/0028479 A1 | 1/2014 | Cheung |
| 2014/0051984 A1 | 2/2014 | Berger et al. |
| 2014/0114190 A1 | 4/2014 | Chiang et al. |
| 2014/0121524 A1 | 5/2014 | Chiang et al. |
| 2014/0180097 A1 | 6/2014 | Rothberg et al. |
| 2014/0180100 A1 | 6/2014 | Rothberg et al. |
| 2014/0243614 A1 | 8/2014 | Rothberg et al. |
| 2014/0243669 A1 | 8/2014 | Halmann et al. |
| 2014/0275851 A1 | 9/2014 | Amble et al. |
| 2014/0288428 A1 | 9/2014 | Rothberg et al. |
| 2014/0300720 A1 | 10/2014 | Rothberg et al. |
| 2014/0357993 A1 | 12/2014 | Hiriyannaiah et al. |
| 2015/0032002 A1 | 1/2015 | Rothberg et al. |
| 2015/0038844 A1 | 2/2015 | Blalock et al. |
| 2015/0067441 A1 | 3/2015 | Gorissen et al. |
| 2015/0087987 A1 | 3/2015 | Ryu et al. |
| 2015/0092838 A1 | 4/2015 | Hiriyannaiah et al. |
| 2015/0160120 A1 | 6/2015 | Sun et al. |
| 2015/0164477 A1 | 6/2015 | Ryu et al. |
| 2015/0208901 A1 | 7/2015 | Gazdzinski |
| 2015/0216509 A1 | 8/2015 | Yamagata et al. |
| 2015/0245823 A1 | 9/2015 | Jin et al. |
| 2015/0247921 A1 | 9/2015 | Rothberg et al. |
| 2015/0250454 A1 | 9/2015 | Lee |
| 2015/0297192 A1 | 10/2015 | Chamberlain et al. |
| 2015/0297193 A1 | 10/2015 | Rothberg et al. |
| 2015/0325036 A1 | 11/2015 | Lee |
| 2015/0326872 A1 | 11/2015 | Lee et al. |
| 2015/0366538 A1 | 12/2015 | McKenna |
| 2015/0381995 A1 | 12/2015 | Han et al. |
| 2016/0007957 A1 | 1/2016 | Murphy et al. |
| 2016/0008556 A1 | 1/2016 | Baym et al. |
| 2016/0009544 A1 | 1/2016 | Rothberg et al. |
| 2016/0015368 A1 | 1/2016 | Poland |
| 2016/0069989 A1 | 3/2016 | Rothberg et al. |
| 2016/0100824 A1 | 4/2016 | Kim |
| 2016/0120507 A1 | 5/2016 | Ninomiya et al. |
| 2016/0125641 A1 | 5/2016 | Lee et al. |
| 2016/0131748 A1 | 5/2016 | Little et al. |
| 2016/0151045 A1 | 6/2016 | Pelissier et al. |
| 2016/0199036 A1 | 7/2016 | Pelissier et al. |
| 2016/0202349 A1 | 7/2016 | Rothberg et al. |
| 2016/0207760 A1 | 7/2016 | Rothberg et al. |
| 2016/0228091 A1 | 8/2016 | Chiang et al. |
| 2016/0228092 A1 | 8/2016 | Kim et al. |
| 2016/0280538 A1 | 9/2016 | Rothberg et al. |
| 2016/0290969 A1 | 10/2016 | Rothberg et al. |
| 2016/0290970 A1 | 10/2016 | Rothberg et al. |
| 2016/0338676 A1 | 11/2016 | Berger et al. |
| 2016/0345936 A1 | 12/2016 | Cho et al. |
| 2016/0377717 A1 | 12/2016 | Srinivasan et al. |
| 2017/0000457 A1 | 1/2017 | Chamberlain et al. |
| 2017/0027547 A1 | 2/2017 | Haugaard et al. |
| 2017/0029271 A1 | 2/2017 | Rothberg et al. |
| 2017/0067988 A1 | 3/2017 | Rothberg et al. |
| 2017/0143313 A1 | 5/2017 | Pelissier et al. |
| 2017/0238907 A1 | 8/2017 | Kommu Chs |
| 2018/0008233 A1 | 1/2018 | Pelissier et al. |
| 2018/0271482 A1 | 9/2018 | Choe et al. |
| 2018/0271483 A1 | 9/2018 | Nikoozadeh et al. |
| 2021/0113186 A1 | 4/2021 | Choe et al. |

FOREIGN PATENT DOCUMENTS

| | | |
|---|---|---|
| CN | 103284735 A | 9/2013 |
| EP | 2135110 A2 | 12/2009 |
| EP | 2863805 A1 | 4/2015 |
| JP | S5215372 A | 2/1977 |
| JP | 2002530142 A | 9/2002 |
| JP | 2003033350 A | 2/2003 |
| JP | 2012120691 A | 6/2012 |
| JP | 2013158589 A | 8/2013 |
| WO | WO-9701768 A2 | 1/1997 |
| WO | WO-0030540 A1 | 6/2000 |
| WO | WO-0066001 A1 | 11/2000 |
| WO | WO-0079300 A1 | 12/2000 |
| WO | WO-03069761 A1 | 8/2003 |
| WO | WO-2008124841 A2 | 10/2008 |
| WO | WO-2008146201 A2 | 12/2008 |
| WO | WO-2009135255 A1 | 11/2009 |
| WO | WO-2013148730 A2 | 10/2013 |
| WO | WO-2013162244 A1 | 10/2013 |
| WO | WO-2014003404 A1 | 1/2014 |
| WO | WO-2014123922 A1 | 8/2014 |
| WO | WO-2014134175 A2 | 9/2014 |
| WO | WO-2014151362 A2 | 9/2014 |
| WO | WO-2014151525 A2 | 9/2014 |
| WO | WO-2014165662 A2 | 10/2014 |
| WO | WO-2015013245 A2 | 1/2015 |
| WO | WO-2015048327 A2 | 4/2015 |
| WO | WO-2015161147 A1 | 10/2015 |
| WO | WO-2015161157 A1 | 10/2015 |
| WO | WO-2015161164 A1 | 10/2015 |
| WO | WO-2015161292 A1 | 10/2015 |
| WO | WO-2016011000 A1 | 1/2016 |
| WO | WO-2016052817 A1 | 4/2016 |
| WO | WO-2016057622 A1 | 4/2016 |
| WO | WO-2016057631 A1 | 4/2016 |
| WO | WO-2017013443 A1 | 1/2017 |

OTHER PUBLICATIONS

U.S. Appl. No. 15/470,798 Final Office Action dated Mar. 3, 2021.

U.S. Appl. No. 15/470,798 Non-Final Office Action dated Nov. 17, 2020.

U.S. Appl. No. 15/470,700 Non-Final Office Action dated May 1, 2020.

U.S. Appl. No. 16/576,288 Non-Final Office Action dated Jan. 17, 2020.

Ahn, et al. A new wireless hand-held ultrasound system with smartphone, tablet for mobile healthcare. 2015 IEEE International Ultrasonics Symposium Proceedings.

(56) References Cited

OTHER PUBLICATIONS

Ahn, et al. Smartphone-based portable ultrasound imaging system: Prototype implementation and evaluation. Conference: Oct. 2015 IEEE International Ultrasonics Symposium (IUS). DOI: 10.1109/ULTSYM.2015.0517.

Almekkawy, et al. An optimized ultrasound digital beamformer with dynamic focusing implemented on FPGA. Conf Proc IEEE Eng Med Biol Soc. 2014;2014:3296-9. doi: 10.1109/EMBC.2014.6944327.

Daft, et al. Matrix Transducer Design with Improved Image Quality and Acquisition Rate. Conference: Ultrasonics Symposium, Nov. 2007, IEEE. DOI: 10.1109/ULTSYM.2007.112.

Fuller, et al. Real time imaging with the Sonic Window: A pocket-sized, C-scan, medical ultrasound device. Conference: Ultrasonics Symposium (IUS), Oct. 2009 IEEE International. DOI: 10.1109/ULTSYM.2009.5441943.

Hewener, et al. Mobile ultrafast ultrasound imaging system based on smartphone and tablet devices. Ultrasonics Symposium (IUS), Oct. 2015 IEEE International.

Hoegh, et al. Ultrasonic Tomography for Evaluation of Concrete Pavements. Transportation Research Record: Journal of the Transportation Research Board. 2011. vol. 2232. DOI: 10.3141/2232-09.

Hwang, et al. Portable ultrasound device for battlefield trauma. Conference: Ultrasonics Symposium, 1998. Proceedings, Feb. 1998 IEEE, vol. 2. DOI: 10.1109/ULTSYM.1998.765266.

Kim, et al. A new nonlinear zone-based beamforming method for point-of-care ultrasound: Algorithms and implementation. 2014 IEEE International Ultrasonics Symposium pp. 2137-2140.

Kim, et al. A single FPGA-based portable ultrasound imaging system for point-of-care applications. IEEE Trans Ultrason Ferroelectr Freq Control. Jul. 2012;59(7):1386-94. doi: 10.1109/TUFFC.2012.2339.

Nippon Pulse America, Inc. S040 Linear Shaft Motor for Small-Scale High Precision. Web article. Aug. 9, 2011. URL:<http://www.nipponpulse.com/news/view/s040-linear-shaft-motor-for-small-scale-high-precision>.

PCT/US2018/024059 International Patent Report on Patentability dated Oct. 3, 2019.

PCT/US2018/024059 International Search Report and Written Opinion dated Aug. 9, 2018.

Ruiter, et al. First results of a clinical study with 3D ultrasound computer tomography. Ultrasonics Symposium (IUS), 2013 IEEE International.

Yang, et al. A Comparison of the Lookup Table and On-The-Fly Calculation Methods for the Beamforming Control Unit. ITC-CSCC : 2008, Jul. 2008, 657-660 (4 pages).

Co-Pending U.S. Appl. No. 16/576,288, filed Sep. 19, 2019.

\* cited by examiner

| Region of Interest | ··· 610 | 611 | 612 | 613 | 614 ··· |
|---|---|---|---|---|---|
| Memory Contents (Delay Times) | ··· 4700 | 4708 | 4716 | 4724 | 4732 ··· |

800

810

HIGH PERFORMANCE HANDHELD ULTRASOUND

This application claims priority to U.S. patent application Ser. No. 15/467,656, filed Mar. 23, 2017; U.S. patent application Ser. No. 15/470,700, filed Mar. 27, 2017; U.S. patent application Ser. No. 15/470,793, filed Mar. 27, 2017; and U.S. patent application Ser. No. 15/470,798, filed Mar. 27, 2017, each of which is incorporated herein by reference in its entirety for all purposes.

BACKGROUND

Ultrasound imaging is commonly used as a non-invasive, diagnostic imaging modality that provides images of the internal volumes of objects in many different fields such as medical diagnostics and non-destructive materials testing. For instance, ultrasound imaging can be used to provide images of internal organs, such as an abdomen or a heart. One limitation in developing handheld ultrasound imaging devices without sacrificing image quality may be the requirement of processing large amounts of data that consumes a substantial amount of computational resources. This reliance on substantial computational resources and implications of such resources on the device size and power requirements may limit the development of handheld ultrasound devices that are capable of producing images having the quality offered by conventional (e.g., non-handheld) ultrasound systems.

In light of the above, it would be advantageous to provide a handheld ultrasound system and method that requires or consumes fewer computational resources without sacrificing image quality. Ideally, such systems may be compact, handheld, and utilizable by individuals with no special technical training while still producing images of the same or comparable quality to those produced by conventional or non-handheld ultrasound systems.

In addition, prior methods and apparatus to compress data such as ultrasound image data can be less than ideal in at least some respects. For example, compression of image data with formats such as JPEG and MPEG can result in decreased image quality in at least some instances. Also, prior methods and apparatus for compressing data can result in greater amounts of circuitry and power consumption than would be ideal. For example, prior approaches to compressing data with lookup tables can result in greater amounts of memory being used, increased power consumption, and may have longer latency periods than would be ideal.

Therefore, improved methods and apparatus for compressing data such as ultrasound data would be helpful. Ideally, such improved methods and apparatus would provide increased throughput, decreased power consumption, decreased latency, and decreased degradation of images.

In addition, prior methods and apparatus to generate ultrasound image data with a handheld imaging system can be less than ideal in at least some respects. The prior handheld ultrasound imaging systems may have less than ideal image resolution, which can decrease clinical utility. For example, small image detail which can be relevant to the diagnosis and treatment of patients may not be present in images of at least some of the prior ultrasound systems with handheld probes. The prior ultrasound imaging systems may have greater complexity than would be ideal, which can increase the cost, weight, power consumption, and size of a handheld ultrasound probe. With real-time ultrasound imaging, latencies can result in a less than ideal performance. For example, a user may often align the probe with a target tissue and delays in showing images on the display can make alignment of the probe with a moving target tissue more difficult than would be ideal. For other real-time applications such as robotic surgery and telemedicine, latencies in generating images can also result in less than ideal system performance and the decrease responsiveness of the system. The amount of bandwidth required to reliably transmit data wirelessly with prior systems can be greater than would be ideal, which can result in additional degradation and latencies of transmitted ultrasound data. Prior handheld imaging systems can weigh more than would be ideal.

Therefore, improved methods and apparatus for generating ultrasound images with a handheld ultrasound imaging system would be helpful. Ideally, such improved methods and apparatus would provide ultrasound images with increased image resolution and faster data transmission with decreased data size for each image, decreased latencies, complexity, power consumption, and probe weight.

SUMMARY

The systems, devices, and methods disclosed herein may be capable of producing high-resolution ultrasound images with a handheld ultrasound system with decreased computational requirements. Although specific reference is made to a handheld imaging probe for medical applications, the ultrasound system and methods disclosed herein may find application in many fields, such as non-destructive testing, metrology, materials science, aerospace, transportation infrastructure, dermatology, and dentistry.

The handheld ultrasound device may comprise a plurality of components configured to provide decreased size, weight, complexity, and power consumption. The handheld ultrasound device may comprise an ultrasound transducer and an analog to digital ("A/D") converter coupled to the ultrasound transducer. A processor comprising a beamformer can be coupled to the A/D converter and configured to selectively store a plurality of signals from the A/D converter in a memory of the processor. The selective storage of the plurality of samples from the A/D converter can decrease the amount of memory used to generate ultrasound images, which can decrease the size, weight and power consumption of the handheld ultrasound device.

The handheld ultrasound imaging device can be configured for ease of use, and may comprise wireless communication circuitry to transmit images for display. In some instances, the handheld ultrasound device is configured to be held in the hand of a user, and may be configured to allow a person to measure himself or herself. The handheld ultrasound system comprises a housing to contain the measurement components, and the housing is sized, in some instances, such that the user can readily grasp the housing and lift the measurement components within the housing. The compactness and decreased mass of the handheld ultrasound system allow the system to be easily held in the hand and transported. The handheld ultrasound system may comprise a maximum dimension across within a range from about 80 mm to about 200 mm.

In an aspect, an ultrasound device to image an object comprises a processor coupled to the ultrasound transducer. The processor may comprise a tangible medium configured with instructions that when executed cause the processor to selectively store individual samples from an analog-to-digital (A/D) converter. Each of the selected individual samples may correspond to an ultrasound signal from a location in the object and an associated delay time for the ultrasound signal to reach the transducer from the location in the object. The delay time may correspond to a round-trip time of flight to the transducer. A maximum delay error may comprise no more than half of an RF sampling period. Each of the selected individual samples may be selectively stored in a memory of the processor in accordance with a flag table. The A/D converter may be configured to output a plurality of samples and wherein the selected individual samples comprise no more than about 70% of the plurality of samples and optionally no more than about 60%. The plurality of samples from the A/D converter may comprise a plurality of unselected samples. The plurality of unselected samples may be discarded prior to receipt of a last sample from the A/D converter. The delay time may correspond to a round-trip time of flight of the ultrasound signal from the transducer to the location and from the location to the transducer. The ultrasound device may comprise a plurality of transducers. There may be a delay time to said each of the plurality of transducers. The delay time may correspond to a round-trip time of flight to said each of the plurality of ultrasound transducers. For each location in the object there may be a delay time associated with the receipt of the ultrasound signal by the transducer. The sample corresponding to the ultrasound signal received at the transducer may be selected in accordance with a delay time for the transducer. The processor may not comprise a radiofrequency (RF) buffer to store a plurality of samples from the A/D converter. Each of the selectively stored individual samples from the A/D converter may be selected for use with a pixel in no more than one sampling cycle of the A/D converter after being received by the processor. An RF sample from the A/D converter may be selected to be used for a certain pixel or not, in no more than one RF sampling clock cycle after the RF sample is captured. The processor may be configured to generate an image from the selected samples. The processor may comprise a beamformer that utilizes a power draw of no more than 100 mW to generate the image. The ultrasound transducer may comprise a one-dimensional array of ultrasound transducers. The ultrasound transducer may comprise a two-dimensional array of ultrasound transducers. The ultrasound transducer may comprise a plurality of transducers. The plurality of transducers may comprise a number of transducers selected from the group consisting of 64 transducers, 128 transducers, and 256 transducers. The plurality of ultrasound transducers may comprise a number of transducers within a range of 32 transducers to 256 transducers.

In another aspect, an ultrasound device to generate an image of an object may comprise a plurality of transducer elements, a front-end unit, a real-time beamformer, and an image processor. Each transducer element may be associated with a data channel. Each data channel may comprise a transducer that receives ultrasonic energy reflected by the region of interest and generates radio frequency (RF) signals based on the received reflected ultrasonic energy. The front-end unit may amplify and digitize the RF signals received from each data channel to provide RF samples at an RF sampling rate associated with a data clock having a clock cycle. An RF sample may be received by each data channel at each clock cycle corresponding to the RF sampling rate. Each RF sample may be associated with one location in the scanline defined by a trajectory of the beam through the location of interest. The real-time beamformer may have a transmit beamformer and a flag table based receive beamformer. The transmit beamformer may direct a beam of ultrasound energy at a location of interest. The beam may generate ultrasound signals along a scanline defined by a trajectory of the beam through the location of interest. The receive beamformer may receive reflected ultrasound energy from portions of the region of interest that lie along the scanline. The receive beamformer may comprise a flag table generated for each beam and for each data channel and a processor that generates raw image data comprising a plurality of pixels. The flag table may comprise a flag associated with each of the RF samples provided by the front-end unit. An RF index may correspond to a delay time associated with receiving an RF sample based on the data clock. Each flag may be a single-bit binary flag indicator having a positive or a non-positive value. The processor may perform operations in real-time comprising processing each of the RF samples provided by the front-end unit based on the flag table for each of the data channels and for each beam of ultrasound energy directed at the location of interest. The processing may further comprise: 1) receiving an RF sample at a clock cycle of the data clock, the RF sample associated with a location along the scanline defined by a trajectory of the beam through the location of interest; 2) sending the received RF sample to a first pixel in a per-channel image buffer if the flag associated with the received RF sample has a positive value and if the flag is a first positive flag; 3) discarding the received RF sample if the flag associated with the received RF sample has a non-positive value; 4) receiving a subsequent RF sample corresponding to a next clock cycle of the data clock; 5) sending the subsequent RF sample to a next pixel in the per-channel image buffer if the flag associated with the subsequent RF sample has a positive value; 6) discarding the subsequent RF sample if the flag associated with the subsequent RF sample has a non-positive value; 7) repeating steps 4-6 until all channels receive an RF sample for a last pixel in the scanline; and 8) adding the RF samples corresponding to a pixel from all of the data channels to generate an image value for the pixel. The image processor may process the raw image data to provide the processed image data. The delay time may correspond to a round-trip time of flight of the ultrasound signal from a location of the object to the transducer. The location of the object may be a location along a scanline defined by a trajectory of the beam through the region of interest. The flag table may be compressed. The processor may perform further operations comprising decoding the compressed flag table. The compressed flag table may be compressed by a factor greater than 10 compared to a delay table. The compressed flag table may be compressed by a factor greater than 50 compared to a delay table. The flag table based real-time beamformer may be implemented on one or more field programmable gate array (FPGA) chips. An equivalent gate count of active circuitry to implement the flag table based real-time beamformer may be no more than 100,000 exclusive of a memory component. The device may comprise a first dimension no more than 210 mm, a second dimension no more than 75 mm and a third dimension no more than 38 mm. The first dimension may comprise no more than 140 mm, the second dimension may comprise no more than 50 mm and the third dimension may comprise no more than 25 mm. Power may be supplied by an external power module or battery having a battery lifetime of at least about 1 hour when the device is used to scan continuously. A memory of the beamformer may comprise no more than 2.5 KB per channel of a multi-channel beamformer.

In another aspect, a method of processing ultrasound signals received from a plurality of data channels may comprise: 1) directing a beam of ultrasound energy at a region of interest, the beam generating ultrasound signals along a scanline defined by a trajectory of the beam through the region of interest; 2) receiving, by a plurality of data channels, reflected ultrasound signals from portions of the region of interest that lie along the scanline; 3) generating, by the plurality of data channels, radio frequency (RF) signals based on the received reflected ultrasound signals; 4) amplifying and digitizing the generated RF signals received from the plurality of data channels to provide RF samples at an RF sampling rate associated with a data clock having a clock cycle; 5) generating a flag table for each beam and for each data channel; 6) processing each of the RF samples based on the flag table for each of the data channels and for each beam of ultrasound energy directed at the region of interest; and 7) processing the raw image data to provide the processed image data. An RF sample may be received by each of the plurality of data channels at each clock cycle corresponding to the RF sampling rate. The RF sample may be associated with a location along the scanline defined by a trajectory of the beam through the region of interest. The flag table may comprise a flag associated with each of the RF samples. Each RF index may correspond to a delay time associated with receiving an RF sample based on the data clock. Each flag may be a single-bit binary flag indicator having a positive or a non-positive value. Processing may further comprise: 1) receiving an RF sample at a clock cycle of the data clock; 2) sending the received RF sample to a first pixel in a per-channel image buffer if the flag associated with the received RF sample has a positive value and if the flag is a first positive flag; 3) discarding the received RF sample if the flag associated with the received RF sample has a non-positive value; 4) receiving a subsequent RF sample corresponding to a next clock cycle of the data clock, 5) sending the subsequent RF sample to a next pixel in the per-channel image buffer if the flag associated with the subsequent RF sample has a positive value; 6) discarding the subsequent RF sample if the flag associated with the subsequent RF sample has a non-positive value; 7) repeating steps 4-6 until all channels receive an RF sample for a last pixel in the scanline; and 8) adding the RF samples corresponding to a pixel from all data channels to generate an image value for the pixel. The RF sample associated with a location along the scanline may be defined by a trajectory of the beam through the region of interest. The delay time may correspond to a round-trip time of flight of the ultrasound signal from a location of the object to the transducer. The location of the object may be a location along a scanline defined by a trajectory of the beam through the region of interest. The method may comprise compressing the flag table. The method may comprise decoding the compressed flag table.

In another aspect, a system comprises a processor and logic encoded in one or more non-transitory computer-readable media for execution by the processors. When executed, the logic may be operable to perform operations comprising: 1) directing a beam of ultrasound energy at a region of interest; 2) receiving, by a plurality of data channels, reflected ultrasound signals from portions of the region of interest that lie along the scanline; 3) generating, by the plurality of data channels, radio frequency (RF) signals based on the received reflected ultrasonic signals; 4) amplifying and digitizing the generated RF signals received from the plurality of data channels to provide RF samples at an RF sampling rate associated with a data clock having a clock cycle; 5) generating a flag table for each beam and for each data channel; 6) processing each of the RF samples based on the flag table for each of the data channels and for each beam of ultrasound energy directed at the location of interest; and 7) processing the raw image data to provide the processed image data. The beam may generate ultrasound along a scanline defined by a trajectory of the beam through the region of interest. An RF sample may be received by each of the plurality of data channels at each clock cycle corresponding to the RF sampling rate. The RF sample may be associated with a location along the scanline defined by a trajectory of the beam through the region of interest. Each RF index may correspond to a delay time associated with receiving an RF sample based on the data clock. Each flag may be a single-bit binary flag indicator having a positive or a non-positive value. The RF sample may be associated with a location along the scanline defined by a trajectory of the beam through the region of interest. The delay time may correspond to a round-trip time of flight of the ultrasound signal from a location of the object to the transducer. The location of the object may be a location along a scanline defined by a trajectory of the beam through the region of interest. The performed operations may comprise compressing the flag table. The performed operations may comprise decoding the compressed flag table. The system may be implemented on one or more FPGA chips. The system may be implemented by an equivalent gate count of active circuitry that is no more than 100,000 exclusive of a memory component. A memory of the system may require no more than 2.5 KB per channel of a multi-channel beamformer.

In addition, the present methods and apparatus may provide improved high-resolution ultrasound images with data compression, such as ultrasound images from an imaging probe (e.g., a handheld imaging probe). Data such as pixel data can be compressed on the handheld (or "hand held") imaging probe prior to transmission by dynamic range compression (e.g., from a first dynamic range to a second dynamic range less than the first dynamic range) in order to decrease the amount of data transmitted from the probe and/or to prepare image data suitable for display. The dynamic range compressed data can be generated quickly and in accordance with clock cycles of a processor in order to decrease latency between receiving uncompressed pixels and generating compressed pixels. The dynamic range compression circuitry may comprise an amount of memory related to a dynamic range of the compressed data that is independent of the dynamic range of the input data, which can decrease memory, decrease power consumption, and decrease latencies of image transmission. The dynamic range compression circuitry can be configured to pipeline data such as image data in accordance with clock cycles, such that throughput between inputting data words and outputting data words is increased. A dynamic range compressed image may comprise the same number of pixels as an uncompressed image in order to maintain spatial resolution. The compression may be performed in accordance with a lookup table in order to increase throughput of generating dynamic range compressed data, thereby decreasing degradation of the compressed data.

In another aspect, a handheld ultrasound probe for generating a plurality of pixels of a plurality of ultrasound images comprises an ultrasound transducer array and an analog-to-digital (A/D) converter. The A/D converter may be coupled to the ultrasound transducer array to acquire ultrasound data. A processor may be coupled to the A/D converter and configured with instructions that, when executed, cause the processor to generate a plurality of uncompressed pixels of the plurality of ultrasound images and generate the plurality of compressed pixels from the uncompressed pixels of the plurality of ultrasound images.

In another aspect, a method for generating pixels of a plurality of ultrasound images with handheld ultrasound probe comprises generating a plurality of uncompressed pixels of the plurality of ultrasound images with a processor coupled to an A/D converter. A plurality of compressed pixels may be generated from the plurality of uncompressed pixels.

In another aspect, an apparatus for compressing input words of m bits to output words of n bits, wherein n<m, comprises a plurality of n memory components and a logic circuit. Each memory component may be configured to store a respective sub-table of a lookup table. The lookup table may comprise a plurality of ordered threshold values, the threshold values corresponding to a domain of a monotonic function and respective indices of the threshold values as ordered corresponding to a range of the monotonic function. The logic circuit may comprise operations for: determining, in a plurality of n stages respectively corresponding to the plurality of n sub-tables, based on an input word and the plurality of n sub-tables, a plurality of n bits of an output word. The logic circuitry may comprise operation for concatenating the plurality of n bits to generate the output word.

In another aspect, a logic circuit is configured for compressing input words of m bits to output words of n bits, wherein n<m. The logic circuit may comprise operations for determining a plurality of n bits of an output word, in a plurality of n pipeline stages respectively corresponding to a plurality of n sub-tables of a lookup table. The lookup table may comprise a plurality of $(2^n)-1$ ordered threshold values, and each $i^{th}$ sub-table of the n sub-tables may comprise $2^{(i-1)}$ threshold values. The threshold values may correspond to a domain of a monotonic function, and respective indices of the threshold values as ordered may correspond to a range of the monotonic function. The plurality of n bits may be concatenated to generate the output word, wherein each stage generates one bit of the output word. A latency of the logic circuit may be at most n clock cycles and a throughput of the logic circuit may be at least one output word per cycle.

In addition, the systems and methods disclosed herein may provide improved imaging with a handheld (or "hand held") ultrasound imaging system. The probe may be configured to generate images capable of spatially resolving tissue structures no more than a wavelength of ultrasound waves emitted from the handheld ultrasound imaging system. The spatial resolution of the tissue structure may comprise an axial resolution of the image along the ultrasound beam path. The handheld ultrasound imaging system may comprise an ultrasound transducer array and a processor configured to generate pixels of the images and can be configured to generate compressed images that resolve the tissue structure. The ultrasound imaging system can be configured to compress individual pixels of the images and provide images comprising the compressed pixels, such that the compressed images comprise the spatial resolution of the uncompressed images. The ultrasound imaging system may comprise communication circuitry to transmit compressed image data such as compressed pixels of the ultrasound images. The communication circuitry may be wireless or wired, or combinations thereof. The communication circuitry and processor can be configured such that the communication circuitry transmits first pixels of an image from the handheld ultrasound imaging system prior to receiving last pixels of an image from the processor in order to decrease latencies, which can be helpful with transmission over networks such as wireless networks. The handheld ultrasound imaging system may comprise an analog-to-digital (A/D) converter coupled to the transducer array and the processor. The ultrasound imaging system may comprise a housing to support the ultrasound transducer array, the A/D converter, the processor and the communication circuitry.

The handheld ultrasound imaging system may comprise a weight of no more than 300 grams (g) and draw power of no more than about 15 watts (W) when performing real-time imaging of the tissue with a resolution capable of resolving the tissue structure displayed in the image.

The handheld ultrasound system may comprise a plurality of components arranged to provide a decreased size and weight. In some instances, the handheld ultrasound system is configured to be held in the hand of a user. In some cases, the handheld ultrasound system is configured to allow a patient to conduct a measurement on himself or herself. The handheld ultrasound system may comprise a housing to contain the measurement components, and the housing is sized, in some instances, such that the user can readily grasp the housing and lift the measurement components within the housing. The compactness and decreased mass of the handheld ultrasound system may allow the system to be easily held in the hand and transported. In many embodiments, the probe of the handheld ultrasound system comprises a maximum dimension across within a range from about 80 mm to about 200 mm, or about 100 mm to about 140 mm, or about 110 mm to about 130 mm, and a mass within a range from about 100 grams to about 500 grams, or about 200 grams to about 400 grams, or about 250 grams to about 350 grams. In many embodiments, the handheld ultrasound system is configured without internal moving parts in order to increase the reliability of the system. The handheld ultrasound system is optionally configured to be dropped from a distance of about one foot, and provide a change in measurement repeatability and accuracy of no more than 1%, for example.

In another aspect, a handheld ultrasound probe for generating a plurality of ultrasound images of tissue structure comprises an ultrasound transducer array to generate ultrasound waves comprising a wavelength. A processor may be coupled to the ultrasound transducer array. The processor may be configured with instructions that when executed cause the processor to receive ultrasound data derived from the ultrasound transducer array and generate the plurality of ultrasound images, the plurality of ultrasound images comprising an axial resolution capable of resolving the tissue structure no more than the wavelength. The processor may be configured with instructions to output the plurality of ultrasound images.

In another aspect, a method for generating a plurality of ultrasound images of tissue structure with a handheld ultrasound imaging probe comprises generating ultrasound waves with an ultrasound transducer array, in which the ultrasound waves comprise a wavelength. Ultrasound data from the ultrasound transducer array is received with an A/D converter. The plurality of ultrasound images may be generated with a processor, in which the plurality of ultrasound images comprise an axial resolution resolving the tissue structure no more than the wavelength. The plurality of ultrasound images may be output from the handheld ultrasound imaging probe.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

The novel features of the invention are set forth with particularity in the appended claims. A better understanding of the features and advantages of the present invention will be obtained by reference to the following detailed description that sets forth illustrative embodiments, in which the principles of the invention are utilized, and the accompanying drawings of which:

DETAILED DESCRIPTION

While various embodiments of the invention have been shown and described herein, it will be obvious to those skilled in the art that such embodiments are provided by way of example only. Numerous variations, changes, and substitutions can occur to those skilled in the art without departing from the invention. It should be understood that various alternatives to the embodiments of the invention described herein can be employed.

In the figures shown herein, like numbers refer to like elements.

Figure 1:
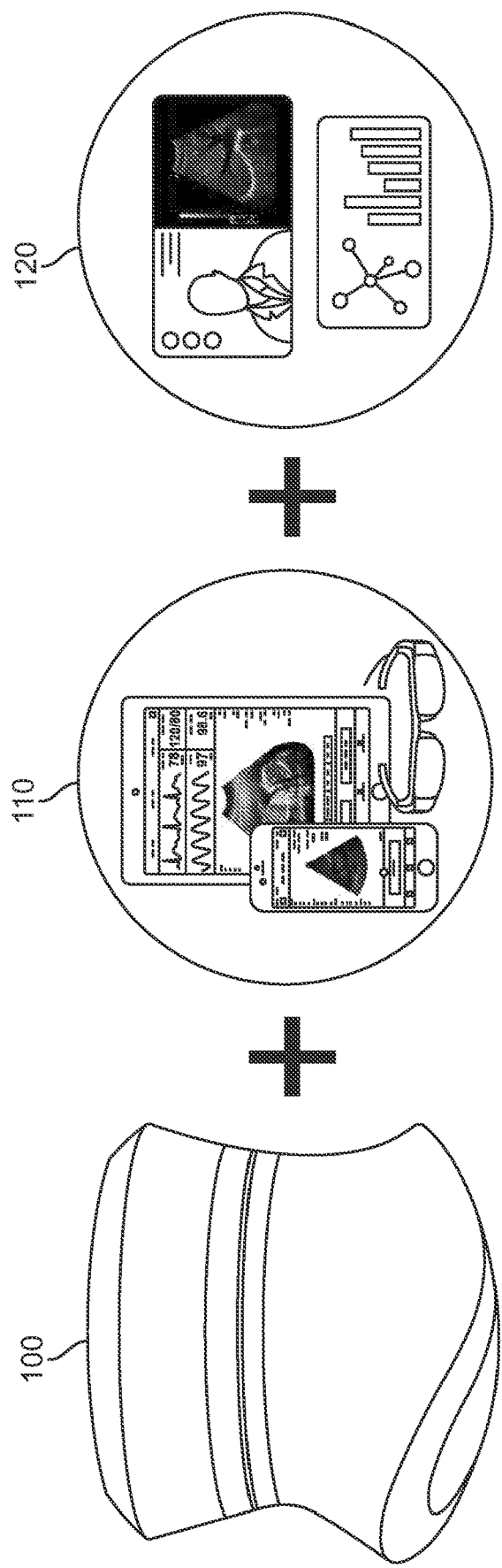
FIG. 1 shows a schematic of a handheld ultrasound system capable of communicating with an external device.

FIG. 1 shows a schematic of a handheld ultrasound system capable of communicating with an external device. The handheld ultrasound device 100 can comprise one or more ultrasonic transducers, one or more ultrasound beamforming components, one or more electronic devices to control the beamforming components, one or more batteries or external power modules, and one or more wireless transceivers.

The handheld ultrasound device can utilize components that are selected and arranged in such a manner as to provide a decreased size and weight. The handheld ultrasound device can be configured to be held in the hand of a user. The handheld ultrasound device can be configured to allow a patient to conduct a measurement on himself or herself. The handheld ultrasound device can comprise a housing to contain the measurement components, and the housing can be sized such that the user can readily grasp the housing and lift the measurement components within the housing. The compactness and decreased mass of the handheld ultrasound device can allow the system to be easily held in the hand and transported.

The handheld ultrasound device can comprise a maximum dimension across within a range from about 80 mm to about 200 mm, or about 100 mm to about 180 mm, or about 120 mm to about 160 mm, or about 130 mm to about 150 mm. The handheld ultrasound device can comprise a second dimension across within a range from about 10 mm to about 90 mm, or about 20 mm to about 80 mm, or about 30 mm to about 70 mm, or about 40 mm to about 60 mm. The handheld ultrasound device can comprise a third dimension across within a range from about 5 mm to about 45 mm, or about 10 mm to about 40 mm, or about 15 mm to about 35 mm, or about 20 mm to about 30 mm. The handheld ultrasound device can comprise a mass within a range from about 100 grams to about 500 grams, or about 200 grams to about 400 grams, or about 250 grams to about 350 grams.

The handheld ultrasound device can be configured without internal moving parts in order to increase the reliability of the system. The handheld ultrasound device can be configured to be dropped from a distance of about one foot, and provide a change in measurement repeatability and accuracy of no more than 1%, for example.

The handheld ultrasound device can utilize components selected and arranged in such a manner as to require and/or consume less memory and power as compared with conventional or non-handheld ultrasound devices. One or more of the ultrasound beamforming components can be implemented on a field programmable gate array (FPGA). In some instances, all of the beamforming components are implemented on the FPGA. One or more of the ultrasound beamforming components can be implemented on an application specific integrated circuit (ASIC). In some instances, all of the beamforming components are implemented on the ASIC. The FPGA or ASIC can utilize an equivalent gate count of no more than about 1,000,000 gates, no more than about 500,000 gates, no more than about 200,000 gates, no more than about 100,000 gates, no more than about 50,000 gates, no more than about 20,000 gates, or no more than about 10,000 gates. The FPGA or ASIC can utilize an equivalent gate count within a range defined by any two of the preceding values. The FPGA or ASIC can utilize memory resources of no more than about 10,000 kilobits, no more than about 5,000 kilobits, no more than about 2,000 kilobits, no more than about 1,000 kilobits, no more than about 500 kilobits, no more than about 200 kilobits, or no more than about 100 kilobits. The FPGA or ASIC can utilize memory resources within a range defined by any two of the preceding values. The FPGA or ASIC can have a power draw of no more than about 1000 mW, no more than about 500 mW, no more than about 200 mW, no more than about 100 mW, no more than about 50 mW, no more than about 20 mW, or no more than about 10 mW. The FPGA or ASIC can have a power draw within a range defined by any two of the preceding values.

One or more batteries or external power modules can be used to power the handheld ultrasound device. The batteries or external power modules can allow the handheld ultrasound device to be utilized for a lifetime of greater than about 0.5 hours, greater than about 1 hour, greater than about 2 hours, greater than about 5 hours, or greater than about 10 hours when the handheld ultrasound device is in continuous operation. The batteries or external power modules can allow the handheld ultrasound device to be utilized for a lifetime within a range defined by any two of the preceding values.

The handheld ultrasound device can be configured to utilize the systems and methods described herein to operate with reduced memory and computational processing requirements as compared to traditional, non-handheld ultrasound devices. The handheld ultrasound device can be configured to utilize a memory no greater than 68 kB for a 32 channel ultrasound system utilizing the systems and methods described herein. The handheld ultrasound device can be configured to utilize a memory no greater than 2.5 kB per channel of the ultrasound system. The receive (Rx) beamformer can be configured to utilize a memory no greater than 68 kB for a 32 channel ultrasound system. The Rx beamformer can be configured to utilize a memory no greater than 2.5 kB per channel of the ultrasound system.

The systems and methods described herein can allow reduced memory and computational processing requirements while maintaining high-quality ultrasound imaging capabilities. In particular, the systems and methods can allow the ultrasound beamforming operations with minimal error in calculated delay times. The systems and methods described herein can allow operations with errors in delay times that are within half of an RF sampling period.

In addition, the systems and methods described herein may allow reduced memory, computational, and communication processing requirements while maintaining high-quality ultrasound imaging capabilities. In particular, the systems and methods may allow a plurality of ultrasound images to be compressed, thereby yielding one or more advantages, such as (i) a reduction in memory requirements, (ii) a reduction in the amount of data transferred from the portable ultrasonic device to the display (e.g., over a wireless communication), and (iii) an increased sensitivity of low-intensity signals made possible by compression with a non-linear function.

The handheld ultrasound device can communicate the results of an ultrasound measurement via a communication channel to a portable electronic device 110, such as a tablet, smartphone, smartwatch, smartglasses, or other portable handheld electronic device. The handheld ultrasound device can communicate the results of an ultrasound measurement via a communication channel to a television or computer monitor. The communication channel can be a wired communication channel. The communication channel can be a wireless communication channel. The wireless communication can be via Bluetooth communication or other short distance wireless communication. The wireless communication can be via Wi-Fi communication. The wireless communication can be via any other wireless communication known to one having skill in the art.

The results can be partially or fully processed ultrasound images. All processing of the ultrasound image can be performed on the handheld ultrasound device. For instance, the handheld ultrasound device can include hardware or software elements that allow ultrasound signals to be converted into electronic representations. The handheld ultrasound device can further include hardware or software elements that allow processing of the electronic representations to extract, for instance, an ultrasound image. The handheld ultrasound device can further include hardware or software elements that allow post-processing of the ultrasound image to improve the image quality.

The portable electronic device can display results and analysis of the ultrasound measurement on one or more applications 120. The applications may comprise mobile applications, desktop applications, laptop application, or television applications. The one or more applications can comprise an environment that displays the ultrasound image. The one or more applications can comprise an environment that allows sharing of the ultrasound image with a specialist, such as a radiologist or ultrasound technician. The specialist can interpret the results of the ultrasound image to provide clinical advice, such as a diagnosis, based on the results of the ultrasound image. In this manner, the handheld ultrasound system can be used by a patient or by a health care provider even in facilities lacking access to specialists capable of interpreting ultrasound results. The one or more applications can allow sharing of ultrasound images with a specialist in near real time. This capability can allow the specialist to provide instructions to the user on how to operate the handheld ultrasound device. For instance, the near real time image sharing capability can allow the specialist to direct a patient or health care provider to move the handheld ultrasound device to a different location on the patient's body. The real time image sharing capability can provide near real time feedback on whether the handheld ultrasound is properly positioned to obtain ultrasound images of a desired location within the patient's body. In this manner, the handheld ultrasound system can be used even by a patient or health care provider who has little or no experience in the use of ultrasound systems.

Figure 2:
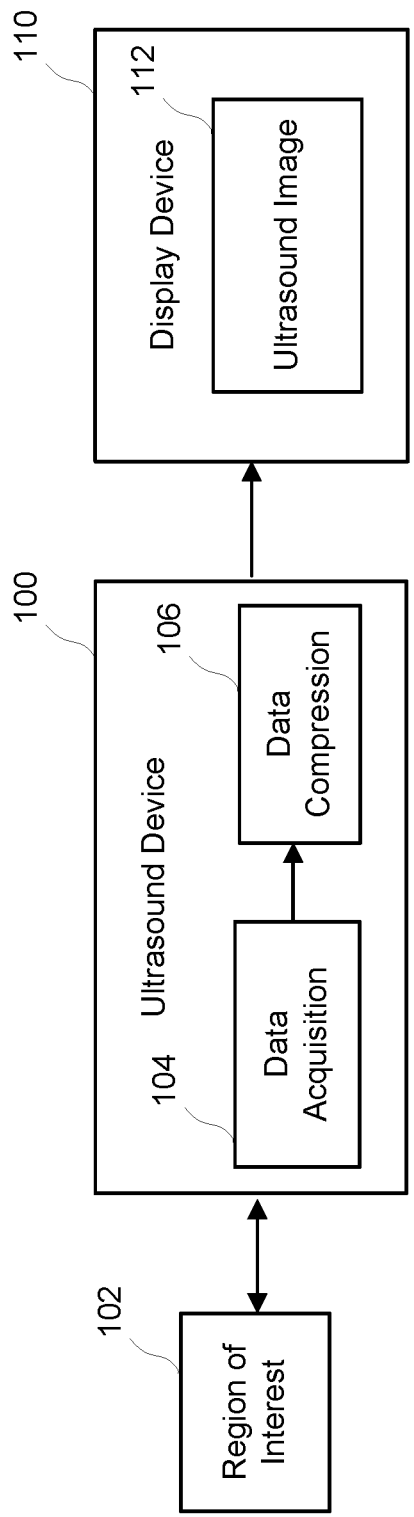
FIG. 2 shows a block diagram of an ultrasound imaging device used to image a region of interest.

FIG. 2 shows a block diagram of an ultrasound imaging device used to image a region of interest. An ultrasound device 100 sends ultrasonic energy, such as in the form of ultrasonic waves, to a medium based on a particular region of interest 102, and receives reflected ultrasonic waves from the region of interest. The region of interest can comprise a space that is being imaged. The region of interest can include any one or more objects. The region of interest can comprise a region inside of a patient's body. In some cases, the region of interest can comprise a fetus in a womb. In some instances, the region of interest can comprise an internal organ of the patient, such as a heart, lung, kidney, bladder, or any other organ. The region of interest can comprise a portion of an organ. The region of interest can comprise more than one organ. In some cases, the region of interest can comprise multiple objects clustered in the same vicinity. For example, the region of interest can include a cluster of objects such as multiple bladder stones in a bladder. In some cases, the region of interest can represent multiple portions or landmarks of an organ, such as multiple components of a heart. For example, such portions or landmarks of a heart can include a right ventricle, a left ventricle, a right atrium, a left atrium, and a thoracic aorta. The systems and methods described herein can be applied to imaging of regions that include multiple objects.

As described in more detail below, the ultrasound device 100 can process the reflected ultrasonic waves and can send processed image data to a display device 110. The ultrasound device may comprise data acquisition circuitry 104, and data compression circuitry 106 to compress data received from the data acquisition circuitry.

The display device can display an ultrasound image 112 based on the processed image data received from the ultrasound device. In some cases, the ultrasound image can show one or more objects located in a particular space that reflect ultrasonic waves emitted by the ultrasound device back to the ultrasound device. The display device can be located at a position near to the ultrasound device, such as in the same room as the ultrasound device. The display device can be located at a position remote from the ultrasound device. For instance, the ultrasound device can be located at a physician's office while the display device can be located at a hospital or the office of a specialist who is able to interpret ultrasound images. The display device can be configured to communicate with an image reproduction device such as a digital display, a printer, a wearable device, an augmented-reality device, a virtual-reality device, a 3-dimensional (3D) display, etc.

Although reference is made to circuitry to acquire and compress ultrasound data, the data acquisition and data compression circuitry as described herein can be configured in many ways to process and compress many types of data, and the type of data acquired and compressed is not limited to ultrasound data. Further the data acquisition and compression circuitry as described herein can be located off of a hand held probe. Data acquisition circuitry 104 can be configured to acquire data from any data source, such as a video signal, an audio signal, an ultrasound or other medical imaging signal, a sound wave, an electrical signal, or another type of analog or digital signal, for example. Data compression circuitry 106 can be configured to compress the acquired data with any type of data compression method such as image compression or pixel compression as described herein, for example. Alternatively or in combination, data compression circuitry 106 can be configured to compresses analog or digital data and may produce analog or digital compressed data. Image compression may be performed by a lossless or lossy compression method (e.g. JPEG, GIF). Pixel compression may be performed by reducing the number of bits representing a pixel, such as dynamic range reduction using a lookup table (e.g., using a compression function), bit truncation (e.g., removing one or more most significant bits or least significant bits), or averaging adjacent pixel values. The data compression circuitry 106 may be configured to downsample images (e.g., removing a portion of images from the data to reduce frame rate) or pixels (e.g., removing a portion of pixels from the data to reduce spatial resolution of images).

Figure 3:
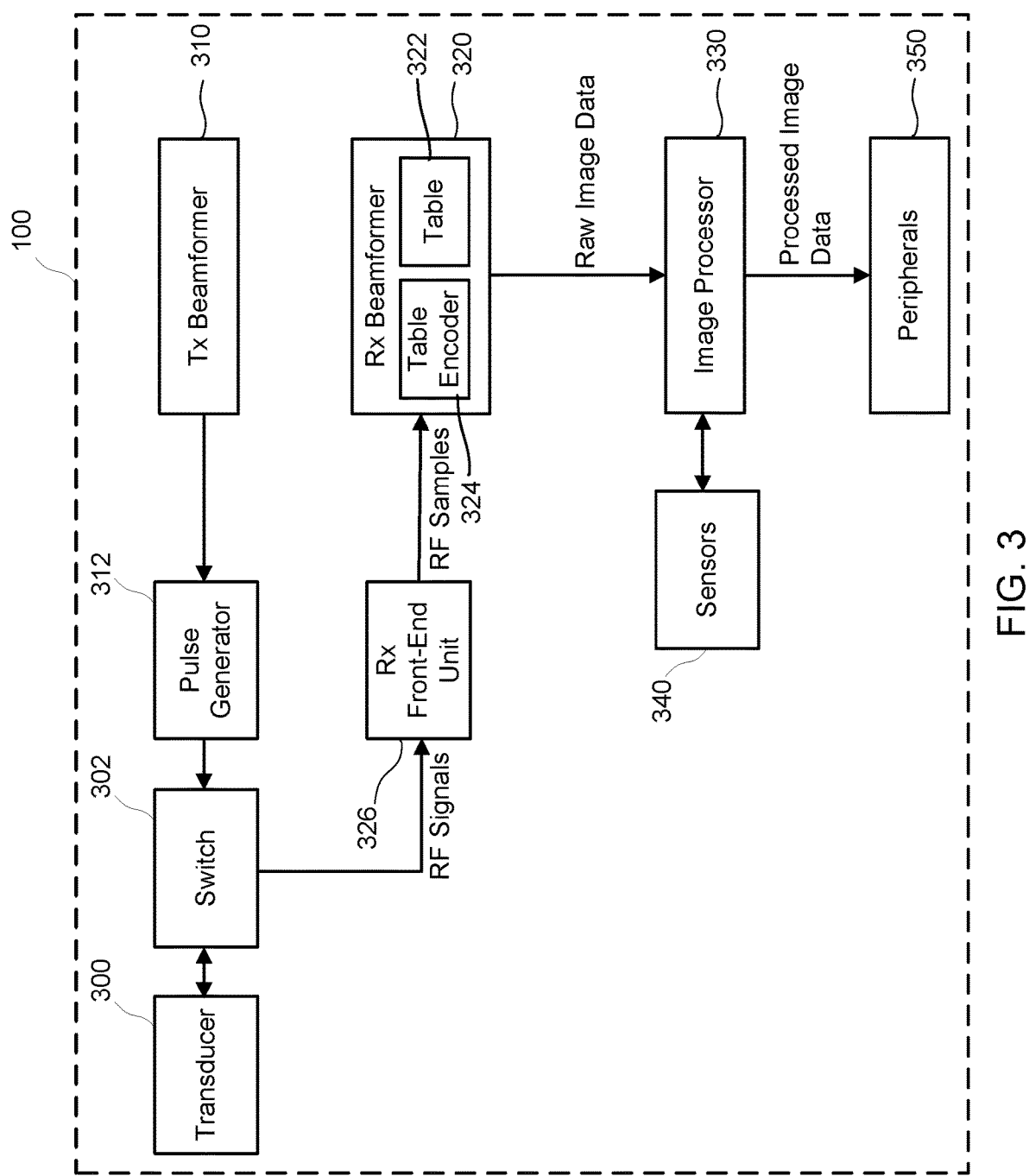
FIG. 3 shows a block diagram of an example ultrasound device.

FIG. 3 shows a block diagram of an example ultrasound device. The ultrasound device 100 can comprise a transducer array 300. The transducer array can comprise one or more transducer elements. Each transducer element can be referred to as a channel. The transducer array can comprise 32 transducer elements, 64 transducer elements, 128 transducer elements, or 256 transducer elements. The transducer array can comprise a number of elements within a range defined by any two of the preceding values. The transducer array can comprise fewer than 32 transducer elements. The transducer array can comprise more than 256 transducer elements.

In some cases, each of the transducer elements can be of the same type. For example, the transducer elements can be piezoelectric transducer elements. The transducer elements can be capacitive transducer elements. The transducer elements can be any transducer element as is known to one having skill in the art. In some cases, the transducer elements can vary in type. For instance, some transducer elements can be piezoelectric transducer elements while other transducer elements are capacitive transducer elements. When an electrical pulse is applied to a given transducer element, the transducer element vibrates and produces the ultrasound, or ultrasonic wave, which is directed at the region of interest. Conversely, when a given transducer element is vibrated by returning ultrasound echoes from objects in the region of interest, the transducer element produces radio frequency (RF) signals. Since the transducer elements can act to both produce and receive ultrasound signals, the ultrasound device can further comprise a switch 302. The switch may comprise a plurality of switches. The switch may comprise a switch network. The switch may comprise a multiplexer (mux). The switch may comprise a demultiplexer (demux). The switch may comprise a plurality of muxes. The switch may comprise a plurality of demuxes.

The ultrasound device can further comprise a transmit (Tx) beamformer 310. The Tx beamformer causes a pulse generator 312 to generate electrical signals based on transmit beamforming. These pulses are then applied to the transducer array to direct ultrasound waves to the region of interest. The electrical signals or pulses can be produced at a predetermined pulse rate. For instance, the electrical signals can be produced at a rate greater than 100 pulses per second, greater than 200 pulses per second, greater than 500 pulses per second, greater than 1000 pulses per second, greater than 2000 pulses per second, greater than 5000 pulses per second, or greater than 10000 pulses per second. The electrical signals may be produced at a pulse rate within a range defined by any two of the preceding values. The pulse generator may control the length of a pulse. The pulse generator may control the total number of pulses applied during a signal acquisition. The pulse generator may control the amplitude of the electrical signals, which may in turn control the intensity and energy of an ultrasound beam produced by the transducer array.

The transducer array can be positioned in direct contact with a surface, such as the body of a patient. For instance, the transducer array can be positioned in direct contact with the abdomen of a patient. In some cases, the transducer array is not in direct contact with the surface. For example, there can be water or another medium between the transducer array and the surface. In some cases, an ultrasound gel can be used to couple the transducer array with a surface. The transducer array shapes a beam of ultrasonic waves or pulses to give the beam a particular size and shape at various depths within a particular space beneath the surface. In some cases, the transducer array focuses ultrasonic waves to a particular location. In other cases, the transducer array produces ultrasonic waves which are not localized to a particular location. For instance, the transducer array can utilize synthetic aperture imaging. The transducer array can utilize multi-beam imaging. The transducer array can scan the ultrasound beam over region of interest.

When the transducer array receives ultrasonic waves reflected by objects in the region of interest, the transducer array generates RF signals based on the reflected ultrasonic waves. The reflected ultrasonic waves can also be referred to as ultrasonic echoes, or ultrasound echoes, or echoes. The RF signals can also be referred to as raw RF data.

Reception of the ultrasound signals is controlled by a receive (Rx) beamformer 320. The Rx beamformer can comprise a table 322. The table can comprise a flag table or a compressed flag table, as discussed herein. The Rx beamformer can comprise a table decoder 324, as described herein. The table decoder can comprise a flag table decoder, as described herein. The Rx beamformer can be communicatively coupled to an Rx front-end unit 326. The Rx front-end unit can amplify and digitize RF signals from the transducer array to provide RF samples. The Rx front-end unit can comprise an analog-to-digital converter (ADC). The Rx front-end unit can send the RF samples to the Rx beamformer. In some instances, the Rx front-end unit amplifies and/or filters the RF signals before digitizing them. In some cases, the amplifier gain of the Rx front-end unit can vary over time, in order to compensate for attenuation of the ultrasound signals.

The Rx beamformer can generate raw image data based on the RF samples, where the Rx beamformer performs beamforming functions in order to generate the raw image data. The Rx beamformer can create an intensity map of the reflected ultrasonic waves corresponding to every point in the field of view. The Rx beamformer can map the received signal to a location in an image and coherently sum the signals from all transducer elements for every point in the field of view.

Given a high enough sampling rate, one or more of the transducers may receive a plurality of RF samples corresponding to an ultrasound signal emanating from a particular location in a region of interest. In the far field, this may occur when the sampling rate is greater than twice the spacing between pixels in an image line divided by the speed of sound. Each of the plurality of RF samples corresponding to the ultrasound signal from the location may be regarded as conveying information about the location that is at least partially redundant. Thus, any one of the plurality of RF samples corresponding to the ultrasound signal from the location may be sufficient to reconstruct image information for that location. The Rx beamformer may therefore select to utilize only a fraction of the RF samples corresponding to the ultrasound signal from the location. The Rx beamformer may select to utilize one or more of the RF samples in order to reconstruct image information for the location. For instance, the Rx beamformer may select to utilize the RF sample that is closest to the center of a given pixel. Utilizing only a fraction of the RF samples may allow for a reduction in the memory requirements for the handheld ultrasound device.

The Rx beamformer can determine which of the RF samples are to be used to generate raw image data based on the table. The table can indicate which RF samples are to be used to generate raw image data and which RF samples are not to be used to generate raw image data. The table can be predetermined in that information in the table is generated prior to an imaging session. The table can be pre-loaded in the Rx beamformer or in any other suitable storage location. During runtime, the Rx beamformer can check the table during an imaging session in order to determine which RF samples to use to generate raw image data. Implementations of the table are described in more detail herein.

The Rx beamformer can generate raw image data based on the RF samples that are to be used to generate raw image data. The raw image data can then be sent to an image processor 330.

The image processor can process the raw image data received from the Rx beamformer to provide processed image data.

The ultrasound device can further comprise one or more sensors 340. The sensors can include position sensors, rotational sensors, tilt sensors, gyroscopes, or accelerometers for positioning the ultrasound device. The sensors can comprise any other positioning sensor as is known to one having skill in the art.

The ultrasound device can further comprise one or more peripherals 350. The peripherals can comprise one or more display devices. The peripherals can send processed image data to remote display devices, such as a 2D display, a 3D display, a printer, a wearable device, an augmented-reality device, or a virtual-reality device. Remote display devices can comprise stand-alone computers, tablet computers, smartphones, dedicated monitors, etc. The peripherals can comprise one or more medical devices, such as an electrocardiograph (ECG or EKG), pulse oximeter, position tracker, needle guide, or any other medical device as is known to one having skill in the art.

One or more of the components 300, 302, 310, 312, 320, 322, 324, 326, 330, 340, or 350 of the ultrasound device can be implemented on an FPGA. In some cases, all of the components 300, 302, 310, 312, 320, 322, 324, 326, 330, 340, or 350 of the ultrasound device are implemented on an FPGA. In some cases, components 320, 322, and 324 are implemented on an FPGA. One or more of the components 300, 302, 310, 312, 320, 322, 324, 326, 330, 340, or 350 of the ultrasound device can be implemented on an ASIC. In some cases, all of the components 300, 302, 310, 312, 320, 322, 324, 326, 330, 340, or 350 of the ultrasound device are implemented on an ASIC. In some cases, components 320, 322, and 324 are implemented on an ASIC. The FPGA or ASIC can utilize an equivalent gate count of no more than about 1,000,000 gates, no more than about 500,000 gates, no more than about 200,000 gates, no more than about 100,000 gates, no more than about 50,000 gates, no more than about 20,000 gates, or no more than about 10,000 gates. The FPGA or ASIC can utilize an equivalent gate count within a range defined by any two of the preceding values. The FPGA or ASIC can utilize memory resources of no more than about 10,000 kilobits, no more than about 5,000 kilobits, no more than about 2,000 kilobits, no more than about 1,000 kilobits, no more than about 500 kilobits, no more than about 200 kilobits, or no more than about 100 kilobits. The FPGA or ASIC can utilize memory resources within a range defined by any two of the preceding values. The FPGA or ASIC can have a power draw of no more than about 1000 mW, no more than about 500 mW, no more than about 200 mW, no more than about 100 mW, no more than about 50 mW, no more than about 20 mW, or no more than about 10 mW. The FPGA or ASIC can have a power draw within a range defined by any two of the preceding values.

Figure 4:
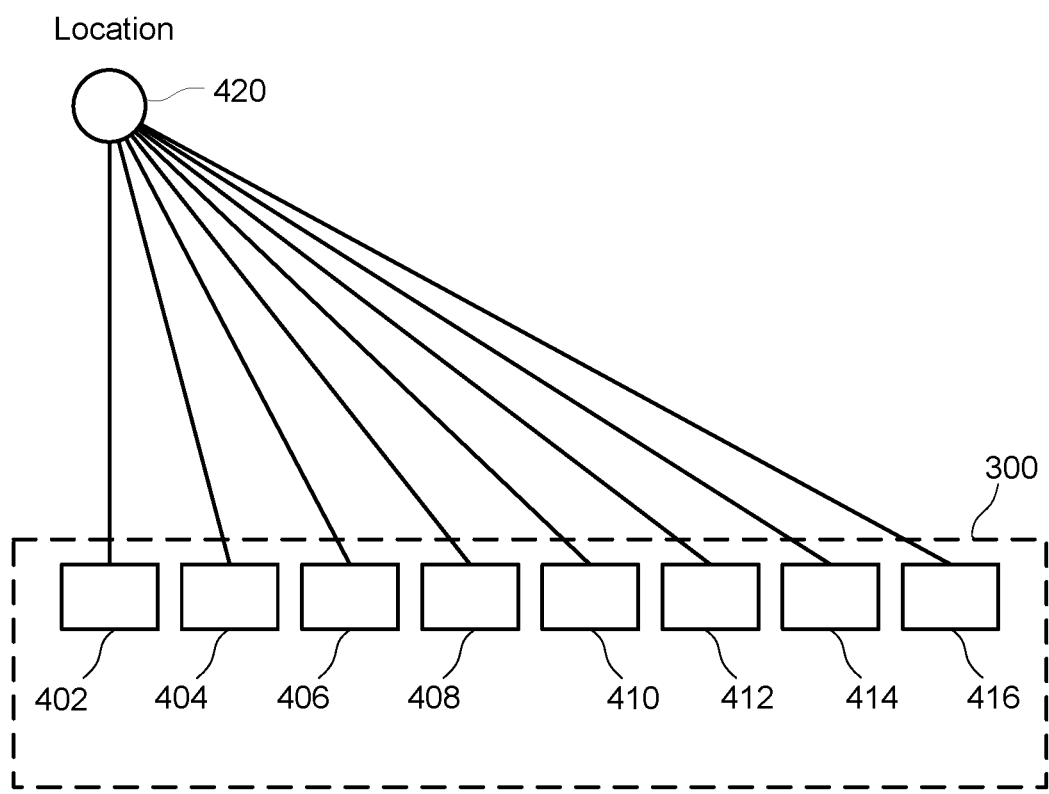
FIG. 4 shows a simplified example ultrasound transducer array.

FIG. 4 shows a simplified example ultrasound transducer array. The transducer array 300 can comprise transducer elements 402, 404, 406, 408, 410, 412, 414, and 416. The transducer elements can be piezoelectric transducer elements. The transducer elements can be capacitive transducer elements. The transducer element can be any other transducer elements as are known to one having skill in the art.

The transducer array can be any type of transducer array as is known to one having skill in the art. For example, the transducer array can be a one-dimensional array. The transducer array can be a linear sequential array. The transducer array can be a linear phased array. The transducer array can be a curved or convex sequential array. The transducer array can be an annular array. The transducer array can be a 2-dimensional array. The transducer can be a 2-dimensional rectangular array. The transducer array can include any number of transducer elements.

The transducer array shapes a beam of ultrasonic waves or pulses to give the beam a particular size and shape at various depths within a particular space beneath a surface. In some cases, the transducer array focuses ultrasonic waves to a particular location. In other cases, the transducer array produces ultrasonic waves which are not localized to a particular location. For instance, the transducer array can utilize synthetic aperture imaging. The transducer array can utilize multi-beam imaging. The transducer array can scan the ultrasound beam over the region of interest.

Regardless of the manner in which the transducer array directs ultrasonic waves at the region of interest, reflected ultrasound signals will emanate from multiple locations within the region of interest. For ease of illustration, FIG. 4 shows a single location 420 from which an ultrasound signal emanates. The ultrasound signal emanating from the location may comprise a reflected ultrasound signal.

The location can comprise a portion of a region of interest such as an organ in a person's body. Multiple locations can comprise multiple different portions of the region of interest. As such, ultrasound signals received from a set of locations allow reconstruction of an image of the region of interest.

The distance between each transducer element and each specific location, as well as the speed of ultrasound signals, can be known or predetermined. The round-trip time of flight is the time it takes for an ultrasound wave to travel from one or more transmitting transducer elements to a given region of interest, to be reflected, and to be received by a transducer element. For a given signal, the transmitting transducer element can be the same as the receiving transducer element. However, transmitting transducer elements and receiving transducer elements are not necessarily the same. For example, the round-trip delay can be the one-way delay from one or more transmitting elements to a location plus the one-way delay from the field point to a different receiving transducer element. This round-trip time of flight can be referred to as a delay time. The delay time of each respective signal can be converted to a distance.

Figure 5:
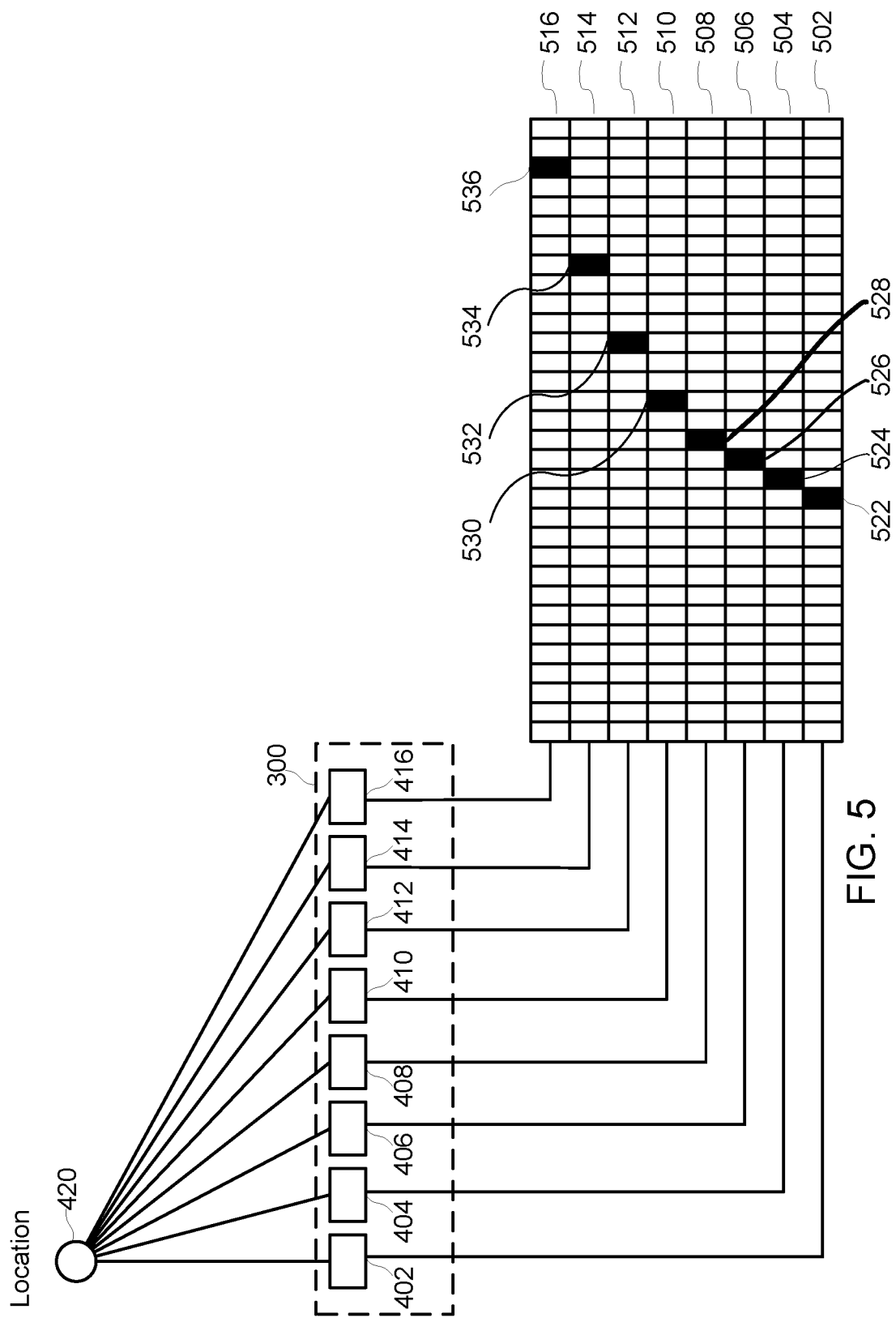
FIG. 5 shows example time delays for receipt of an ultrasound signal at each channel in an example ultrasound transducer array.

FIG. 5 shows example time delays for receipt of an ultrasound signal at each channel in an example ultrasound transducer array. Each channel in the transducer array can produce a series of RF samples over time. For instance, channel 402 can produce a series of RF samples 502. Channel 404 can produce a series of RF samples 504. Channel 406 can produce a series of RF samples 506. Channel 408 can produce a series of RF samples 508. Channel 410 can produce a series of RF samples 510. Channel 412 can produce a series of RF samples 512. Channel 414 can produce a series of RF samples 514. Channel 416 can produce a series of RF samples 516.

Due to the geometric relationships between the location and the various transducer elements, an ultrasound signal emanating from the location 420 is first received by channel 402. Prior to receipt of the ultrasound signal from the location, RF samples received at channel 402 contain no information that can be used to reconstruct one or more image pixels corresponding to that location. Such RF samples are indicated as white boxes in FIG. 5. Upon receipt of the ultrasound signal at a first delay time, channel 402 receives one or more RF samples 522 containing information that can be used to reconstruct one or more image pixels corresponding to the location. Such RF samples are indicated as black boxes in FIG. 5. The ultrasound signal is next received by channel 404 at a second delay time, which produces one or more RF samples 524 containing information that can be used to reconstruct one or more image pixels corresponding to the location. The ultrasound signal is received sequentially at third, fourth, fifth, sixth, seventh, and eight delay times, respectively, by channels 406, 408, 410, 412, 414, and 416. In response, channels 406, 408, 410, 412, 414, and 416 each produce one or more RF samples 526, 528, 530, 532, 534, and 536, respectively, containing information that can be used to reconstruct one or more image pixels corresponding to the location.

The schematics detailed in FIGS. 4 and 5 apply to ultrasound signals received from a single location in space. One or more of the transducers may receive ultrasound signals from a plurality of locations in space. Each such ultrasound signal may be associated with a plurality of delay times at each transducer channel.

RF samples from all receiving transducer elements can be used. That is to say, a pixel in an image can be reconstructed using multiple RF samples received by multiple transducer elements. For instance, one or more RF samples from each transducer element can be used to reconstruct a pixel in an image.

When the RF data is sampled at a high enough sampling frequency, each receiving transducer element can receive a larger number of RF samples than the number of image pixels corresponding to a line in an image for a given data acquisition. An RF sample that is used in reconstructing a line in an image can be used only once for a single pixel for each line. The Rx beamformer can determine whether each RF sample received by each channel is to be used, if at all, in the reconstruction of an image or one or more pixels in an image. A used RF sample may be used for reconstruction of a fraction of the total number of image pixels. In some cases, a used RF sample may be used for reconstruction of one or more image pixels.

A trend can arise when examining the relationships between ultrasound signals obtained at a single transducer element for locations that are located near to one another. Each used RF sample received by a given transducer can be associated with a location. The locations can be indexed by image pixel index numbers. The pixel indices can be defined within each image line of an image. The pixel index can start at the location in the line that is closest to the transducer array. The pixel index can increase for locations that are further from the transducer array.

For each transducer, an RF sample received earlier in time can contribute to the reconstruction of an image pixel located closer to that transducer. For instance, the first used RF sample of a channel can be associated with the first image pixel of an image line, the second used RF sample can be associated with the second image pixel of the image line, and so on. The Rx beamformer can continuously increase the pixel index for each Rx channel.

Figure 6:
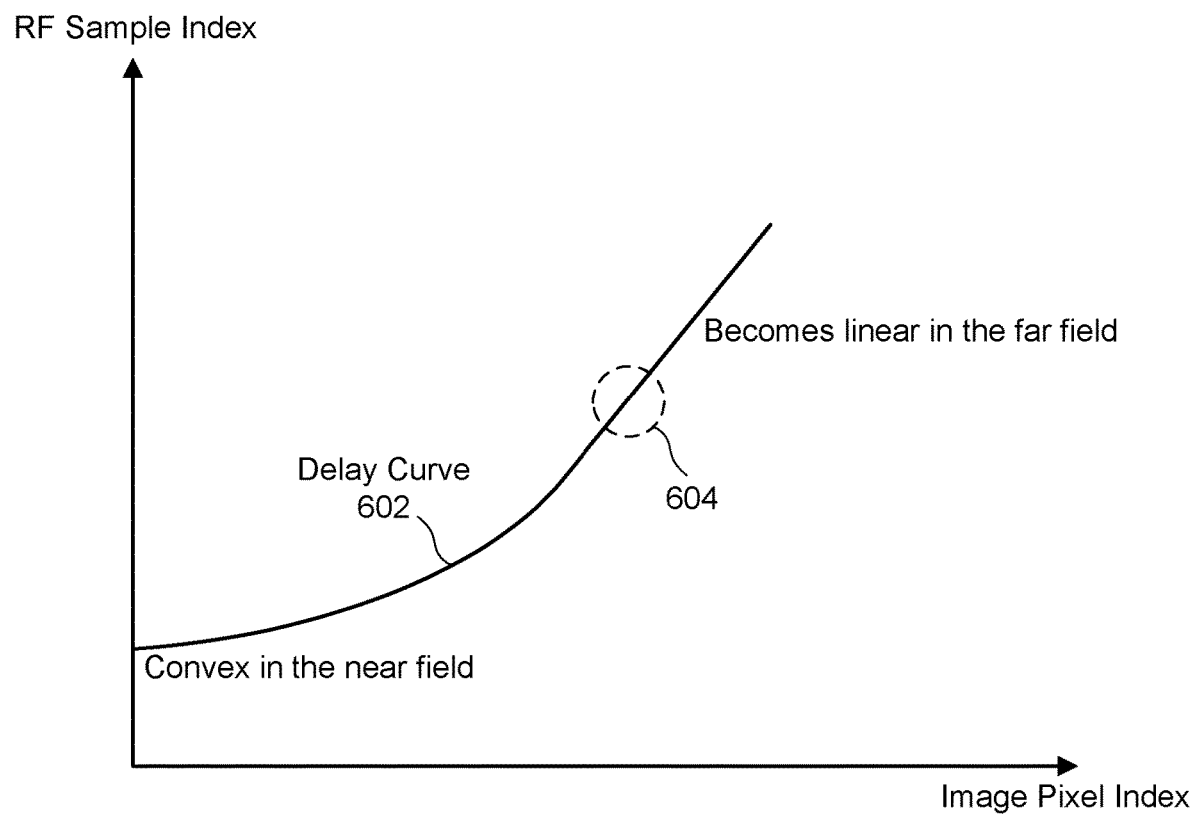
FIG. 6 shows a simplified graph of a delay curve associated with the time delays for receipt of an ultrasound signal from each location in a line, for one transducer channel.

FIG. 6 shows a simplified graph of a delay curve associated with the time delays for receipt of an ultrasound signal from each location in a line, for one transducer channel. The x-axis corresponds to the image pixel index. The y-axis corresponds to the RF sample index, or the sample number at which the ultrasound signal is received at a given transducer. The delay curve can be defined as the delay time as a function of image pixel index. The RF sample index can be approximately proportional to the delay time. In cases in which the transducer element samples at a uniform sampling rate, the RF sample index can be proportional to the delay time. If the image pixel spacing is uniform, the delay curve 602 may be strongly non-linear in the near field for pixels characterized by small indices. If the image pixel spacing is uniform, the delay curve may become nearly linear in the far field for pixels characterized by large indices. A nearly linear portion 604 of the delay curve is described in more detail in FIG. 7.

Figure 7:
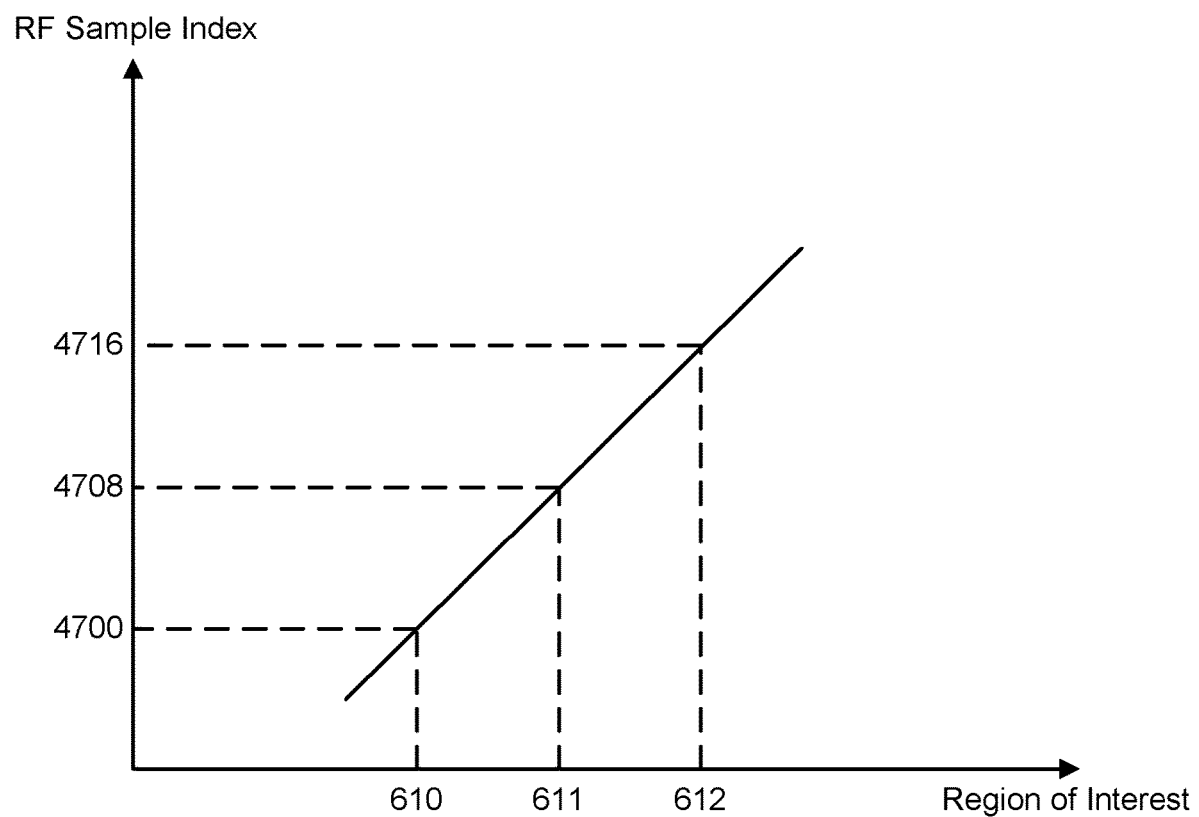
FIG. 7 shows a simplified graph of a portion of a delay curve associated with the time delays for receipt of an ultrasound signal from each location in a line, for one transducer channel.

FIG. 7 shows a simplified graph of a portion of a delay curve associated with the time delays for receipt of an ultrasound signal from each location in a line, for one transducer channel. An example of the nearly linear behavior of the delay curve in the far field is provided. In the far field, image pixels with indices 610, 611, and 612 can be associated with RF samples with indices 4700, 4708, and 4716, respectively.

In both the strongly non-linear and nearly linear portions of the delay curve, the delay time can increase monotonically with the pixel index. The combination of sparsity, periodicity, and monotonicity can allow compression of the table. This, in turn, can allow for a significant reduction in the computational resources required to carry out Rx beamforming on a handheld ultrasound device. For instance, compression of the table can allow for a significant reduction in the memory resources required to carry out Rx beamforming on a handheld ultrasound device.

The table can include positive indicators that indicate which RF samples are to be used to generate image data. The table can also include negative indicators that indicate the RF samples that are not to be used to generate image data. An indicator can associate with each RF sample received by each channel. In other words, each RF sample can be associated with either a positive indicator or a negative indicator.

The table can be referred to as a flag table. The flag table can utilize positive flags as positive indicators and negative flags as negative indicators. In this manner, each RF sample can be associated with either a positive flag or a negative flag. Each indicator or flag can be a 1-bit indicator. For example, a positive indicator can be a binary "1", or a "1-flag". A negative indicator can be a binary "0", or a "0-flag". Other binary conventions can be utilized, such as assigning a 0-flag as a positive indicator and a 1-flag as a negative indicator. Alternatively, more than one bit can be used as an indicator. In such cases, any binary coding scheme can be used to assign positive and negative indicators.

For each RF sample from each channel, the RF sample can be used, or stored into a memory device, if the flag is a 1-flag. The RF sample can be discarded, or not stored into memory, if the flag is a 0-flag. An RF sample with a 1-flag and associated with an $i^{th}$ image pixel can be stored in association with the $i^{th}$ image pixel in an image line of an image buffer. In some cases, two or more RF samples (originating, for instance, from two or more channels), each with a 1-flag and associated with an $i^{th}$ image pixel, can be added together in the image buffer.

The image buffer can store image data. In some cases, the image buffer may not store an entire set of image data, but instead may store only one or more partial or complete image lines. The image buffer can store multiple lines. Once the one or more image lines have been stored within the image buffer and are ready for further processing, the image data for the one or more lines can be transferred to the image processor before the beamformer starts to receive the RF samples for the next image line. Thus, it can be sufficient for the image buffer to have a memory capacity for only one image line or multiple image lines. It may not be necessary for the image buffer to have a memory capacity for the full image data.

Because all RF samples are processed immediately when they are received, there can be no need for an RF buffer. The flag table can replace a delay table which stores the delay values for all image pixels. In some cases, the flag table can require a smaller amount of memory than a delay table. Moreover, the real-time processing capability enabled by the flag table can eliminate the need for an RF buffer, further reducing the memory requirement.

Figures 8A, 8B:
FIG. 8A shows a simplified example delay table for a channel in an example ultrasound transducer array.
FIG. 8B shows a simplified flag table for a channel in an example ultrasound transducer array.

FIGS. 8A and 8B show a simplified example delay table for a channel in an example ultrasound transducer array and a simplified flag table for a channel in an example ultrasound transducer array, respectively. As shown in FIG. 8A, a delay table can store a delay time for each image pixel, for each transducer element. For instance, a delay table 800 can store delay times of 4700, 4708, 4716, 4724, and 4732 for image pixels with indices of 610, 611, 612, 613, and 614, respectively. A delay table can also store delay times for image pixels with indices smaller than 610 and for image pixels with indices greater than 614. The need to store delay times can require substantial memory resources. For instance, a delay table for an ultrasound system utilizing 32 channels and 6400 RF samples per channel, with an image resolution of 76×761 pixels, can require the storage of 2 bytes of data for each delay time. This can correspond to a delay table size of approximately 3.53 MB. Additionally, use of a delay table can require the use of an RF buffer. For an ultrasound system utilizing 32 channels, 6400 RF samples per channel, and 2 bytes of memory per RF sample, an RF buffer of approximately 0.4 MB can be required. Thus, the memory resources required for implementing a delay table using such an exemplary ultrasound system can total approximately 3.93 MB.

As shown in FIG. 8B, a flag table can store a 1-bit indicator for each RF sample received at each channel. For instance, a flag table 810 can store a 0-flag, 1-flag, 0-flag, 0-flag, 0-flag, 0-flag, 0-flag, 0-flag, 0-flag, 1-flag, 0-flag, 0-flag, 0-flag, 0-flag, 0-flag, 0-flag, 0-flag, 1-flag, and 0-flag for RF samples with indices 4699, 4700, 4701, 4702, 4703, 4704, 4705, 4706, 4707, 4708, 4709, 4710, 4711, 4712, 4713, 4714, 4715, 4715, and 4717, respectively. A flag table can also store 1-bit indicators for RF samples with indices less than 4699 or greater than 4717. A flag table can store 1-bit indicators for all RF samples received at each channel. The number of 1-bit indicators stored in a flag table can be greater than the number of delay times stored in a delay table. However, flag table can utilize fewer memory resources owing to the use of 1-bit flags in place of much larger delay times, such as 2-byte delay times. For instance, a flag table for an ultrasound system utilizing 32 channels, 6400 RF samples per channel, and 2 bytes of memory per RF sample, with an image resolution of 76×761 pixels, can require the storage of a flag table with a size of approximately 1.86 MB. The use of a flag table can obviate the need for an RF buffer. Thus, the use of a flag table can reduce the memory requirements for an ultrasound device by a factor greater than 2 compared to the use of a delay table. The exact factor may depend on the fraction of RF samples used and the amount of memory used to store each delay time in conventional beamforming. For instance, using ⅛ of the RF samples may yield a flag table with 8 times more entries than a delay table utilized in conventional beamforming. However, each entry in the flag table may occupy only 1 bit, compared to 16 bits in a delay table. Thus, the flag table may reduce the overall memory requirements by a factor greater than 2 in this example. The used RF samples can comprise no more than about 1% of the total number of RF samples, no more than about 2% of the total number of RF samples, no more than about 5% of the total number of RF samples, no more than about 10% of the total number of RF samples, no more than about 20% of the total number of RF samples, or no more than about 50% of the total number of RF samples. The used RF samples can comprise a portion of the total number of RF samples within a range defined by any two of the preceding values.

Delay times can be pre-calculated based on every distance from each transducer element to each focus point in space that is to be reconstructed. Each delay time can be saved in a look-up table. Each receiving transducer element can have a predetermined delay time associated with each location in a space being imaged. The delay times can be stored in advance of imaging. Similarly, the flag table, which is constructed from the delay times, can be stored in advance of imaging. The flag table can then be later accessed during operation. In some cases, the flag table may not change as long as the geometry of the imaging space, the transducer array, and/or the imaging scheme do not change.

To determine which of the RF samples are to be used to generate image data, the Rx beamformer can determine which of the RF samples are associated with positive indicators in the flag table. In such a determination, positive indicators can indicate the RF samples that are to be used to generate image data. For example, if a given RF sample is associated with a 1-flag in the flag table, that RF sample can be used to generate image data. Accordingly, the Rx beamformer can send incoming RF samples associated with a 1-flag to the image buffer.

To determine which of the RF samples are not to be used to generate image data, the Rx beamformer can determine which of the RF samples are associated with negative indicators in the flag table. In such a determination, negative indicators can indicate the RF samples that are not to be used to generate image data. For example, if a given RF sample is associated with a 0-flag in the flag table, that RF sample may not be used to generate raw image data. Accordingly, the Rx beamformer can ignore incoming RF samples associated with a 0-flag.

The Rx beamformer can send the RF samples that are to be used to generate image data to an image buffer, where the RF samples that are to be used to generate image data are added to the corresponding image pixel in the image buffer. The index of the corresponding image pixel can be one more than the number of RF samples in this Rx channel that have been used so far. The Rx beamformer can send each RF sample associated with a positive indicator to the image buffer immediately after acquisition of that RF sample.

An RF sample can be received by each channel at every data clock. The Rx beamformer can check the indicator or flag for the current RF sample. If the flag is a 0-flag, the Rx beamformer can discard the RF sample. If the flag is a 1-flag, the Rx beamformer can send the RF sample to an image buffer. The first used RF sample of the channel can be added to the first pixel in the image line of the image buffer, and the following used RF samples can be added to the following pixels in the image line of the image buffer, in the order of arrival.

When the slowest channel receives the RF sample for a given pixel, the RF samples from all channels for this pixel can be summed to calculate the image value of this pixel. For instance, the slowest channel can be one of the two edge channels of the active Rx aperture, or the first or last transducer in a line of transducers. Thus, the Rx beamformer can only need to check the progress of the two edge channels. When the two edge channels receive RF samples for a given pixel, the Rx beamformer can presume that all other channels have received RF samples for the pixel.

The Rx beamformer can discard the RF samples that are not to be used to generate image data. By not storing the RF samples that are not to be used to generate image data, the memory consumption can be reduced.

The 1-flags and 0-flags in the flag table can have a characteristic pattern of bits, and this pattern can be used to compress the flag table further. The flag table can be compressed in order to further reduce memory consumption. The compression can occur when the flag table is constructed and before the Rx beamformer accesses the flag table during runtime. During runtime, the Rx beamformer can decode the compressed flag table in order to determine which of the RF samples are to be used to generate raw image data. The flag table can be decoded in real time, so as to determine which RF samples to use in real time.

The flag table can include a predetermined pattern of positive indicators and negative indicators which can be substantially periodic. The periodicity can be especially pronounced in the far field. The periodicity can arise because, in the far field, the distances from a given transducer element to each location increases almost linearly, as a result of the uniform spacing between image pixels in an image line. Also, the delay times associated with those distances can increase substantially linearly.

As shown in FIGS. 6 and 7, the delay curve becomes substantially linear in the far field. This behavior is manifested in the flag table as shown in FIG. 8B, where the number of 0-flags between two consecutive 1-flags is substantially constant for RF samples obtained from locations that are relatively far from the transducer. The relatively constant number of 0-flags between two consecutive 1-flags can allow for further compression of the flag table. The number of 0-flags between two consecutive 1-flags can be referred to as NZ. There can be a predetermined number of 0-flags between two consecutive 1-flags, and this pattern can repeat. If the delay curve were perfectly linear, then the flag table would always have the same number of 0-flags between two 1-flags. However, because the delay curve is not perfectly linear, the number of 0-flags between two 1-flags will change over the field of RF samples.

The space surrounding a given transducer element can be divided into two zones or regions. The zone relatively close to the transducer element can be referred to as the near field, and the zone further from the transducer element can be referred to as the far field. The behavior of the delay curve determines how NZ changes when moving from the near field to the far field. An initial value of NZ can be determined by the starting image depth, the transducer element location, and the angle of the image line. For instance, a shallow imaging depth will produce a relatively small initial NZ, as the difference in the distance from a transducer to a first image pixel and the distance from the transducer to a second image pixel located adjacent to the first image pixel is relatively small for a shallow imaging depth. A deeper imaging depth will produce a relatively large initial NZ, as the difference in the distance from a transducer to a first image pixel and the distance from the transducer to a second image pixel located adjacent to the first image pixel is relatively large for a deeper imaging depth. At near field, NZ can be relatively small. NZ can monotonically increase with distance from the transducer to a location. At far field, NZ can converge to a nearly constant number which is determined by the RF sampling rate and the image pixel spacing. Thus, for instance, NZ can converge to a value of 7 in the far field, as in FIG. 8B. NZ can converge to any non-negative numerical value. NZ can converge to any non-negative integer value.

For portions of the flag table where the delay curve is approximately linear, less information can need to be saved because information specifying the slope of the delay curve, which does not change much, can be saved instead. The value of NZ can be correlated to the slope of the delay curve. Because the delay curve is mostly linear, but not perfectly linear, the slope of delay curve can change over the region being imaged. Thus, the compressed flag table can store a representation of only the initial slope of the delay curve and the locations where the slope of the delay curve changes. As such, the compressed flag table may not need to save all 1-flags and 0-flags. This can all reduce the size of the compressed flag table.

The flag table encoder can store the RF sample index of the first positive indicator. The flag table encoder can assign an initial NZ based on the number of negative indicators between the two first positive indicators. The flag table encoder can assume that the next positive indicator will be attained after NZ negative indicators. The flag table encoder can examine the flag table to determine whether this behavior is observed. If the flag table fails to conform to this behavior, the flag table encoder can alter the value of NZ in order to account for the non-linear behavior of the delay curve. If a negative indicator is observed when a positive indicator is expected, the flag table encoder can alter the value of NZ by increasing this value. If a positive indicator is observed when a negative indicator is expected, the flag table encoder can regard this behavior as an exception and leave NZ at its present value.

The predetermined pattern can be related to the slope of the delay curve. Information about the slope can be stored in the compressed flag table. The delay curve can be defined as the delay time as a function of image pixel index. The slope information can be predetermined and already stored in the compressed flag table before imaging. The slope can be equivalent to NZ, as NZ=round(slope−1).

The flag table encoder can start with the index of the first 1-flag and an initial NZ for the first two 1-flags. The flag table encoder can then scan the flag table, expecting a 1-flag after every NZ 0-flags based on the predetermined pattern. In some cases, a flag may not match this expectation. Such a disagreement between the position of the 1-flag predicted by NZ and the actual position of the 1-flag can indicate that the slope of the delay curve has changed or there has been a quantization error. The beamformer can only need to store the index of each flag at which this disagreement occurs. This can compress the data in the flag table.

Owing to the nature of the delay curve, the number of 0-flags between two 1-flags can only increase with larger and larger pixel index. As such, when there is an unexpected 0-flag, it can be assumed that the slope has increased. Thus, when there is an unexpected 0-flag, the flag table encoder can monotonically increase NZ by 1, as more 0-flags between two 1-flags can be expected from the functional form of the delay curve. The next flag can be expected to be a 1-flag.

In some cases, an unexpected 1-flag can occur such that there are fewer 0-flags between two 1-flags than expected from NZ. The functional form of the delay curve can lead to a belief that this should not happen. Thus, in such a case, a quantization error can be presumed. An unexpectedly early 1-flag can be considered an exception. In the case of an unexpectedly early 1-flag, the flag table encoder can keep the current NZ. The flag table encoder can store the exception. The next flag can be expected to be a 0-flag. The flag table encoder can continue scanning until the last flag has been checked.

The aforementioned activities can produce a compressed flag table. The compressed flag table can comprise an index of the RF sample at which the first 1-flag occurs, an initial NZ, and a list of the indices of RF samples that do not match the expected pattern. The list of RF sample indices that do not match the expected pattern can comprise a list of unexpected 0-flags and unexpected 1-flags. Since the compressed flag table can store only a few pieces of information that specify the full pattern of 1-flags and 0-flags in the flag table, as opposed to a full list of 1-flags and 0-flags stored in the flag table, the compressed flag table can be further substantially reduced in size. For instance, a compressed flag table for an ultrasound system utilizing 32 channels and 6400 RF samples per channel, with an image resolution of 76×761 pixels, can require only approximately 68 kB of storage space. This can be compared to storage space of approximately 1.86 MB for the full flag table and 3.93 MB for a delay table for an ultrasound system operating with the same parameters. Thus, the compressed flag table can reduce the storage requirements by a factor of greater than 25 compared to the full flag table and by a factor of greater than 50 compared to the delay table. The compressed flag table can reduce the storage requirements by a factor of greater than 5, greater than 10, greater than 50, greater than 100, greater than 250, greater than 500, or greater than 1000 compared to the full flag table. The compressed flag table can reduce the storage requirements by a factor of greater than 5, greater than 10, greater than 25, greater than 100, greater than 250, greater than 500, or greater than 1000 compared to the delay table.

The Rx beamformer can decode the compressed flag table at runtime. The first data entries in the compressed flag table can comprise the index of the first used RF sample and an initial NZ. The beamformer can utilize a counter to track the number of 0-flags that have occurred since the last 1-flag. In some cases, no RF sample is stored until the current RF sample index reaches the index of the first used RF sample. When the current RF sample index reaches the value of the first index, the RF sample can be stored to the first image pixel location in the image buffer. The Rx beamformer can then skip the next NZ samples before storing an RF sample to the next location in the image buffer, which can occur when the counter reaches the current NZ. The Rx beamformer can account for indices that do not match the flag pattern expected from the value of NZ. When the current RF sample index reaches the value of the next data entry in the compressed flag table, which may store the next RF sample index that does not match the expected flag pattern, the Rx beamformer may recognize that the current RF sample does not match the expected flag pattern. For instance, if the beamformer notes an unexpected 1-flag before the counter reaches a count of NZ, this can indicate a quantization error. In such case, the sample can be stored to the image buffer and the Rx beamformer can start counting the number of 0-flags until the counter again reaches NZ. If the beamformer notes an unexpected 0-flag when the counter reaches NZ, this can indicate a change in the slope of the delay curve. In such case, the sample can be discarded and the beamformer can increase the value of NZ by one. This process can be repeated until the last pixel in the image line is reconstructed.

Figure 9:
FIG. 9 shows a flowchart of a method for ultrasound beamforming using a flag table or compressed flag table.

FIG. 9 is a flowchart of a method for ultrasound beamforming using a flag table or compressed flag table. The method 900 consists of the steps of directing a beam of ultrasound energy at a region of interest, receiving ultrasound signals from portions of the region of interest, generating RF signals based on received ultrasound signals, amplifying and digitizing the RF signals received, generating a flag table for each beam and for each data channel, optionally compressing the flag table, optionally decoding the compressed flag table, processing each of the RF samples based on the flag table, and processing image data to provide processed image data.

In step 902, one or more beams of ultrasound energy are directed at a region of interest. The one or more beams can generate ultrasound signals along a scanline corresponding to a line in an image. The scanline can be defined by a trajectory of the one or more beams through the region of interest.

In step 904, ultrasound signals are received from portions of the region of interest. The ultrasound signals can arise from reflections of the ultrasound energy from portions of the region of interest that lie along a scanline of the one or more beams. The ultrasound signals can be received by one or more ultrasound transducers in one or more ultrasound transducer arrays. Each of the one or more ultrasound transducers can be referred to as a data channel.

In step 906, RF signals are generated based on the received ultrasound signals. The received signals can arise from reflections of the ultrasound energy from portions of the region of the interest that lie along a scanline of the one or more beams. The RF signals can be generated by causing each of the one or more transducers to vibrate.

In step 908, the RF signals received from the plurality of channels are amplified and digitized. The RF signals can be sampled to provide RF samples at an RF sampling rate that is associated with a data clock. The data clock can have a clock cycle. At each clock cycle, an RF sample can be received by each of the one or more data channels. Each RF sample can be associated with an ultrasound signal emanating from a location along a scanline of the one or more beams.

In step 910, a flag table is generated for each beam and for each data channel. The flag table can comprise a flag associated with each of the RF samples. The flag table may comprise an ordered list of flags. The ordering may correspond to the RF sample index. For instance, the first flag may correspond to the first RF sample index, the second flag may correspond to the second RF sample index, etc. The RF sample index can correspond to a delay time associated with receiving an RF sample. The delay time can be based on the data clock. Each flag can be a single-bit binary flag indicator. Each binary flag indicator can have a positive or a negative value. The positive value can comprise a 1-flag. The negative value can comprise a 0-flag.

In step 912, the flag table is compressed. The compression of the flag table can comprise the step of assigning an initial NZ based on the number of negative binary flag indicators occurring between the first and second positive binary flag indicators in the flag table. The compression can further comprise assuming that the next positive indicator will be attained after NZ negative indicators and examining the flag table to determine whether this behavior is observed. The compression can further comprise storing the index of the flag at which an expected value failed to occur if the flag table fails to conform to this behavior. If an unexpected 1-flag occurs, the compression can comprise storing the index of the unexpected 1-flag. If an unexpected 0-flag occurs, the compression can comprise storing the index of the unexpected 0-flag and incrementing the value of NZ. The compression can comprise continuing to scan the flag table until the last flag has been checked.

In step 914, the compressed flag table is decoded. The decoding of the compressed flag table can comprise noting the index of the first used RF sample and an initial NZ. The decoding of the compressed flag table can further comprise utilizing a counter to track the number of 0-flags that have occurred since the last 1-flag. The decoding of the compressed flag table can further comprise storing a first used RF sample to a first image pixel location in an image buffer when the current RF sample index reaches the value of the first used RF sample index. The decoding of the compressed flag table can further comprise skipping the next NZ samples before storing an RF sample to the next location in the image buffer when the counter reaches NZ. The decoding of the compressed flag table can further comprise accounting for indices that do not match the flag pattern expected from the value of NZ. The decoding of the compressed flag table can further comprise storing a sample to the image buffer when an unexpected 1-flag is encountered before the counter reaches a count of NZ. The decoding of the compressed flag table can further comprise discarding a sample when an unexpected 0-flag is encountered when the counter reaches a value of NZ and incrementing the value of NZ. The decoding of the compressed flag table can further comprise repeating this process until the last pixel in the image line is reconstructed.

In step 916, each of the RF samples is processed based on the flag table. The processing can occur for each data channel and for each ultrasound beam directed to the region of interest. The data channels can comprise one or more edge channels characterized by being located at a farthest point from the center of the transducer array. The data channels can comprise two edge channels. For instance, a linear transducer array may comprise two edge channels corresponding to the ends of the linear array. The data channels can comprise more than two edge channels. For instance, a square transducer array may comprise four edge channels corresponding to the corners of the square array. In another example, a circular transducer array may compromise a plurality of channels located on an outermost radius of the circular array. The data channels can comprise zero edge channels. For instance, an annular array may have all channels located at the same distance from a center of the array and therefore may have no edge channels.

The processing can comprise receiving an RF sample at a first clock cycle of the data clock. The RF sample can be associated with a location along a scanline defined by a trajectory of one or more ultrasound beams through a region of interest. The processing can further comprise sending the RF sample to a first pixel in a per-channel image buffer if the flag associated with the received RF sample has a positive indicator value. The processing can comprise sending the RF sample to a first pixel in a per-channel image buffer only if the flag associated with the received RF sample is the first positive flag. The processing can further comprise discarding the received RF sample if the flag associated with the received RF sample has a negative indicator value. The processing can further comprise receiving a subsequent RF sample corresponding to a next clock cycle of the data clock. The processing can further comprise sending the subsequent RF sample to a first pixel in a per-channel image buffer if the flag associated with the subsequent RF sample has a positive indicator value. The processing can comprise sending the subsequent RF sample to a first pixel in a per-channel image buffer only if the flag associated with the received RF sample is the first positive flag. The processing can further comprise discarding the subsequent RF sample if the flag associated with the subsequent RF sample has a negative indicator value. The processing can further comprise repeating receiving and either retaining or discarding each subsequent RF sample until all edge channels receive the RF samples corresponding to the last image pixel in an image line. The processing can further comprise adding the RF samples corresponding to a pixel from all data channels to generate an image value for the pixel.

In step 918, the raw image data is processed to provide processed image data. The processing can comprise any processing as is known to one having skill in the art.

The method 900 can produce a maximum delay error that is no more than half of an RF sampling period. The method 900 can allow a decision about whether an RF sample is to be used for a certain pixel or not in less than one RF sampling clock cycle after the data sample is captured.

A person of ordinary skill in the art will recognize many variations, alterations and adaptations based on the disclosure provided herein. For example, the order of the steps of the method 900 can be changed, some of the steps removed, some of the steps duplicated, and additional steps added as appropriate. Some of the steps can be performed in succession. Some of the steps can be performed in parallel. Some of the steps can be performed once. Some of the steps can be performed more than once. Some of the steps can comprise sub-steps. Some of the steps can be automated and some of the steps can be manual. The processor as described herein can comprise one or more instructions to perform at least a portion of one or more steps of the method 900.

The systems and methods described herein can be utilized to reconstruct ultrasound images Digital Processing Device In some embodiments, the platforms, systems, media, and methods described herein can comprise a digital processing device, or use of the same. In further embodiments, the digital processing device can comprise one or more hardware central processing units (CPUs) or general purpose graphics processing units (GPGPUs) that carry out the device's functions. In still further embodiments, the digital processing device can further comprise an operating system configured to perform executable instructions. In some embodiments, the digital processing device can be optionally connected to a computer network. In further embodiments, the digital processing device can be optionally connected to the Internet such that it accesses the World Wide Web. In still further embodiments, the digital processing device can be optionally connected to a cloud computing infrastructure. In other embodiments, the digital processing device can be optionally connected to an intranet. In other embodiments, the digital processing device can be optionally connected to a data storage device.

In accordance with the description herein, suitable digital processing devices can include, by way of non-limiting examples, server computers, desktop computers, laptop computers, notebook computers, sub-notebook computers, netbook computers, netpad computers, set-top computers, media streaming devices, handheld computers, Internet appliances, mobile smartphones, tablet computers, personal digital assistants, video game consoles, and vehicles. Those of skill in the art will recognize that many smartphones are suitable for use in the system described herein. Those of skill in the art will also recognize that select televisions, video players, and digital music players with optional computer network connectivity are suitable for use in the system described herein. Suitable tablet computers include those with booklet, slate, and convertible configurations, known to those of skill in the art.

In some embodiments, the digital processing device can comprise an operating system configured to perform executable instructions. The operating system can be, for example, software, including programs and data, which manages the device's hardware and provides services for execution of applications. Those of skill in the art will recognize that suitable server operating systems include, by way of non-limiting examples, FreeBSD, OpenBSD, NetBSD®, Linux, Apple® Mac OS X Server®, Oracle® Solaris®, Windows Server®, and Novell® NetWare®. Those of skill in the art will recognize that suitable personal computer operating systems include, by way of non-limiting examples, Microsoft® Windows®, Apple® Mac OS X®, UNIX®, and UNIX-like operating systems such as GNU/Linux®. In some embodiments, the operating system is provided by cloud computing. Those of skill in the art will also recognize that suitable mobile smart phone operating systems include, by way of non-limiting examples, Nokia® Symbian® OS, Apple® iOS®, Research In Motion® BlackBerry OS®, Google® Android®, Microsoft® Windows Phone® OS, Microsoft® Windows Mobile® OS, Linux®, and Palm® WebOS®. Those of skill in the art will also recognize that suitable media streaming device operating systems include, by way of non-limiting examples, Apple TV®, $R_o k_u$®, Boxee®, Google TV®, Google Chromecast®, Amazon Fire®, and Samsung® HomeSync®. Those of skill in the art will also recognize that suitable video game console operating systems include, by way of non-limiting examples, Sony® P53®, Sony® P54®, Microsoft® Xbox 360®, Microsoft Xbox One, Nintendo® Wii®, Nintendo® Wii U®, and Ouya®.

In some embodiments, the device can include a storage and/or memory device. The storage and/or memory device can be one or more physical apparatuses used to store data or programs on a temporary or permanent basis. In some embodiments, the device can be volatile memory and requires power to maintain stored information. In some embodiments, the volatile memory can comprise dynamic random-access memory (DRAM). In some embodiments, the device can be non-volatile memory and retains stored information when the digital processing device is not powered. In further embodiments, the non-volatile memory can comprise flash memory. In some embodiments, the non-volatile memory can comprise ferroelectric random access memory (FRAM). In some embodiments, the non-volatile memory can comprise phase-change random access memory (PRAM). In other embodiments, the device is a storage device including, by way of non-limiting examples, CD-ROMs, DVDs, flash memory devices, magnetic disk drives, magnetic tapes drives, optical disk drives, and cloud computing based storage. In further embodiments, the storage and/or memory device is a combination of devices such as those disclosed herein.

In some embodiments, the digital processing device can include a display to send visual information to a user. In some embodiments, the display can be a cathode ray tube (CRT). In some embodiments, the display can be a liquid crystal display (LCD). In further embodiments, the display can be a thin film transistor liquid crystal display (TFT-LCD). In some embodiments, the display can be an organic light emitting diode (OLED) display. In various further embodiments, an OLED display can be a passive-matrix OLED (PMOLED) or active-matrix OLED (AMOLED) display. In some embodiments, the display can be a plasma display. In other embodiments, the display can be a video projector. In still further embodiments, the display can be a combination of devices such as those disclosed herein.

In some embodiments, the digital processing device can include an input device to receive information from a user. In some embodiments, the input device can be a keyboard. In some embodiments, the input device can be a pointing device including, by way of non-limiting examples, a mouse, trackball, track pad, joystick, game controller, or stylus. In some embodiments, the input device is a touch screen or a multi-touch screen. In other embodiments, the input device can be a microphone to capture voice or other sound input. In other embodiments, the input device can be a video camera or other sensor to capture motion or visual input. In further embodiments, the input device can be a Kinect, Leap Motion, or the like. In still further embodiments, the input device can be a combination of devices such as those disclosed herein.

Figure 10:
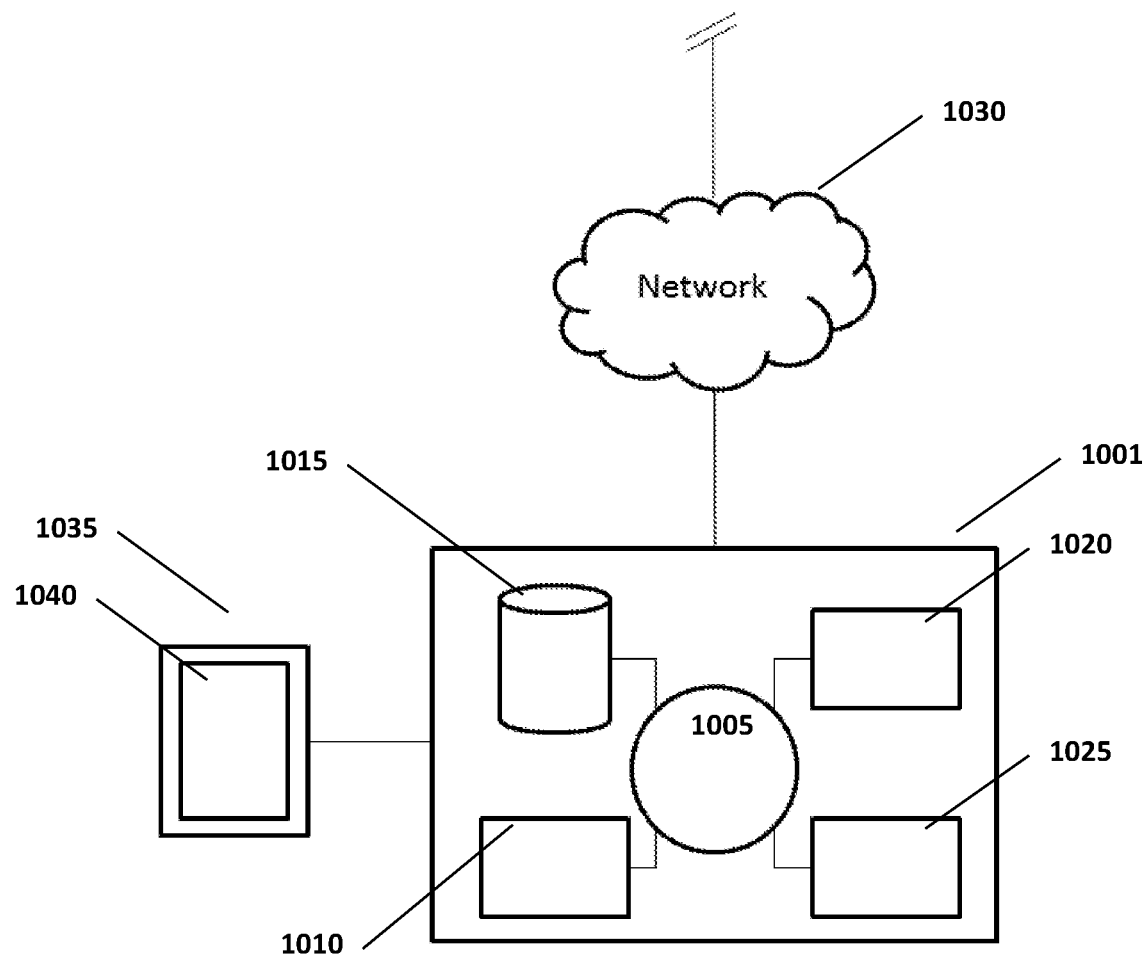
FIG. 10 shows an example computer control system that is programmed or otherwise configured to implement the methods provided herein.

Referring to FIG. 10, in a particular embodiment, an exemplary digital processing device 1001 is programmed or otherwise configured to perform ultrasound beamforming as described herein. The device 1001 can regulate various aspects of the ultrasound beamforming of the present disclosure, such as, for example, performing processing steps. In this embodiment, the digital processing device 1001 includes a central processing unit (CPU, also "processor" and "computer processor" herein) 1005, which can be a single core or multi core processor, or a plurality of processors for parallel processing. The digital processing device 1001 also includes memory or memory location 1010 (e.g., random-access memory, read-only memory, flash memory), electronic storage unit 1015 (e.g., hard disk), communication interface 1020 (e.g., network adapter) for communicating with one or more other systems, and peripheral devices 1025, such as cache, other memory, data storage and/or electronic display adapters. The memory 1010, storage unit 1015, interface 1020 and peripheral devices 1025 are in communication with the CPU 1005 through a communication bus (solid lines), such as a motherboard. The storage unit 1015 can be a data storage unit (or data repository) for storing data. The digital processing device 1001 can be operatively coupled to a computer network ("network") 1030 with the aid of the communication interface 1020. The network 1030 can be the Internet, an internet and/or extranet, or an intranet and/or extranet that is in communication with the Internet. The network 1030 in some cases is a telecommunication and/or data network. The network 1030 can include one or more computer servers, which can enable distributed computing, such as cloud computing. The network 1030, in some cases with the aid of the device 1001, can implement a peer-to-peer network, which can enable devices coupled to the device 1001 to behave as a client or a server.

Continuing to refer to FIG. 10, the CPU 1005 can execute a sequence of machine-readable instructions, which can be embodied in a program or software. The instructions can be stored in a memory location, such as the memory 1010. The instructions can be directed to the CPU 1005, which can subsequently program or otherwise configure the CPU 1005 to implement methods of the present disclosure. Examples of operations performed by the CPU 1005 can include fetch, decode, execute, and write back. The CPU 1005 can be part of a circuit, such as an integrated circuit. One or more other components of the device 1001 can be included in the circuit. In some cases, the circuit is an application specific integrated circuit (ASIC) or a field programmable gate array (FPGA).

Continuing to refer to FIG. 10, the storage unit 1015 can store files, such as drivers, libraries and saved programs. The storage unit 1015 can store user data, e.g., user preferences and user programs. The digital processing device 1001 in some cases can include one or more additional data storage units that are external, such as located on a remote server that is in communication through an intranet or the Internet.

Continuing to refer to FIG. 10, the digital processing device 1001 can communicate with one or more remote computer systems through the network 1030. For instance, the device 1001 can communicate with a remote computer system of a user. Examples of remote computer systems include personal computers (e.g., portable PC), slate or tablet PCs (e.g., Apple® iPad, Samsung® Galaxy Tab), telephones, Smart phones (e.g., Apple® iPhone, Android-enabled device, Blackberry®), or personal digital assistants.

Methods as described herein can be implemented by way of machine (e.g., computer processor) executable code stored on an electronic storage location of the digital processing device 1001, such as, for example, on the memory 1010 or electronic storage unit 1015. The machine executable or machine readable code can be provided in the form of software. During use, the code can be executed by the processor 1005. In some cases, the code can be retrieved from the storage unit 1015 and stored on the memory 1010 for ready access by the processor 1005. In some situations, the electronic storage unit 1015 can be precluded, and machine-executable instructions are stored on memory 1010.

Non-Transitory Computer Readable Storage Medium

In some embodiments, the platforms, systems, media, and methods disclosed herein can include one or more non-transitory computer readable storage media encoded with a program including instructions executable by the operating system of an optionally networked digital processing device. In further embodiments, a computer readable storage medium can be a tangible component of a digital processing device. In still further embodiments, a computer readable storage medium can be optionally removable from a digital processing device. In some embodiments, a computer readable storage medium can include, by way of non-limiting examples, CD-ROMs, DVDs, flash memory devices, solid state memory, magnetic disk drives, magnetic tape drives, optical disk drives, cloud computing systems and services, and the like. In some cases, the program and instructions can be permanently, substantially permanently, semi-permanently, or non-transitorily encoded on the media.

Computer Program

In some embodiments, the platforms, systems, media, and methods disclosed herein can include at least one computer program, or use of the same. A computer program can include a sequence of instructions, executable in the digital processing device's CPU, written to perform a specified task. Computer readable instructions can be implemented as program modules, such as functions, objects, Application Programming Interfaces (APIs), data structures, and the like, that perform particular tasks or implement particular abstract data types. In light of the disclosure provided herein, those of skill in the art will recognize that a computer program can be written in various versions of various languages.

The functionality of the computer readable instructions can be combined or distributed as desired in various environments. In some embodiments, a computer program can comprise one sequence of instructions. In some embodiments, a computer program can comprise a plurality of sequences of instructions. In some embodiments, a computer program can be provided from one location. In other embodiments, a computer program can be provided from a plurality of locations. In various embodiments, a computer program can include one or more software modules. In various embodiments, a computer program can include, in part or in whole, one or more web applications, one or more mobile applications, one or more standalone applications, one or more web browser plug-ins, extensions, add-ins, or add-ons, or combinations thereof.

Web Application

In some embodiments, a computer program can include a web application. In light of the disclosure provided herein, those of skill in the art will recognize that a web application, in various embodiments, utilizes one or more software frameworks and one or more database systems. In some embodiments, a web application is created upon a software framework such as Microsoft®.NET or Ruby on Rails (RoR). In some embodiments, a web application can utilize one or more database systems including, by way of non-limiting examples, relational, non-relational, object oriented, associative, and XML database systems. In further embodiments, suitable relational database systems can include, by way of non-limiting examples, Microsoft® SQL Server, mySQL™, and Oracle®. Those of skill in the art will also recognize that a web application, in various embodiments, is written in one or more versions of one or more languages. A web application can be written in one or more markup languages, presentation definition languages, client-side scripting languages, server-side coding languages, database query languages, or combinations thereof. In some embodiments, a web application can be written to some extent in a markup language such as Hypertext Markup Language (HTML), Extensible Hypertext Markup Language (XHTML), or eXtensible Markup Language (XML). In some embodiments, a web application can be written to some extent in a presentation definition language such as Cascading Style Sheets (CSS). In some embodiments, a web application can be written to some extent in a client-side scripting language such as Asynchronous Javascript and XML (AJAX), Flash® Actionscript, Javascript, or Silverlight®. In some embodiments, a web application is written to some extent in a server-side coding language such as Active Server Pages (ASP), ColdFusion®, Perl, Java™, JavaServer Pages (JSP), Hypertext Preprocessor (PHP), Python™, Ruby, Tcl, Smalltalk, WebDNA®, or Groovy. In some embodiments, a web application can be written to some extent in a database query language such as Structured Query Language (SQL). In some embodiments, a web application integrates enterprise server products such as IBM® Lotus Domino®. In some embodiments, a web application can include a media player element. In various further embodiments, a media player element can utilize one or more of many suitable multimedia technologies including, by way of non-limiting examples, Adobe® Flash®, HTML 5, Apple® QuickTime®, Microsoft® Silverlight®, Java™, and Unity®.

Mobile Application

In some embodiments, a computer program can include a mobile application provided to a mobile digital processing device. In some embodiments, the mobile application can be provided to a mobile digital processing device at the time it is manufactured. In other embodiments, the mobile application can be provided to a mobile digital processing device via the computer network described herein.

In view of the disclosure provided herein, a mobile application can be created by techniques known to those of skill in the art using hardware, languages, and development environments known to the art. Those of skill in the art will recognize that mobile applications can be written in several languages. Suitable programming languages include, by way of non-limiting examples, C, C++, C#, Objective-C, Java™, Javascript, Pascal, Object Pascal, Python™ Ruby, VB.NET, WML, and XHTML/HTML with or without CSS, or combinations thereof.

Suitable mobile application development environments are available from several sources. Commercially available development environments can include, by way of non-limiting examples, AirplaySDK, alcheMo, Appcelerator®, Celsius, Bedrock, Flash Lite, .NET Compact Framework, Rhomobile, and WorkLight Mobile Platform. Other development environments are available without cost including, by way of non-limiting examples, Lazarus, MobiFlex, MoSync, and Phonegap. Also, mobile device manufacturers distribute software developer kits including, by way of non-limiting examples, iPhone and iPad (iOS) SDK, Android™ SDK, BlackBerry® SDK, BREW SDK, Palm® OS SDK, Symbian SDK, webOS SDK, and Windows® Mobile SDK.

Those of skill in the art will recognize that several commercial forums are available for distribution of mobile applications including, by way of non-limiting examples, Apple® App Store, Google® Play, Chrome WebStore, BlackBerry® App World, App Store for Palm devices, App Catalog for webOS, Windows® Marketplace for Mobile, Ovi Store for Nokia® devices, Samsung® Apps, and Nintendo® DSi Shop.

Standalone Application

In some embodiments, a computer program can comprise a standalone application, which is a program that is run as an independent computer process, not an add-on to an existing process, e.g., not a plug-in. Those of skill in the art will recognize that standalone applications are often compiled. A compiler is a computer program(s) that transforms source code written in a programming language into binary object code such as assembly language or machine code. Suitable compiled programming languages include, by way of non-limiting examples, C, C++, Objective-C, COBOL, Delphi, Eiffel, Java™, Lisp, Python™, Visual Basic, and VB .NET, or combinations thereof. Compilation is often performed, at least in part, to create an executable program. In some embodiments, a computer program includes one or more executable complied applications.

Web Browser Plug-in

In some embodiments, the computer program includes a web browser plug-in (e.g., extension, etc.). In computing, a plug-in is one or more software components that add specific functionality to a larger software application. Makers of software applications support plug-ins to enable third-party developers to create abilities that extend an application, to support easily adding new features, and to reduce the size of an application. When supported, plug-ins enable customizing the functionality of a software application. For example, plug-ins are commonly used in web browsers to play video, generate interactivity, scan for viruses, and display particular file types. Those of skill in the art will be familiar with several web browser plug-ins including, Adobe® Flash® Player, Microsoft® Silverlight®, and Apple® QuickTime®. In some embodiments, the toolbar comprises one or more web browser extensions, add-ins, or add-ons. In some embodiments, the toolbar comprises one or more explorer bars, tool bands, or desk bands.

In view of the disclosure provided herein, those of skill in the art will recognize that several plug-in frameworks are available that enable development of plug-ins in various programming languages, including, by way of non-limiting examples, C++, Delphi, Java™, PHP, Python™, and VB .NET, or combinations thereof.

Web browsers (also called Internet browsers) are software applications, designed for use with network-connected digital processing devices, for retrieving, presenting, and traversing information resources on the World Wide Web. Suitable web browsers include, by way of non-limiting examples, Microsoft® Internet Explorer®, Mozilla® Firefox®, Google® Chrome, Apple® Safari®, Opera Software® Opera®, and KDE Konqueror. In some embodiments, the web browser is a mobile web browser. Mobile web browsers (also called micro-browsers, mini-browsers, and wireless browsers) are designed for use on mobile digital processing devices including, by way of non-limiting examples, handheld computers, tablet computers, netbook computers, subnotebook computers, smartphones, music players, personal digital assistants (PDAs), and handheld video game systems. Suitable mobile web browsers include, by way of non-limiting examples, Google® Android® browser, RIM BlackBerry® Browser, Apple® Safari®, Palm® Blazer, Palm® WebOS® Browser, Mozilla® Firefox® for mobile, Microsoft® Internet Explorer® Mobile, Amazon® Kindle® Basic Web, Nokia® Browser, Opera Software® Opera® Mobile, and Sony® PSP™ browser.

Software Modules

In some embodiments, the platforms, systems, media, and methods disclosed herein can include software, server, and/or database modules, or use of the same. In view of the disclosure provided herein, software modules can be created by techniques known to those of skill in the art using machines, software, and languages known to the art. The software modules disclosed herein can be implemented in a multitude of ways. In various embodiments, a software module comprises a file, a section of code, a programming object, a programming structure, or combinations thereof. In further various embodiments, a software module comprises a plurality of files, a plurality of sections of code, a plurality of programming objects, a plurality of programming structures, or combinations thereof. In various embodiments, the one or more software modules can comprise, by way of non-limiting examples, a web application, a mobile application, and a standalone application. In some embodiments, software modules can be in one computer program or application. In other embodiments, software modules can be in more than one computer program or application. In some embodiments, software modules can be hosted on one machine. In other embodiments, software modules can be hosted on more than one machine. In further embodiments, software modules can be hosted on cloud computing platforms. In some embodiments, software modules can be hosted on one or more machines in one location. In other embodiments, software modules can be hosted on one or more machines in more than one location.

Databases

In some embodiments, the platforms, systems, media, and methods disclosed herein can include one or more databases, or use of the same. In view of the disclosure provided herein, those of skill in the art will recognize that many databases are suitable for storage and retrieval of information. In various embodiments, suitable databases can include, by way of non-limiting examples, relational databases, non-relational databases, object oriented databases, object databases, entity-relationship model databases, associative databases, and XML databases. Further non-limiting examples include SQL, PostgreSQL, MySQL, Oracle, DB2, and Sybase. In some embodiments, a database is internet-based. In further embodiments, a database can be web-based. In still further embodiments, a database can be cloud computing-based. In other embodiments, a database can be based on one or more local computer storage devices.

EXAMPLES

Figure 11:
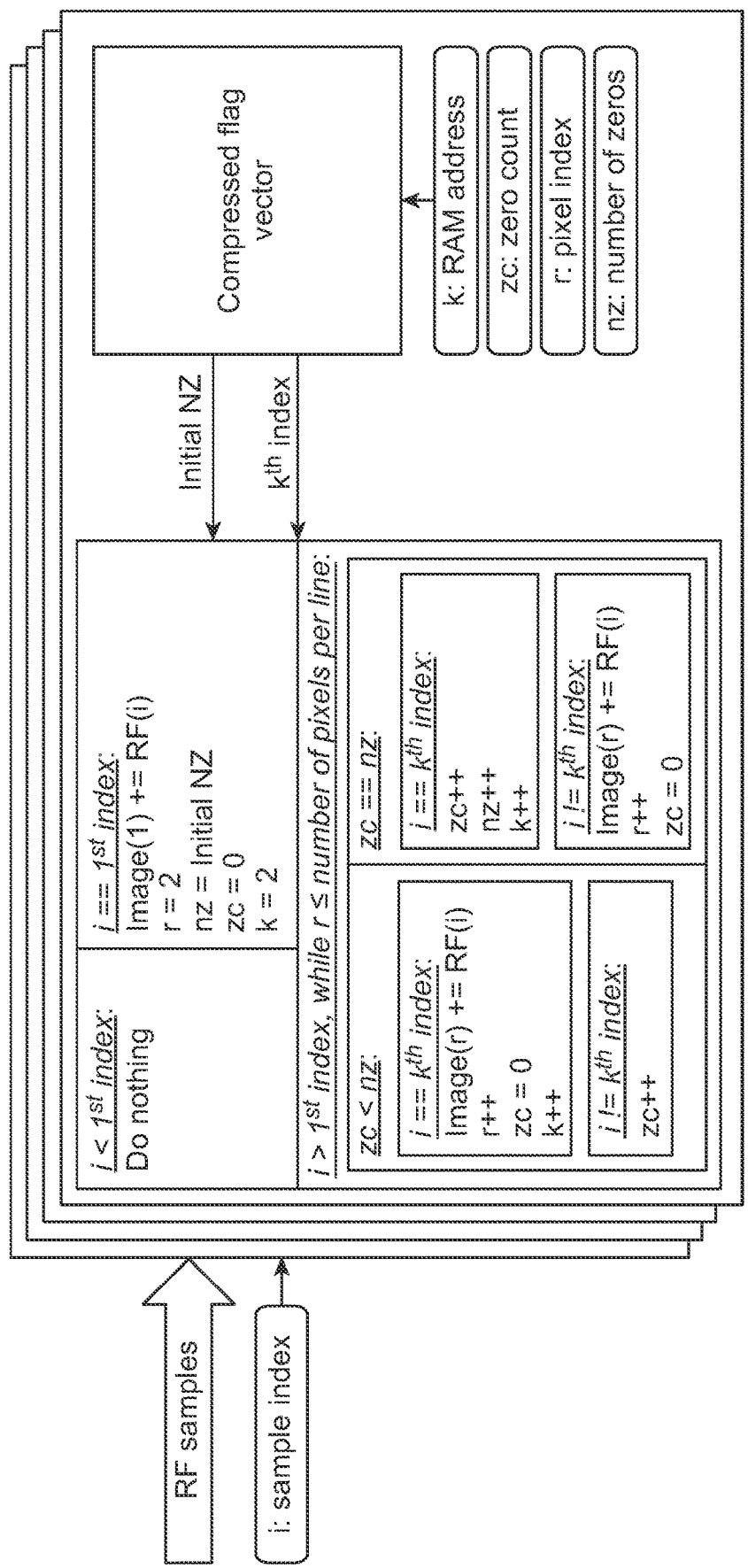
FIG. 11 shows example pseudocode for implementing flag table based ultrasound beamforming.

FIG. 11 shows example pseudocode for implementing flag table based ultrasound beamforming with a compressed flag table. The pseudocode utilizes variables k (corresponding to a RAM address), zc (corresponding to a counter of the number of adjacent 0-flags counted), r (corresponding to a pixel index), and nz (corresponding to expected number of zeros to be encountered between two 1-flags). The variable nz corresponds to the value NZ described herein. The pseudocode can process RF samples and can utilize an index i corresponding to the current index of each RF sample. The pseudocode can perform real-time decompression of the compressed flag table to select which RF samples are to be used to reconstruct an image.

When the RF sample index i is smaller than the $1^{st}$ RF sample index, the pseudocode does nothing. When the RF sample index i is made equal to the $1^{st}$ RF sample index, the pseudocode adds the value of the RF sample to a first pixel in an array of image pixels. The pseudocode then increments r to move to the next pixel. The pseudocode resets the value of the counter zc to 0. The pseudocode increments the value of k to a second RAM address.

For values of i greater than the $1^{st}$ RF sample index, the pseudocode compares zc to nz. When zc is smaller than nz and i is equal to $k^{th}$ RF sample index stored in the compressed flag table, an unexpected 1-flag has been encountered, and the pseudocode adds the value of the RF sample to the $r^{th}$ pixel in an array of image pixels. The pseudocode then increments r to move to the next pixel and resets the value of the counter zc to 0. The pseudocode increments the value of k to the next RAM address (corresponding to the next RF sample index that does not match the expected flag pattern). When zc is smaller than nz and i is not equal to $k^{th}$ RF sample index stored in the compressed flag table, an expected 0-flag has been encountered, and the pseudocode increments zc.

When zc is equal to nz and i is equal to $k^{th}$ RF sample index stored in the compressed flag table, an unexpected 0-flag has been encountered, and the pseudocode increments zc, nz, and k. When zc is equal to nz and i is not equal to $k^{th}$ RF sample index stored in the compressed flag table, an expected 1-flag has been encountered, and the pseudocode adds the value of the RF sample to the $r^{th}$ pixel in an array of image pixels. The pseudocode then increments r to move to the next pixel and resets the value of the counter zc to 0.

Figure 12:
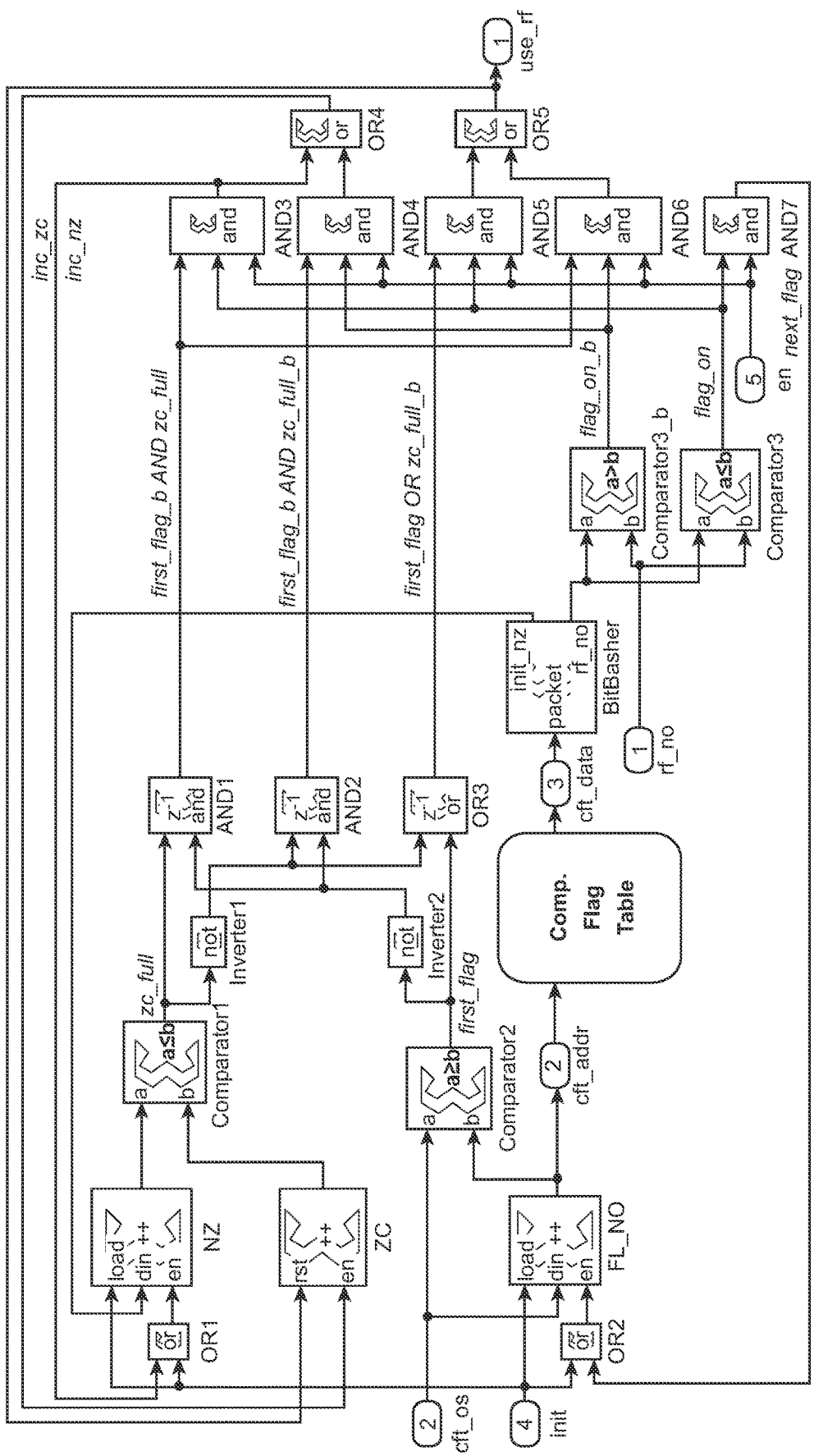
FIG. 12 shows example circuitry for implementing flag table based ultrasound beamforming.

FIG. 12 shows example circuitry for implementing flag table based ultrasound beamforming with a compressed flag table. The circuitry comprises a compressed flag table (CFT), OR gates (OR1, OR2, OR3, OR4, and OR5), counters (ZC, NZ, and FL_NO), comparators (Comparator1, Comparator2, Comparator3, and Comparator 3b), NOT gates (Inverter1 and Inverter2), AND gates (AND1, AND2, AND3, AND4, AND5, AND6, AND7), and a BitBasher. The circuitry depicted in FIG. 12 is a direct implementation of the pseudocode described in FIG. 11 followed by logic reduction. Hence, the circuitry depicted in FIG. 12 may perform an identical functionality as the pseudocode described in FIG. 11, namely, implementing flag table based ultrasound beamforming with a compressed flag table.

Figure 13:
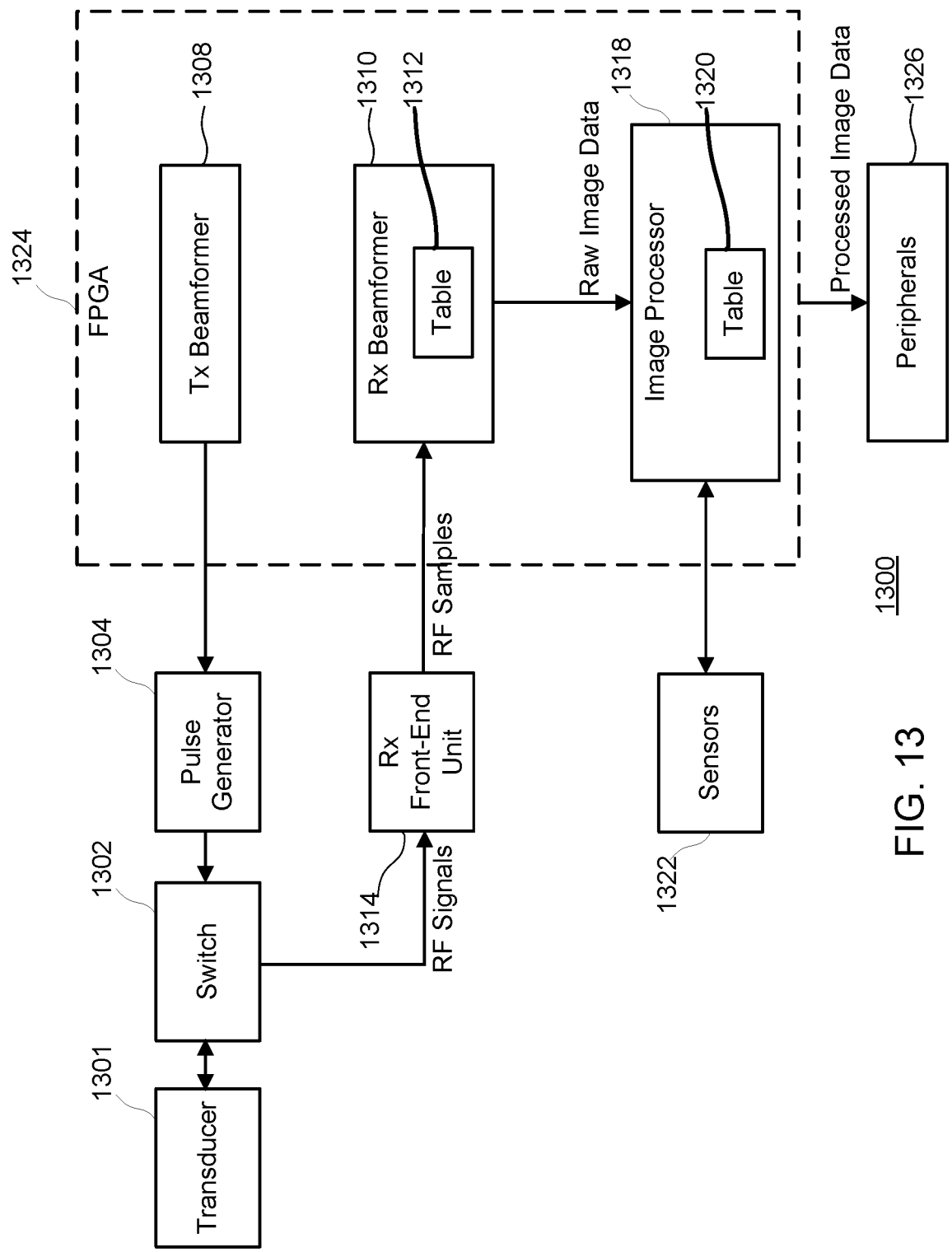
FIG. 13 illustrates a block diagram of an ultrasound imaging device used to image a region of interest.

FIG. 13 illustrates a block diagram of an example ultrasound device 1300, which may be used for some implementations described herein. For example, ultrasound device 1300 may be used to implement ultrasound device 100 of FIG. 1. In some implementations, ultrasound device 1300 includes a transducer array 1301, a switch 1302, and a pulse generator 1304. Transducer array 1301 may also be referred to as transducer 1301. Ultrasound device 1300 may include a transmit (Tx) beamformer 1308 and/or a receive (Rx) beamformer 1310. Rx beamformer 1310 may include a memory that stores a table 1312. Ultrasound device 1300 may include an Rx front-end unit 1314 and/or an image processor 1318. In some implementations, ultrasound device 1300 also includes sensors 1322 and/or peripherals 1326.

In some implementations, a table 1312 may be stored on FPGA 1324, or stored on any other suitable storage device. Furthermore, in various implementations, FPGA 1324 may not have all of the components shown and/or may have other elements including other types of elements instead of, or in addition to, those shown herein. For example, in some implementations, FPGA 1324 may include image processor 1318. Furthermore, while image processor 1318 is described herein as performing separate functions, in some implementations, a single processing unit such as FPGA 1324 may perform all of the functions and implementations described herein.

For ease of illustration, FIG. 13 shows one block for each of components of ultrasound device 1300. In other implementations, ultrasound device 1300 may not have all of the components shown and/or may have other elements including other types of elements instead of, or in addition to, those shown herein.

In operation, Tx beamformer 1308 causes pulse generator 1304 to generate electrical signals based on transmit beamforming, where the electrical signals are applied to transducer array (or "transducer") 1301. The electrical signals or pulses may be produced at a predetermined pulse rate (e.g., 1,000 pulses per second, etc.), depending on the particular implementation. The switch 1302 may select one of two operating modes: (1) select the signal in the direction from the pulse generator 1304 to the transducer 1301 or (2) select the signal in the direction from the transducer 1301 to the Rx front-end unit 1314.

In various implementations, pulse generator 1304 controls the amplitude of the electrical signals or pulses, which in turn controls the intensity and energy of an ultrasound beam produced by transducer array 1301, after the signal is selected in the direction from the pulse generator 1304 to the transducer array 1301 by the switch 1302. Pulse generator 1304 may also control the width of the pulses (which in turn controls the signal frequency) and the number of cycles in the pulses (which in turn controls the energy and the bandwidth of the signal).

Transducer array 1301 may generate ultrasonic waves based on the electrical signals received from pulse generator 1304. The ultrasonic waves may also be referred to as ultrasound waves, ultrasonic pulses, or ultrasound pulses.

In various implementations, transducer array 1301, also referred to as a transducer or probe, is positioned in direct contact with a surface such as the body of a patient (e.g., the abdomen of a patient). In some implementations, the probe need not be in direct contact with the surface. For example, there may be water or another medium between the probe and the surface. In some implementations, when the probe is in direct contact with the surface, an ultrasound gel may be used to couple the probe with the surface. Transducer array 1301 may focus a beam of ultrasonic waves or pulses to give the beam a particular size and shape at various depths within a particular space/area beneath the surface (e.g., a portion of patient's body). Transducer array 1301 may also scan the beam over the space that is being imaged (e.g., over an anatomical area). The space that is being imaged may also be referred to as a region of interest.

In various implementations, transducer array 1301 includes one or more transducer elements. In various implementations, the particular type of transducer elements may vary, depending on the particular implementation. For example, the transducer elements may be piezoelectric transducer elements, capacitive transducer elements, etc. When an electrical pulse is applied to a given transducer element, the transducer element vibrates and produces the ultrasound, or ultrasonic wave, which is directed at the region of interest. Conversely, when a given transducer element is vibrated by returning ultrasound echoes from objects in the region of interest, the transducer element produces radio frequency (RF) signals.

When transducer array 1301 receives reflected ultrasonic waves (e.g., from objects in the region of interest), transducer array 1301 may generate RF signals based on the reflected ultrasonic waves. The reflected ultrasonic waves may also be referred to as ultrasonic echoes, or ultrasound echoes, or echoes. The RF signals may also be referred to as raw RF data.

In some implementations, Rx front-end unit 1314 amplifies and digitizes the RF signals from transducer array 1301 (after the signal is selected in the direction from the transducer 1301 to the Rx front-end unit 1314 by the switch 1302) to provide RF samples, and sends the RF samples to Rx beamformer 1310. The RF samples may also be referred to as digitized RF signals. In some implementations, Rx front-end unit 1314 amplifies and/or filters the RF signals before digitizing them. In some implementations, the amplifier gain of Rx front-end unit 1314 may vary over time, in order to compensate for ultrasound attenuation.

In various implementations, Rx beamformer 1310 generates raw image data based on the RF samples and performs beamforming functions in order to generate the raw image data. In some implementations, Rx beamformer 1310 creates an intensity map of the reflected ultrasonic waves corresponding to every point in the field of view of region of interest 202. Rx beamformer 1310 may map the received (e.g., time-domain) signal to a location in an image and coherently sums the signals from all transducer elements for every point in the field of view.

In various implementations, Rx beamformer 1310 determines which of the RF samples are to be used to generate raw image data based on table 1312. As described in more detail herein, in various implementations, table 1312 indicates which RF samples are to be used to generate raw image data and which RF samples are not to be used to generate raw image data.

In various implementations, table 1312 is predetermined in that information in table 1312 is generated prior to an imaging session, and table 1312 is pre-loaded in Rx beamformer 1310 or in any other suitable storage location. Table 1312 may also be referred to as predetermined table 1312. During runtime, Rx beamformer 1310 checks table 1312 during an imaging session in order to determine which RF samples to use to generate raw image data. In various implementations, Rx beamformer 1310 generates raw image data based on the RF samples that are to be used to generate raw image data, and then sends the raw image data to image processor 1318.

As indicated herein, image processor 1318 processes the raw image data to provide the processed image data. The processed image data may be referred to as post-processed image data. The processed image data may in turn be used to provide ultrasound images.

As described in more detail herein, in various implementations, image processor 1318 may determine input values based on the raw image data from Rx beamformer 1310. Image processor 1318 may determine output values based on the input values and a table 1320 (e.g., by using a compression circuitry). In various implementations, image processor 1318 compresses the raw image data such that the dynamic range of the processed image data is smaller than the dynamic range of the raw image data.

In various implementations, table 1320 is predetermined in that information in table 1320 is generated prior to an imaging session, and table 1320 is pre-loaded in image processor 1318 or in any other suitable storage location. Table 1320 may also be referred to as predetermined table 1320. During runtime, image processor 1318 may check table 1320 during an imaging session in order to determine the output values used to generate processed image data. Various implementations of table 1320 are described in more detail herein.

In various implementations, sensors 1322 may include position sensors, rotational sensors, tilt sensors, gyroscopes, accelerometers, etc., for positioning ultrasound device 1300. In some implementations, the position sensors and rotational sensors may be integrated.

mined number of dynamic subranges span the dynamic range of input values (e.g., $[0, (2^{31}-1)]$ and $[2^{31}, (2^{32}-1)]$ for a 32-bit input and 2 dynamic subranges).

The image processor 1318 may determine output values based on the dynamic subranges in which the input values fall. As described in more detail herein, in some implementations, there may be 256 dynamic subranges into which one or more input values may fall. Depending on the selection of compression function, a given dynamic subrange may contain no input values. Each output value is one of 256 output values (e.g., integers from 0 to 255), where each output value corresponds to one of the 256 dynamic subranges.

For example, if there are 32 input bits and 8 output bits, an example compression function may be $f(x)=8 \log_2(x+1)-1$. This will map an input value of $2^{32}-1$ ($FFFFFFFF_{16}$) to an output value of 255. Setting the output value to 1 and solving for x, we observe that the first threshold value for such a compression function may be 1 (e.g., 0.19 rounded up to the nearest integer value). The second threshold value may be calculated by setting the output value to 2 and solving for x, and so on to generate the entire set of threshold values. Each dynamic subrange may be defined by a range of integers between two successive threshold values. Examples of dynamic subranges and output values are listed in Table 1 below.

TABLE 1

| Dynamic Subrange (Lower Bound) | 0 ($00000000_{16}$) | 14 | 234 | 60,096 | 3,938,502,375 |
|---|---|---|---|---|---|
| Dynamic Subrange (Upper Bound) | 1 ($00000001_{16}$) | $2^4-1$ (15) ($0000000F_{16}$) | $2^8-1$ (255) ($000000FF_{16}$) | $2^{16}-1$ (65,535) ($0000FFFF_{16}$) | $2^{32}-1$ (4,294,967,295) ($FFFFFFFF_{16}$) |
| Output Value | 1 | 31 | 63 | 127 | 255 |

In various implementations, peripherals 1326 may include one or more display devices and/or may send processed image data to remote display devices (e.g., a 2D display, a 3D display, a printer, a wearable device, an augmented-reality glass, a virtual-reality glass, etc.). Remote display devices may include stand-alone computers, tablet computers, smartphones, dedicated monitors, etc. In some implementations, peripherals 1326 may also include an electrocardiograph (ECG or EKG device), pulse oximeter, position tracker, needle guide, etc.

Image processor 1318 may perform various operations to generate processed image data, e.g., image compression. This generation may be based on raw image data received from Rx beamformer 1310 in order to provide ultrasound images. In various implementations, to process the raw image data to provide processed image data, image processor 1318 compresses the raw image data such that the dynamic range of the processed image data is smaller than the dynamic range of the raw image data.

An image compression method is initiated when image processor 1318 determines input values based on raw image data from Rx beamformer 1310, where the input values fall within a dynamic range of input values (e.g., $[0, (2^{32}-1)]$ for a 32-bit input). In some implementations, the dynamic range of input values includes dynamic subranges. In some implementations, the dynamic range of input values may have a predetermined number of dynamic subranges (e.g., 2, 4, 8, 16, 32, 64, 128, 256, 512, etc.). The dynamic subranges may be a set of intervals (e.g., unequally spaced, equally spaced, or approximately equally spaced) such that the predeter- As such, the overall dynamic range of input values is compressed or reduced to a smaller dynamic range of output values. One benefit of a smaller dynamic range of output values is that the number of bits representing input values is reduced to a smaller number of bits representing output values, thereby compressing the data and reducing the memory requirements. Various implementations directed to image processor 1318 determining output values are described in more detail herein.

As described in more detail herein, image processor 1318 provides the processed image data, which may be high-quality image data, yet with a decreased dynamic range. Image processor 1318 may then send the processed image data to a display device to display an ultrasound image to a user.

The image processor 1318 may generate the processed image data based on the output values. The processed image data may be the output values (e.g., pixel data). The processed image data may be generated based on the output values (e.g., by contrast enhancement or other image processing techniques prior to displaying the image data). Various implementations directed to image processor 1318 generating the processed image data based on the output values are described in more detail herein.

Figure 14:
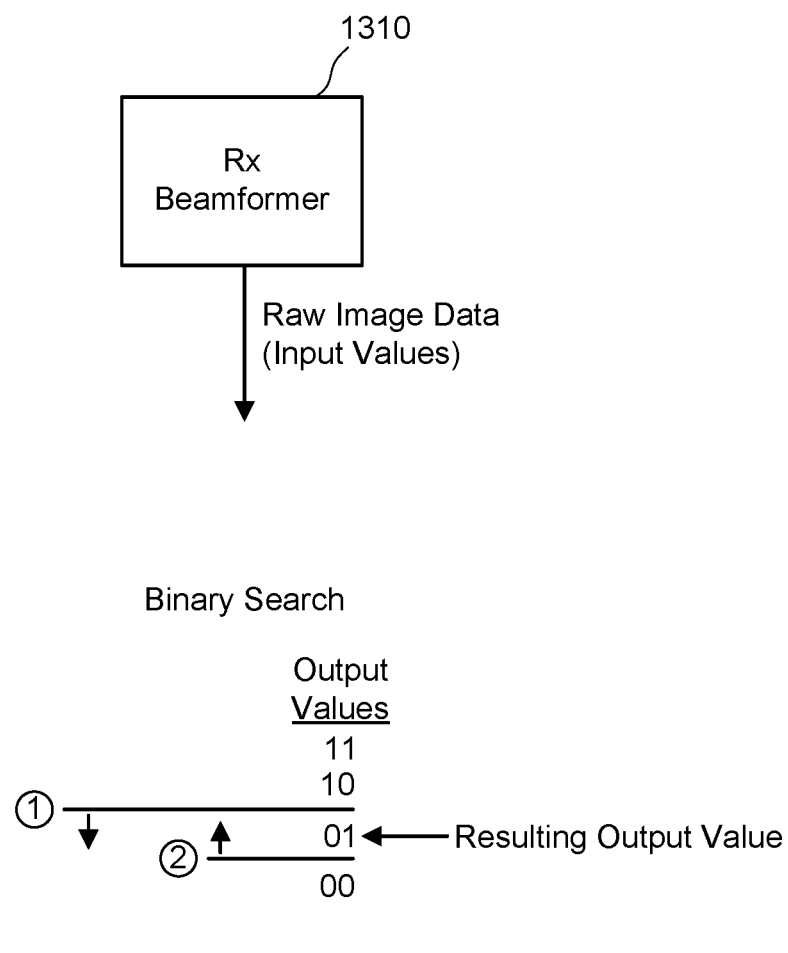
FIG. 14 illustrates an example block diagram for performing a binary search.

FIG. 14 illustrates an example block diagram for performing a binary search, according to some implementations. As shown, Rx beamformer 1310 provides raw image data, which includes input values, to image processor 1318.

In various implementations, to generate processed image data, image processor 1318 performs a binary search, where the binary search identifies a dynamic subrange for each input value, and maps the input values to the output values based on the dynamic subranges. In other words, in various implementations, multiple input values map to a single dynamic subrange, and each dynamic subrange maps to a single output value. As such, one or more of the input values are associated with a single output value. Stated differently, each output value is associated with one or more input values (or in some cases, possibly no input values).

In some implementations, image processor 1318 takes each input number and compares each to different subdynamic range thresholds in order to determine in which subdynamic range each input number falls, where each dynamic subrange maps to a particular output value.

Referring still to FIG. 14, for each input value, image processor 1318 compares the input value to a first threshold value at a first stage (indicated with a circled '1' in FIG. 14). In this particular simplified example, the possible output values are 00, 01, 10, and 11. In this example, the input value is less than the first threshold value, which narrows the possible output values to 00 and 01. Image processor 1318 then compares the input value to a second threshold value at a second stage. In this example, the input value is greater than the second threshold value, which narrows the possible output values to 01. As such, the resulting output value is 01. The threshold values may be calculated as described elsewhere herein.

In this simplified example, the output values are 2-bit values. As such, there are 2 stages where each input value is compared against 2 threshold values. The particular number of bits may vary, depending on the particular implementations. For example, there may be 8-bit output values, in which case there may be 8 stages where each input value is compared against 8 threshold values. In some implementations, the number of output values is limited to 256 output values (e.g., 0 to 255).

In various implementations, the compression function being implemented is such that the output values monotonically increase relative to the input values. In other words, a range of smaller input values corresponds to a smaller output value, and a range of larger input values corresponds to a larger output value. In some implementations, the output values may monotonically decrease relative to the input values. The monotonicity of the compression function may enable a recursive binary search method to be performed with a lookup table, as described elsewhere herein.

Figure 15A:
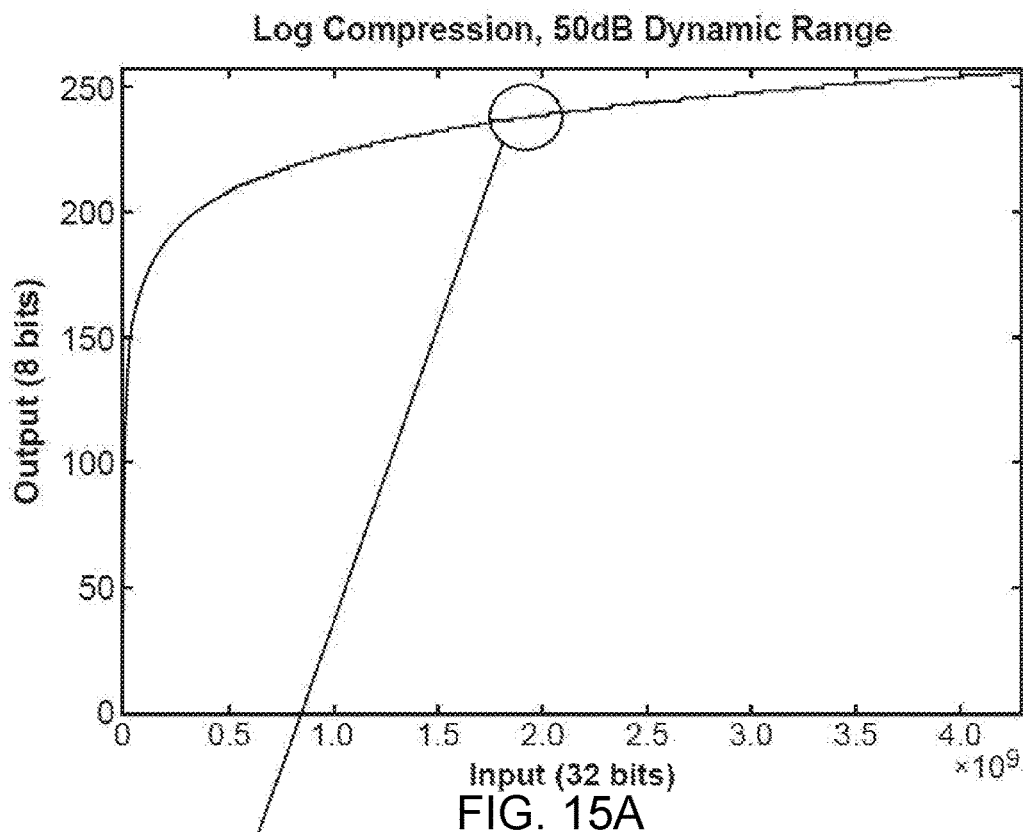
FIG. 15A shows an example of a log compression curve applied on input words of 32-bit length to obtain output words of 8-bit length.
Figure 15B:
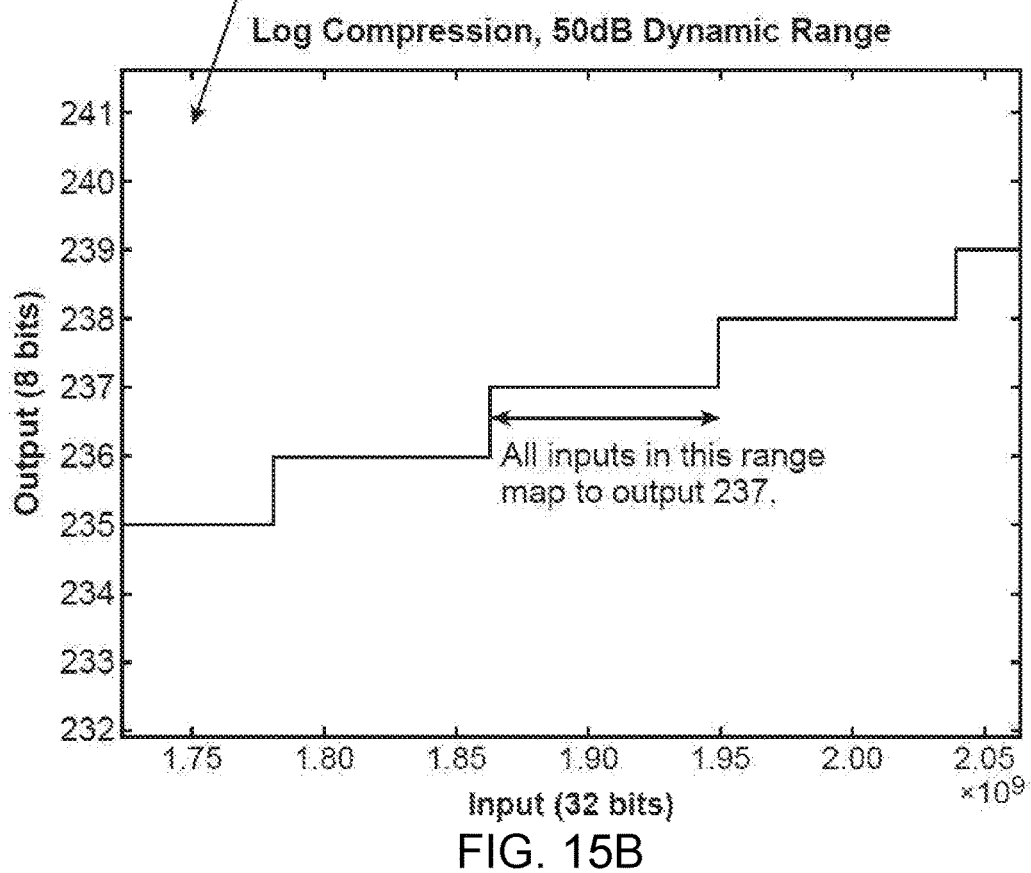
FIG. 15B shows an example of a zoomed-in portion of the log compression curve of FIG. 15A showing discrete output values corresponding to ranges of input values.

FIGS. 15A and 15B illustrate an example of a log (logarithmic) compression curve, which may be used for some embodiments described herein. A log compression curve is used to illustrate an example of a compression curve that may be used for dynamic range compression. In general, the compression curve may be any curve that monotonically increases or decreases over a given range of input values. The number of output bits may be less than the number of input bits.

FIG. 15A shows an example of a log compression curve applied on input words of 32-bit length to obtain output words of 8-bit length. In this example, the input words may be 32-bit length unsigned integers, and may range in value from $00000000_{16}$ (where the 16 subscript indicates values in hexadecimal or base 16) to $FFFFFFFF_{16}$ (or $2^{32}-1=4.29\times10^9$). The output values may be 8-bit length unsigned integers, and may range in value from $00_{16}$ to $FF_{16}$ (or $2^8-1=255$). For example, for this log compression function, a 32-bit input value of $00000000_{16}$ would map to an 8-bit output value of $00_{16}=00000000_2$ (where the 2 subscript indicates values in binary or base 2), and a 32-bit input value of $FFFFFFFF_{16}$ would map to an 8-bit output value of $FF_{16}=11111111_2$. Since the size of the range of input values is about $2^{32-8}=1.68\times10^7$ times the size of the range of output values, there may be many input values (e.g., integers) that map to the same given output value (e.g., integers).

FIG. 15B shows an example of a zoomed-in portion of the log compression curve showing discrete output values corresponding to ranges of input values. This zoomed-in portion shows a range of input values of approximately $1.7\times10^9$ to $2.06\times10^9$ and a range of output values of approximately 232 to 242. In this range of log compression function values, each of five contiguous and mutually exclusive ranges of input values maps to one of five discrete possibilities of output values (235, 236, 237, 238, and 239). For example, all inputs in the range indicated by the double-arrowed line segment (in red) map to an output value of 237. This range can be represented by two threshold values, such that all input values between these two threshold values (e.g., greater than or equal to the smaller threshold value among the pair of threshold values, and less than the larger threshold value among the pair of threshold values) map to the same output value. Hence, a log compression function reduces the number of bits needed to represent an input value (e.g. 32 bits) by mapping said input value to an output value with fewer bits (e.g. 8 bits).

After a compression function has been used to map each of one or more input values (with a number of input bits m) to a corresponding output value (with a number of output bits n), where n<m, a look-up table may store the ($2^n-1$) input threshold values (e.g., th{1}, th{2}, ..., th{$2^n-1$}) corresponding to the $2^n$ possible output values. The first (e.g., smallest) of the possible output values may correspond to all input values less than th{1} (e.g., the first threshold value among the set of input threshold values). The second (e.g., second smallest) of the possible output values may correspond to all input values between th{1} and th{2} (e.g., greater than or equal to th{1}, and less than th{2}). In general, the $i^{th}$ (e.g., $i^{th}$ smallest) of the possible output values may correspond to all input values between th{i−1} and th{i} (e.g., greater than or equal to th{i−1}, and less than th{i}). The largest of the possible output values may correspond to all input values greater than or equal to th{$2^n-1$}. The size of the lookup table may be m·($2^n-1$) bits. The set of threshold values may be generated using a compression function (e.g., a log compression function).

The particular number of bits may vary, depending on the particular implementations. For example, there may be 8-bit output values, in which case there may be 8 stages where each input value is compared against 8 threshold values. In some implementations, the number of output values is limited to 256 output values (e.g., 0 to 255).

As described herein, in various implementations, generation of the processed image data may be based on a predetermined table, such as table 1320 (e.g., a lookup table). For example, the processed image data may be based on output values determined from table 1320, where image processor 1318 may determine the output values based on the input values, or dynamic subranges into which the input values fall.

In various implementations, the predetermined table includes predetermined thresholds associated with the dynamic subranges. In various implementations, the predetermined table maps input values to the output values based on the predetermined thresholds. In some implementations, each output value is associated with a unique dynamic subrange. For example, in some implementations, table 1320 may store ($2^n-1$) input threshold values (e.g., th $\{1\}, \ldots, \text{th}\{2^n-1\}$), where table 1320 may have a size of $m \cdot (2^n-1)$ bits, and where n is the number of output bits and m is the number of input bits.

The lookup table may be used to find a function output value ("output"), given an input value ("input"), as follows. If input $< \text{th}\{1\}$, the output is 0. If input is greater than or equal to $\text{th}\{2^n-1\}$, the output is $(2^n-1)$. If input is between $\text{th}\{i\}$ and $\text{th}\{i+1\}$ (e.g., greater than or equal to $\text{th}\{i\}$, and less than $\text{th}\{i+1\}$), the output is i. This procedure of finding a function output value given an input value, using a lookup table, may be referred to as "performing a lookup" in a lookup table.

Figure 16:
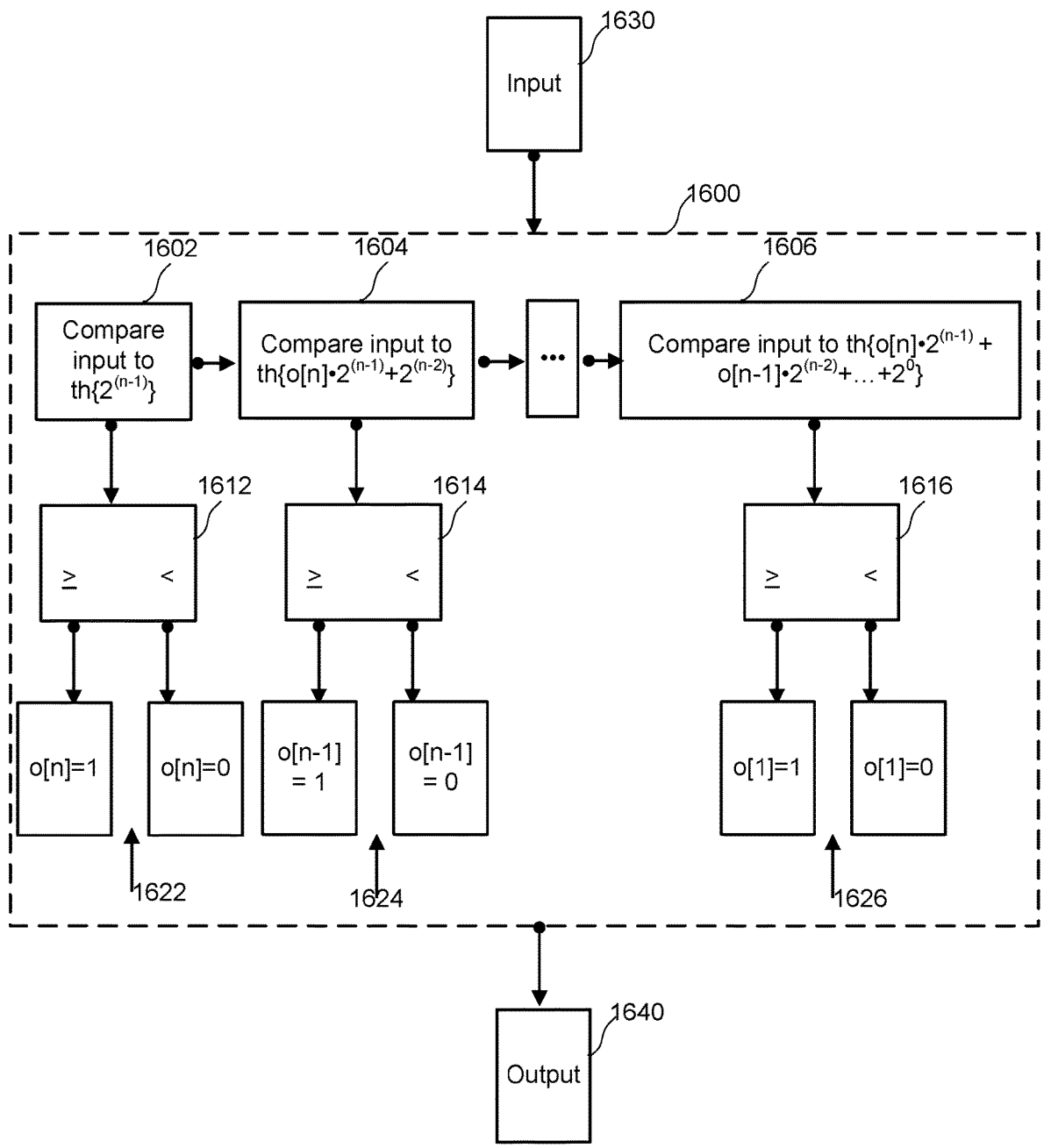
FIG. 16 illustrates a recursive binary search method to determine output values based on threshold values in a lookup table.

FIG. 16 illustrates a recursive binary search method to determine output values based on threshold values in a lookup table, which may be used for some embodiments described herein. This recursive binary search method may be performed by an apparatus to perform a lookup in a lookup table by generating the n bits of an output given an input. The binary search identifies a dynamic subrange for each input value, and maps the input values to the output values based on the dynamic subranges. In other words, in various implementations, multiple input values map to a single dynamic subrange, and each dynamic subrange maps to a single output value. As such, one or more of the input values are associated with a single output value. Stated differently, each output value is associated with one or more input values (or in some cases, possibly no input values). This binary search may comprise taking each input number and comparing said input number to different subdynamic range thresholds in order to determine in which subdynamic range each input number falls, where each dynamic subrange maps to a particular output value. Other types of search methods may be used to identify threshold values with a lookup table, e.g. a linear search.

As shown in FIG. 16, the recursive binary search method 1600 may be performed as follows. In each of n stages of the recursive binary search method 1600, given an input value (or "input") 1630, one bit of the n bits that comprise the output value (or "output") 1640 may be generated (e.g., beginning with the most significant bit (MSB) of the output value (o[n]) in the first stage of the n stages, and ending with the least significant bit (LSB) of the output value (o[1]) in the nth stage of the n stages (the final stage)). Each stage may comprise a comparison step and a bit assignment step.

At step 1602, in the first stage of the recursive binary search method, the input 1630 is compared to $\text{th}\{2^{(n-1)}\}$. At comparison step 1612, a comparison is performed (e.g., using one or more comparators) to determine whether (1) the first value is greater than or equal to the second value or (2) the first value is less than the second value. At bit assignment step 1622, the comparison of comparison step 1612 determines a first bit of the n bits to be assigned to the output value 1640. If the input 1630 is greater than or equal to $\text{th}\{2^{(n-1)}\}$ (e.g., case (1) of comparison step 1612), the most significant bit (MSB) of the output (o[n]) is set to 1 (e.g., o[n]=1). If the input 1630 is less than $\text{th}\{2^{(n-1)}\}$ (e.g., case (2) of comparison step 1612), the MSB of the output (o[n]) is set to 0 (e.g., o[n]=0).

At step 1604, in the second stage of the recursive binary search method, the input is compared to $\text{th}\{o[n] \cdot 2^{(n-1)} + 2^{(n-2)}\}$. At comparison step 1614, a comparison is performed (e.g., using one or more comparators) to determine whether (1) the first value is greater than or equal to the second value or (2) the first value is less than the second value. At bit assignment step 1624, the comparison of step 1614 determines a second bit of the n bits to be assigned to the output value 1640. If the input 1630 is greater than or equal to $\text{th}\{o[n] \cdot 2^{(n-1)} + 2^{(n-2)}\}$ (e.g., case (1) of comparison step 1614), the second MSB of the output (o[n-1]) is set to 1 (e.g., o[n-1]=1). If the input 1630 is less than $\text{th}\{o[n] \cdot 2^{(n-1)} + 2^{(n-2)}\}$ (e.g., case (2) of comparison step 1614), the second MSB of the output (o[n-1]) is set to 0 (e.g., o[n-1]=0).

Similarly to the performing of the first two stages, in the third stage of the recursive binary search method, the input is compared to $\text{th}\{o[n] \cdot 2^{(n-1)} + o[n-1] \cdot 2^{(n-2)} + 2^{(n-3)}\}$. At the third comparison step, a comparison is performed (e.g., using one or more comparators) to determine whether (1) the first value is greater than or equal to the second value or (2) the first value is less than the second value. At the third bit assignment step, this comparison determines a third bit of the n bits to be assigned to the output value 1640. If the input 1630 is greater than or equal to $\text{th}\{o[n] \cdot 2^{(n-1)} + o[n-1] \cdot 2^{(n-2)} + 2^{(n-3)}\}$ the third MSB of the output (o[n-2]) is set to 1 (e.g., o[n-2]=1). If the input 1630 is less than $\text{th}\{[o[n] \cdot 2^{(n-1)} + o[n-1] \cdot 2^{(n-2)} + 2^{(n-3)}\}$, the third MSB of the output (o[n-2]) is set to 0 (e.g., o[n-2]=0).

This recursive binary search method may repeat for all n stages until all n bits of the output value 1640 are calculated. At step 1606, in the nth stage of the recursive binary search method, the input is compared to $\text{th}\{[o[n] \cdot 2^{(n-1)} + o[n-1] \cdot 2^{(n-2)} + \ldots + 2^{0}\}$. At comparison step 1616, a comparison is performed (e.g., using one or more comparators) to determine whether (1) the first value is greater than or equal to the second value or (2) the first value is less than the second value. At bit assignment step 1626, the comparison of comparison step 1616 determines an nth bit (e.g., the least significant bit (LSB)) of the n bits to be assigned to the output value 1640. If the input 1630 is greater than or equal to $\text{th}\{[o[n] \cdot 2^{(n-1)} + o[n-1] \cdot 2^{(n-2)} + \ldots + 2^{0}\}$ (e.g., case (1) of comparison step 1616), the LSB of the output (o[1]) is set to 1 (e.g., o[1]=1). If the input 1630 is less than $\text{th}\{[o[n] \cdot 2^{(n-1)} + o[n-1] \cdot 2^{(n-2)} + \ldots + 2^{0}\}$ (e.g., case (2) of comparison step 1616), the LSB of the output (o[1]) is set to 0 (e.g., o[1]=0). In this manner, each successive stage of the recursive binary search method may generate a successive bit of the output 1640, and performing all n stages of the recursive binary search method 1600 may generate all n bits of the output value 1640.

Although FIG. 16 shows a recursive binary search method in accordance with an embodiment, a person of ordinary skill in the art will recognize many adaptations and variations. For example, the steps can be performed in any order. Some of the steps may be removed, some of the steps can be repeated, and additional steps can be performed.

In some implementations, the stages of the binary search are performed in series and form a serialized pipeline such that the incoming stream of input values is accepted at a constant rate. In various implementations, no buffer for the incoming input values is required. Once a particular input value passes from the first stage to the second stage, the next input value may come into the first stage. Such pipelining may occur at each stage.

TABLE 2

| Stage Number | Threshold Values Needed | Concatenated Stages for Output |
|---|---|---|
| 1st | $\text{th}\{2^{(n-1)}\}$ <br> ($\text{th}\{1000 \ldots 00'b\}$) | |
| 2nd | $\text{th}\{2^{(n-2)}\}$ <br> $\text{th}\{2^{(n-1)} + 2^{(n-2)}\}$ <br> ($\text{th}\{X100 \ldots 00'b\}$) | where X is the comparator output of the first stage |

TABLE 2-continued

| Stage Number | Threshold Values Needed | Concatenated Stages for Output |
|---|---|---|
| $3^{rd}$ | th$\{$XX10 ... 00'b$\}$ | XX is the concatenated output of the first two comparators |
| ... | ... | ... |
| nth | th$\{$XXXX ... X1'b$\}$ | XXXX ... X is the concatenated output of all the previous comparators |

Table 2 illustrates a method to perform lookup table segmentation, which may be used for some embodiments described herein. The lookup table may be divided in n sub-tables for the n stages. For example, for an 8-bit output function, table 1320 may be divided into 8 sub-tables in an 8-stage implementation. The table data needed in the individual stages of the recursive binary search method may be mutually exclusive. For example, only th$\{2^{(n-1)}\}$ is needed in the first stage, e.g. to generate the MSB of the output value (e.g., in binary, th$\{1000 \ldots 00'b\}$). Only th$\{2^{(n-2)}\}$ and th$\{2^{(n-1)}+2^{(n-2)}\}$ are needed in the second stage (e.g., in binary, th$\{X100 \ldots 00'b\}$, where X is the comparator output of the first stage). Only th$\{XX10 \ldots 00'b\}$ are needed in the third stage, where XX is the concatenated output of the first two comparators. This reasoning can be applied to each successive stage, until only th$\{XXXX \ldots X1'b\}$ are needed in the last stage, where XXXX ... X is the concatenated output of all the previous comparators. The address to the sub-table may be the concatenated comparator output of all the previous stages. Further, the final output of the function may be the concatenated output of all n comparators.

In various implementations, image processor 1318 functions as a compression module, where the number of output values may be limited to a predetermined number of output values (e.g., 256 output values ranging from 0 to 255, etc.).

In various implementations, image processor 1318 converts the input values of the raw image data to a grayscale range, where image processor 1318 associates the output values with shades of gray for display. In some implementations, the input values fall within a first dynamic range, and the output values fall within a second dynamic range, which is smaller than the first dynamic range. For example, the raw image data may provide an image that includes 14 bits or 16 bits per pixel. Image processor 1318 compresses the raw image data and generates an image that is 8 bits per pixel, which provides 256 different shades of gray.

Although the steps, operations, or computations may be presented in a specific order, the order may be changed in particular implementations. Other orderings of the steps are possible, depending on the particular implementation. In some particular implementations, multiple steps shown as sequential in this specification may be performed at the same time. Also, some implementations may not have all of the steps shown and/or may have other steps instead of, or in addition to, those shown herein.

Implementations described herein provide various benefits. For example, implementations provide processed image data that is high-quality and that comprises pixels having compressed dynamic range. Implementations provide a compressed dynamic range without compromising spatial resolution.

Figure 17:
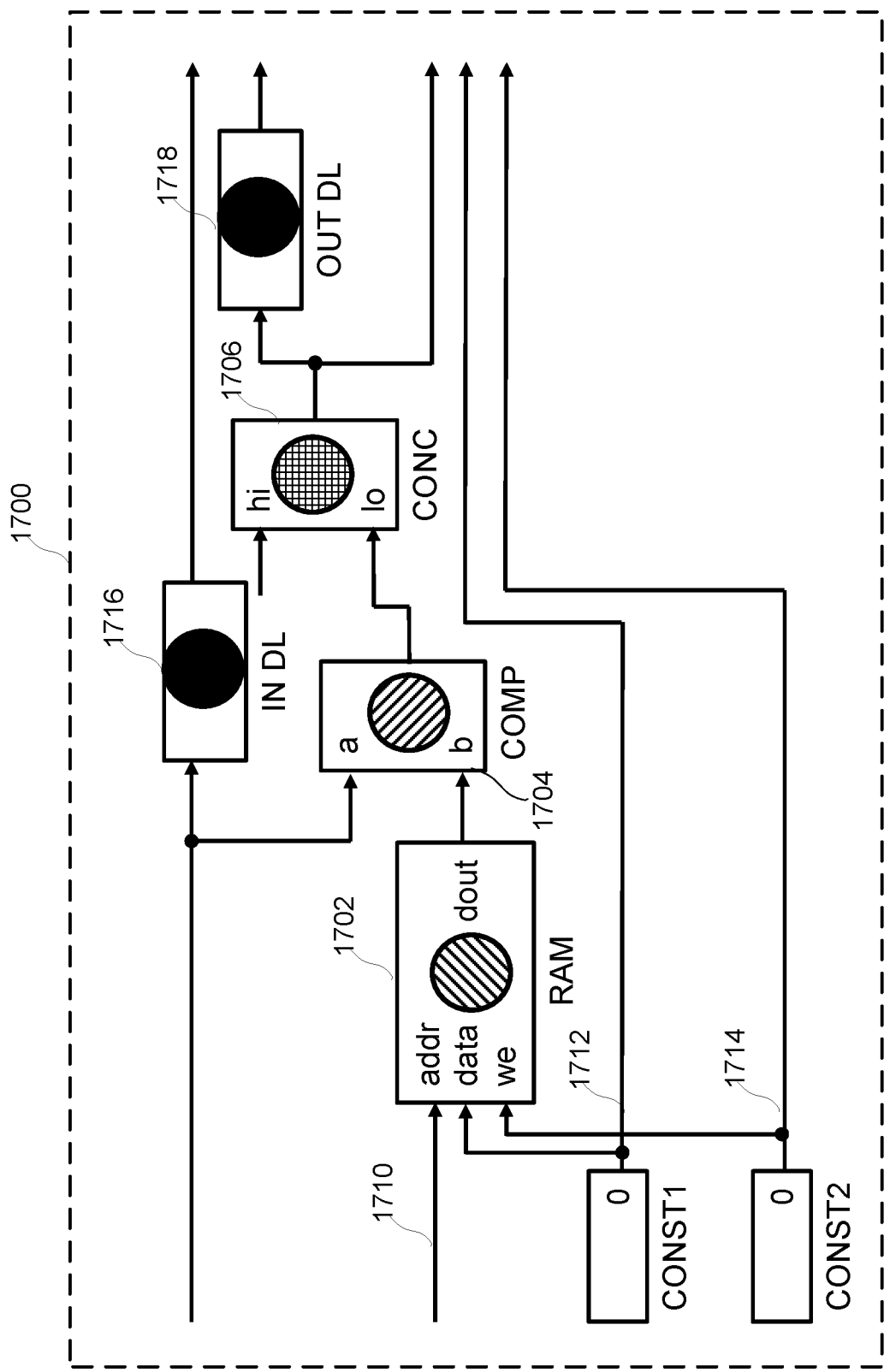
FIG. 17 illustrates a block diagram showing an example hardware implementation of one stage of a dynamic range data compression method.
Figure 18:
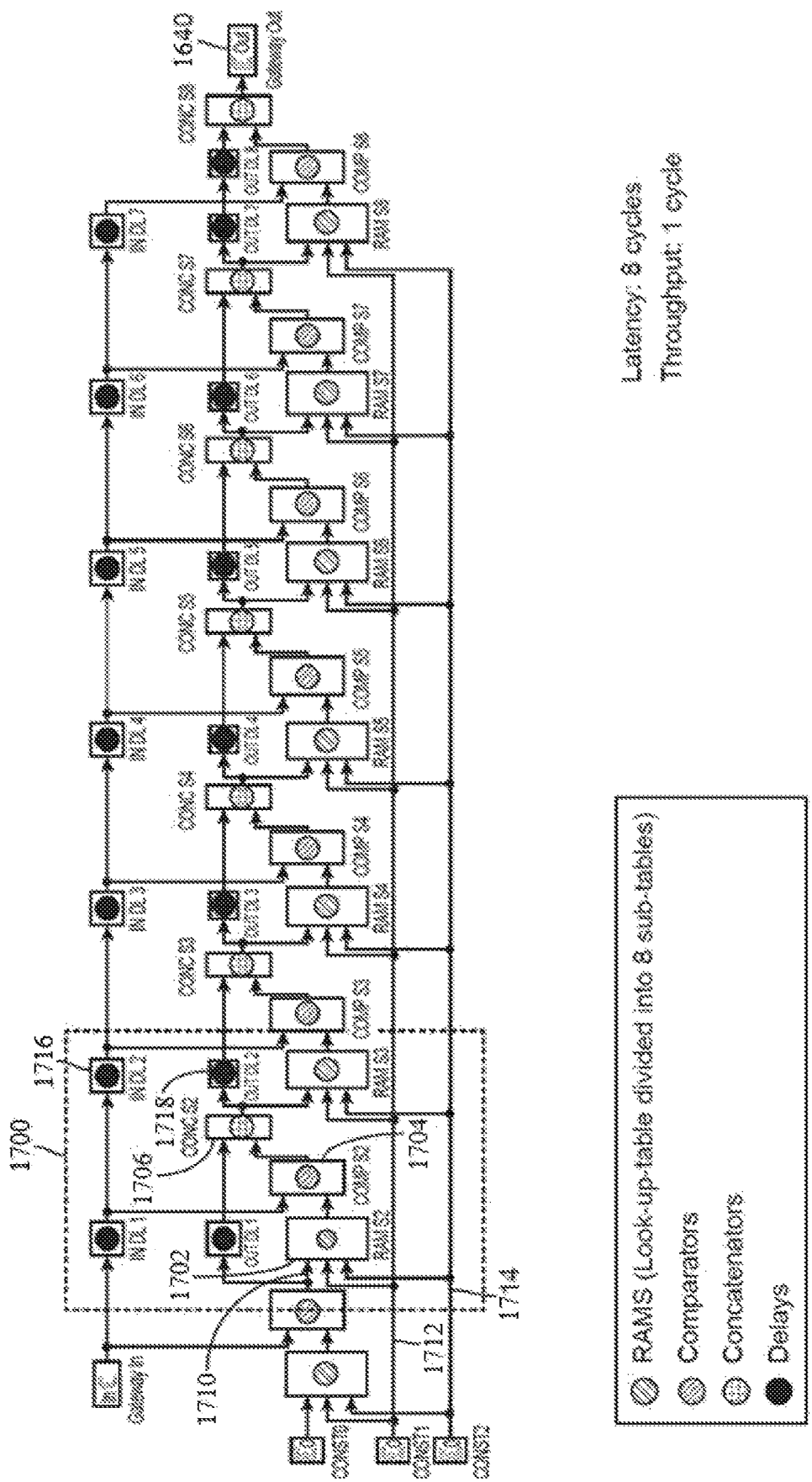
FIG. 18 illustrates a block diagram showing an example hardware implementation of an 8-stage dynamic range data compression method.

FIG. 17 illustrates a block diagram showing an example hardware implementation of one stage of an n-stage dynamic range data compression circuit, which may be used for some embodiments described therein. FIG. 18 illustrates a block diagram showing an example hardware implementation of an 8-stage dynamic range data compression circuit, which may be used for some embodiments described therein. The hardware implementation shown here comprises 8 stages but in general may be configured to comprise n stages, where n may be any integer value of at least 2. Each stage 1700 of the 8 stages may comprise one or more RAMs 1702, one or more comparators 1704, one or more concatenators 1706, and one or more delays (e.g., an input delay 1716 and/or an output delay 1718), as described elsewhere herein.

Each RAM 1702 may have one or more inputs (e.g., ADDR (address) 1710, DATA 1712, WE (write enable) 1714, etc.) and one or more outputs (e.g. DOUT, data out). ADDR 1710 may be the input address for the RAM 1702 to read from or write to. For the first stage in the plurality of stages, ADDR 1710 may be hardcoded at 0 (e.g., by a constant value CONST0) for the first-stage RAM (e.g., S1) 1702. Alternatively or in combination, a first-stage RAM 1702 may be implemented using a simple register, as it stores only a single value. For a stage that is not the first stage in the plurality of stages, ADDR 1710 may comprise a concatenation of outputs from all the previous stages (as described elsewhere herein) for lookup into a sub-table stored in the RAM 1702. In the $i^{th}$ stage, ADDR 1710 may comprise (i–1) bits (e.g., a concatenation of outputs from all the previous (i–1) stages). ADDR 1710 may comprise no more than the number n of bits (e.g., dynamic range) corresponding to the compressed data (e.g., compressed pixels).

DATA 1712 may be the data to be written into the RAM S1 1702. DATA 1712 may be hardcoded at 0 (e.g., by a constant value CONST1) for a logic circuit that does not need to write data. DATA 1712 may be set at 0 (e.g., by a constant value CONST1) for one or more clock cycles during which the logic circuit does not need to write data. WE 1714 may be the write enable signal for the RAM 1702. WE 1714 may be hardcoded at 0 (e.g., by a constant value CONST2) for a logic circuit that does not need to write data. WE 1714 may be set at 0 (e.g., by a constant value CONST2) for one or more clock cycles during which the logic circuit does not need to write data. DOUT for a RAM 1702 may comprise a lookup table value retrieved at a given stage, e.g., during a recursive binary search method. Comparators 1704 for a given stage may generate bitwise values of a portion of output words, as described elsewhere herein. Concatenators 1706 may concatenate (e.g., join together) a bit of the output word generated at a given stage with one or more bits generated from previous stages.

A plurality of dynamic range compressed pixels may be generated from a plurality of uncompressed pixels comprising a first intensity resolution (e.g., a first dynamic range) by compressing the uncompressed pixels to be represented by a second intensity resolution (e.g., a second dynamic range less than the first dynamic range). The first dynamic range may comprise, e.g., 2 bits, 4 bits, 8 bits, 16 bits, 24 bits, 32 bits, 48 bits, 64 bits, 96 bits, 128 bits, or any number of bits in between these values. The second dynamic range may comprise a number of bits smaller than the first dynamic range (e.g., 1 bit, 2 bits, 4 bits, 8 bits, 16 bits, 24 bits, 32 bits, 48, 64 bits, 96 bits, or any number of bits in between these values). Such pixel dynamic range compression may be performed in accordance with a lookup table, as described elsewhere herein.

A data compression circuitry may be configured to generate compressed pixels at a rate sufficient to satisfy a minimum frame rate. For example, a minimum frame rate for compressed pixel generation may be 5 frames per second (fps) (e.g., 5 Hz), 10 fps (e.g., 10 Hz), 20 fps (e.g., 20 Hz), 30 fps (e.g., 30 Hz), 40 fps (e.g., 40 Hz), 50 fps (e.g., 50 Hz), 60 fps (e.g., 60 Hz), 100 fps (e.g., 100 Hz), or 200 fps (e.g., 200 Hz), in which case compressed pixels may be generated at a rate sufficient to generate a full image within a time of no more than about 200 milliseconds (ms), about 100 ms, about 50 ms, about 33 ms, about 25 ms, about 20 ms, about 17 ms, about 10 ms, or about 5 ms, respectively.

By generating a plurality of dynamic range compressed pixels at a sufficient rate (e.g., within no more than about 50 ms for a 20 Hz frame rate), a plurality of ultrasound images may be generated and subsequently outputted to a buffer of a wireless communication circuitry with a latency from a most recent acquisition time from the A/D converter to a most recent output of a compressed pixel for each of the plurality of images of no more than about 50 ms for each of the plurality of ultrasound images. Each of the plurality of ultrasound images may comprise a spatial resolution equal to the spatial resolution of uncompressed images, as well as pixels with a second intensity resolution less than the first intensity resolution of uncompressed pixels. Each of the compressed pixels may be generated at a rate of about one pixel per clock cycle of the processor, about one pixel per two clock cycles of the processor, about one pixel per three clock cycles of the processor, about one pixel per four clock cycles of the processor, or about one pixel per five cycles of the processor.

A dynamic range data compression circuitry may be configured to generate compressed pixels in a period of time no more than about 1 clock cycle, about 2 clock cycles, about 3 clock cycles, about 4 clock cycles, or about 5 clock cycles of a processor. In these cases, such a data compression circuitry may generate about 100 thousand, about 50 thousand, about 33 thousand, about 25 thousand, or about 20 thousand pixels, respectively, in a period of time corresponding to 100,000 clock cycles of a processor. Therefore, a latency between ultrasound images output may be no more than about 100,000 clock cycles, provided the ultrasound images comprise a number of pixels that can be generated at a sufficiently high rate. For example, a processor may be configured to output a plurality of compressed pixels to the buffer at a rate of at least one pixel per 0.6 microseconds (μs), which is sufficient to generate ultrasound images comprising about 58,000 pixels at a frame rate of 30 Hz.

An apparatus for compressing input words of m bits to output words of n bits, wherein n<m, may comprise a plurality of n memory components, each memory component configured to store a respective sub-table of a lookup table, wherein the lookup table comprises a plurality of ordered threshold values, the threshold values corresponding to a domain of a monotonic function and respective indices of the threshold values as ordered corresponding to a range of the monotonic function; and a logic circuit comprising bitwise operations for: determining, in a plurality of n stages respectively corresponding to the plurality of n sub-tables, based on an input word and the plurality of n sub-tables, a plurality of n bits of an output word; and concatenating the plurality of n bits to generate the output word.

Each memory component of the apparatus may be configured to store a respective sub-table of a lookup table. The memory components may be different sizes. For example, each memory component may be the smallest commonly available size (e.g., a size corresponding to a number of bits that is a power of 2) that is sufficient to fit an entire sub-table of the plurality of sub-tables that comprise a lookup table. The memory components may be the same size. For example, each memory component may be the smallest commonly available size (e.g., a size corresponding to a number of bits that is a power of 2) that is sufficient to fit the entirety of the largest sub-table of the plurality of sub-tables that comprise a lookup table.

The logic circuit may be exemplified by the block diagram shown in FIG. 17 and FIG. 18. The logic circuit may comprise one or more RAMs 1702, one or more comparators 1704, one or more concatenators 1706, and one or more delays (e.g., an input delay 1716 and/or an output delay 1718). Each RAM 1702 of the one or more RAMs may store a sub-table of a stage. Each comparator 1704 of the one or more comparators may have an output that is a bit of the final output value. Each comparator 1704 of the one or more comparators may determine a bit of an address into the RAM 1702 associated with the sub-table of a stage, as described in Table 2. Each concatenator 1706 of the one or more concatenators may concatenate the comparator output of a given stage with the concatenated bit or bits calculated and concatenated from previous stages. Each delay (e.g., an input delay 1716 and/or an output delay 1718) of the one or more delays may be used for pipelining and synchronizing different data paths.

Figure 19:
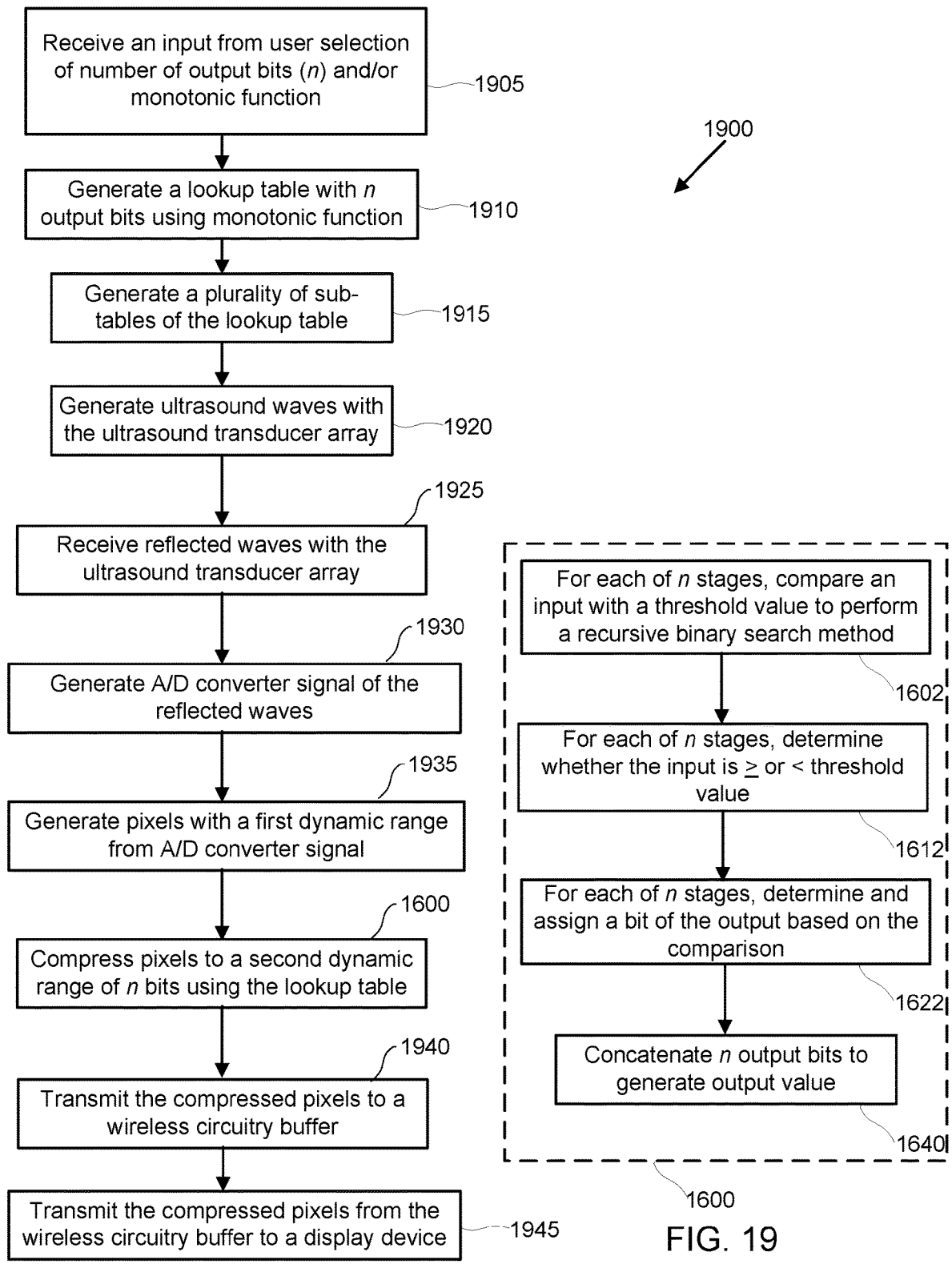
FIG. 19 illustrates a flowchart showing an example of steps to perform dynamic range image compression on a handheld ultrasound probe device.

FIG. 19 illustrates a method 1900 to perform image dynamic range compression on a handheld ultrasound probe device. In step 1905, an input is received from user selection of a number of output bits (n) and/or a monotonic function. In step 1910, a lookup table is generated after receiving a user input of n bits (e.g., the number of output bits) and the monotonic function. The lookup table may comprise $(2^n)-1$ entries, and each data entry may comprise m bits (e.g., the number of input bits). Next, in step 1915, a plurality of sub-tables of the lookup table is generated. Next, in step 1920, ultrasound waves are generated with the ultrasound transducer array. Next, in step 1925, reflected waves are received with the ultrasound transducer array. Next, in step 1930, the A/D converter generates an A/D converter signal of the reflected waves. Next, in step 1935, this A/D converter signal may be beamformed by a beamformer to generate input data (e.g., pixel data) with a first dynamic range. Next, in step 1600, the generated pixels are compressed to a second dynamic range of n bits less than the first dynamic range using the lookup table. Next, in step 1940, the dynamic range compressed pixels are transmitted to a wireless circuitry buffer. Finally, in step 1945, the dynamic range compressed pixels are transmitted from the wireless circuitry buffer to a display device. In steps 1940 and/or 1945, the wireless circuitry buffer may alternatively or in combination be implemented using a wired communication connection or link.

As described elsewhere herein, step 1600 may comprise steps 1602, 1612, 1622, and 1640. In step 1602, for each of n stages, the input is compared with a threshold value to perform a recursive binary search method. Next, for each of n stages (e.g., in step 1612), the determination is made whether the input is ≥ (greater than or equal to) or < (less than) the threshold value. Next, for each of n stages (e.g., in step 1622), a bit of the output is determined and assigned based on the comparison (e.g., step 1612). Finally, the n output bits are concatenated to generate the output value 1640.

Although FIG. 19 shows a method of dynamic range compression in accordance with some embodiments, a person of ordinary skill in the art will recognized many adaptations and variations. For example, the steps may be performed in any order. Some of the steps may be removed, some of the steps repeated, and additional steps performed.

The logic circuit may comprise a latency and a throughput. The apparatus may perform the plurality of n stages in n clock cycles ("cycles"). The latency of the circuit may comprise a sum of all delays (each delay corresponding to each stage) of all stages in the circuit. The latency of determining the plurality of bits of an output word may be at most n clock cycles. The latency of determining the plurality of bits of an output word may be n clock cycles. For example, an 8-stage implementation for an 8-bit output function may have a latency of 8 clock cycles. The cycle time (in seconds, s) may be the inverse of the clock frequency (in Hertz, Hz) of the processor.

The throughput of the circuit may comprise the delay time needed to calculate an output bit of a stage. The throughput of the circuit may be expressed as the rate of output words generated per clock cycle. Each stage of the plurality of stages may be performed in one clock cycle. The plurality of n stages may be configured in a pipeline to enable differently positioned bits of a plurality of output words to each be determined by a respective corresponding stage of the plurality of stages in a same clock cycle. In this way, an n-stage implementation for an n-bit output function may have a throughput of one output word per one clock cycle. A throughput of the logic circuit may be at least one output word per clock cycle.

An application-specific integrated circuit (ASIC) may comprise the logic circuit. A field-programmable gate array (FPGA) may comprise the logic circuit.

The apparatus may determine the plurality of n bits of the output word by performing comparisons of the input word to no more than n threshold values. This determining may be implemented by a recursive binary search method. This determining may be implemented by a search method with an expected runtime that is logarithmic order in base 2 with the number of threshold values searched, e.g., uniform binary search, Fibonacci search, exponential search, interpolation search, or fractional cascading.

The apparatus may determine the plurality of bits of the output word based on comparing the input word to a selected threshold value at each stage of the plurality of stages, the threshold value at each respective stage after the first stage being selected based on the bits of the output word determined in previous stages of the plurality of stages. For example, the recursive binary search method of FIG. 16 compares the input word to a selected threshold value at each stage of the plurality of stages. The determining of the plurality of bits of the output word may comprise: in a first stage of the plurality of stages, determining, based on a first sub-table stored in a first memory component of the plurality of memory components, a most significant bit (MSB) of the output word. This determining may be based on comparing the input word to a first threshold value stored in a first memory component of the plurality of memory components.

In each successive stage of the plurality of stages, the next most significant bit of the output word may be determined. This determining may be based on one or more corresponding additional sub-tables of the plurality of sub-tables and the most significant bit. This determining may be based on the respective sub-table stored in the corresponding memory component and bits of the output word determined in previous stages of the plurality of stages, a next bit of the output word corresponding to the respective stage. In each successive stage after the first stage of the plurality of stages, the bits of the output word may be determined based on bits determined in previous stages of the plurality of stages, which may also be used as an address of a threshold value in the memory component corresponding to the respective stage, and determining, based on comparing the input word to the threshold value at the address, a next bit of the output word corresponding to the respective stage.

Each sub-table of the lookup table of the apparatus may correspond to a respective level of a binary search tree. Each memory component may correspond to a respective level of a binary search tree. The determining of the plurality of bits of the output word may comprise searching the binary tree.

The plurality of threshold values of the apparatus may be at most $2^n-1$ threshold values. The plurality of threshold values of the apparatus may be $2^n-1$ threshold values. A size of the lookup table of the apparatus may be at most $m \cdot (2^n-1)$ bits. A size of the lookup table of the apparatus may be $m \cdot (2^n-1)$ bits.

The apparatus may comprise a means for dividing up the lookup table into the plurality of sub-tables. Each ith sub-table of the plurality of n sub-tables in the apparatus may comprise at most $2^{(i-1)}$ threshold values of the plurality of threshold values. Each ith sub-table of the plurality of n sub-tables in the apparatus may comprise $2^{(i-1)}$ threshold values of the plurality of threshold values.

Each $i^{th}$ memory component of the plurality of n memory components may be configured to store at least $m \cdot (2^{(i-1)})$ bits. Each $i^{th}$ memory component of the plurality of n memory components may be configured to store at most $m \cdot (2^{(i-1)})$ bits.

The plurality of memory components may be read-only memory (ROM). The plurality of memory components may be random-access memory (RAM).

The n bits of the apparatus may be 1, 2, 4, 8, 16, 32, 64, 128, 256, 512, 1024, or 2048 bits, or any number of bits between these values. The m bits of the apparatus may be 2, 4, 8, 16, 32, 64, 128, 256, 512, 1024, or 2048 bits, or any number of bits between these values.

The input words of the apparatus may represent an image with a first dynamic range, and the output words may represent the image with a second dynamic range less than the first dynamic range. This image may be ultrasound image data. This image may be image data generated by computed tomography (CT), magnetic resonance imaging (MRI), positron emission tomography (PET), PET-CT, single-photon emission computed tomography (SPECT), X-ray radiography, thermography, endoscopy, elastography, or other medical imaging modality.

A system for compressing medical imaging data, such as ultrasound image data, may comprise a means for receiving ultrasound image data at a bitrate corresponding to m, and the apparatus for compressing the ultrasound image data to a bitrate corresponding to n. The system may be configured to compress live ultrasound data in real time to the bitrate corresponding to n. The system may comprise a means for outputting the live ultrasound image data for display at the bitrate corresponding to n. This bitrate may be achieved by using a processor with a clock cycle sufficient to achieve a necessary throughput of data compression.

The system may comprise a means for generating the plurality of threshold values based on n and the monotonic function. The system may comprise a means for storing the plurality of threshold values in the plurality of n memory components. The system may comprise a means for storing the plurality of threshold values in a plurality of at least n memory components. The system may comprise a means for storing the plurality of threshold values in a plurality of at most n memory components. The system may comprise a means for storing the plurality of threshold values in a single memory component.

The system may comprise a means for receiving a user selection of n. The system may be configured to have a non-user selected value of n. The system may comprise a means for receiving a user selection of the monotonic function. This monotonic function may be selected from a set of a plurality of predetermined monotonic functions. The system may be configured to have a non-user selected monotonic function.

The monotonic function of the apparatus may be configured in many ways, such as a logarithmic function. The monotonic function of the apparatus may be an exponential function. The monotonic function of the apparatus may be a gamma function (e.g., y=x^gamma, where 0<gamma <1). The monotonic function of the apparatus may be a polynomial function (e.g., monomial or binomial). The monotonic function may be a composite function of two or more monotonic functions (e.g., a logarithmic function and a gamma function). The monotonic function may be an arithmetic combination (e.g., a sum, a weighted sum, or a product) of two or more monotonic functions.

A portable (e.g., handheld) device for real-time ultrasound imaging (or another type of medical imaging) may comprise the apparatus for compressing input words of m bits to output words of n bits, wherein n<m.

A logic circuit for compressing input words of m bits to output words of n bits, wherein n<m, may comprise bitwise operations for: determining, in a plurality of n pipeline stages respectively corresponding to a plurality of n sub-tables of a lookup table, wherein the lookup table comprises a plurality of $(2^n)-1$ ordered threshold values and each $i^{th}$ sub-table of the n sub-tables comprises $2^{(i-1)}$ threshold values, the threshold values corresponding to a domain of a monotonic function and respective indices of the threshold values as ordered corresponding to a range of the monotonic function, a plurality of n bits of an output word; and concatenating the plurality of n bits to generate the output word; wherein a latency of the logic circuit is at most n clock cycles and a throughput of the logic circuit is at least one output word per cycle.

An application-specific integrated circuit (ASIC) may comprise the logic circuit. A field-programmable gate array (FPGA) may comprise the logic circuit. An apparatus for compressing input words of m bits to output words of n bits, wherein n<m, may comprise the logic circuit and a plurality of n memory components respectively corresponding to the n pipeline stages and n sub-tables, each memory component comprising at least a minimum size necessary to store the corresponding sub-table of the plurality of n sub-tables.

Figure 20:
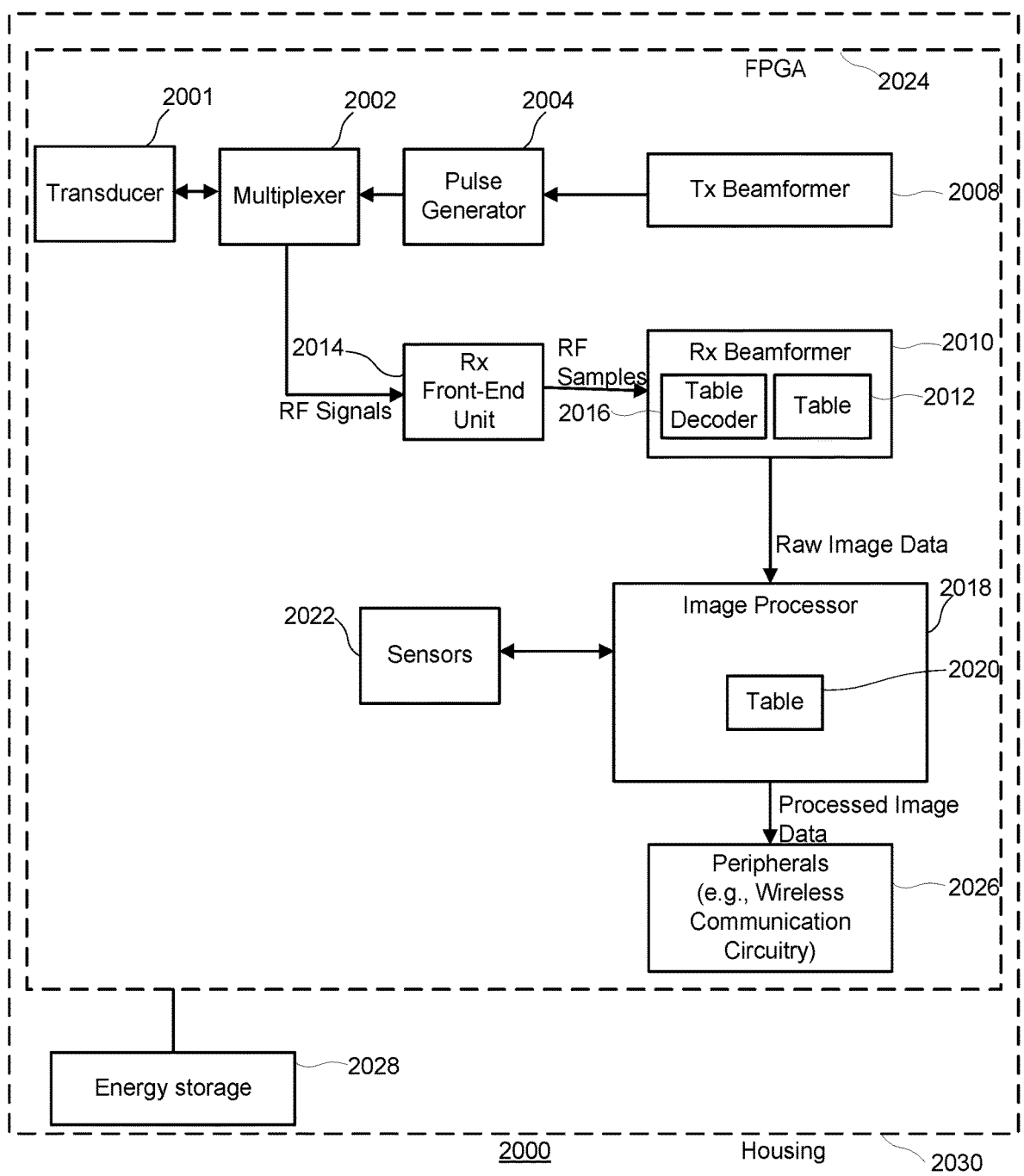
FIG. 20 illustrates a block diagram of an example high performance handheld ultrasound imaging device.

FIG. 20 illustrates a block diagram of an example ultrasound device 200, which may be used for some implementations described herein. For example, ultrasound device 200 may be used to implement ultrasound device 100 of FIG. 1. In some implementations, ultrasound device 200 includes a transducer array 2001, a switch 2002, and a pulse generator 2004. Transducer array 2001 may also be referred to as transducer 2001. Ultrasound device 200 may include a transmit (Tx) beamformer 2008 and/or a receive (Rx) beamformer 2010. Rx beamformer 2010 may include a memory that stores a table 2012. Ultrasound device 200 may include an Rx front-end unit 2014 and/or an image processor 2018. In some implementations, ultrasound device 200 also includes sensors 2022 and/or peripherals 2026.

In some implementations, a table 2012 may be stored on FPGA 2024, or stored on any other suitable storage device. Furthermore, in various implementations, FPGA 2024 may not have all of the components shown and/or may have other elements including other types of elements instead of, or in addition to, those shown herein. For example, in some implementations, FPGA 2024 may include image processor 2018. Furthermore, while image processor 2018 is described herein as performing separate functions, in some implementations, a single processing unit such as FPGA 2024 may perform all of the functions and implementations described herein.

For ease of illustration, FIG. 20 shows one block for each of component of ultrasound device 2000. In other implementations, ultrasound device 2000 may not have all of the components shown and/or may have other elements including other types of elements instead of, or in addition to, those shown herein.

In operation, Tx beamformer 2008 causes pulse generator 2004 to generate electrical signals based on transmit beamforming, where the electrical signals are applied to transducer array (or "transducer") 2001. The electrical signals or pulses may be produced at a predetermined pulse rate (e.g., 1,000 pulses per second, etc.), depending on the particular implementation. For instance, the electrical signals can be produced at a rate greater than 100 pulses per second, greater than 200 pulses per second, greater than 500 pulses per second, greater than 1000 pulses per second, greater than 2000 pulses per second, greater than 5000 pulses per second, or greater than 10000 pulses per second. The electrical signals may be produced at a pulse rate within a range defined by any two of the preceding values. The pulse generator may control the length of a pulse. The pulse generator may control the total number of pulses applied during a signal acquisition. The pulse generator may control the amplitude of the electrical signals, which may in turn control the intensity and energy of an ultrasound beam produced by the transducer array.

The switch 2002 selects one of two operating modes: (1) select the signal in the direction from the pulse generator 2004 to the transducer 2001 or (2) select the signal in the direction from the transducer 2001 to the Rx front-end unit 2014.

In various implementations, pulse generator 2004 controls the amplitude of the electrical signals or pulses, which in turn controls the intensity and energy of an ultrasound beam produced by transducer array 2001, after the signal is selected in the direction from the pulse generator 2004 to the transducer array 2001 by the switch 2002. Pulse generator 2004 may also control the width of the pulses (which in turn controls the signal frequency) and the number of cycles in the pulses (which in turn controls the energy and the bandwidth of the signal).

Transducer array 2001 generates ultrasonic waves based on the electrical signals received from pulse generator 2004. The ultrasonic waves may also be referred to as ultrasound waves, ultrasonic pulses, or ultrasound pulses.

In various implementations, transducer array 2001, also referred to as a transducer or probe, is positioned in direct contact with a surface such as the body of a patient (e.g., the abdomen of a patient). In some implementations, the probe need not be in direct contact with the surface. For example, there may be water or another medium between the probe and the surface. In some implementations, when the probe is in direct contact with the surface, an ultrasound gel may be used to couple the probe with the surface. Transducer array 2001 focuses a beam of ultrasonic waves or pulses to give the beam a particular size and shape at various depths within a particular space/area beneath the surface (e.g., a portion of patient's body). Transducer array 2001 also scans the beam over the space that is being imaged (e.g., over an anatomical area). The space that is being imaged may also be referred to as a region of interest.

In various implementations, transducer array 2001 includes one or more transducer elements. Each transducer element can be referred to as a channel. The transducer array can comprise 32 transducer elements, 64 transducer elements, 128 transducer elements, or 256 transducer elements. The transducer array can comprise a number of elements within a range defined by any two of the preceding values. The transducer array can comprise fewer than 64 or fewer than 32 transducer elements. The transducer array can comprise more than 256 transducer elements.

In some cases, each of the transducer elements can be of the same type. For example, the transducer elements can be piezoelectric transducer elements. The transducer elements can be capacitive transducer elements. The transducer elements can be any transducer element as is known to one having skill in the art. In some cases, the transducer elements can vary in type. For instance, some transducer elements can be piezoelectric transducer elements while other transducer elements are capacitive transducer elements. When an electrical pulse is applied to a given transducer element, the transducer element vibrates and produces the ultrasound, or ultrasonic wave, which is directed at the region of interest. Conversely, when a given transducer element is vibrated by returning ultrasound echoes from objects in the region of interest, the transducer element produces radio frequency (RF) signals. Since the transducer elements can act to both produce and receive ultrasound signals, the ultrasound device can further comprise a switch 2002. The switch may comprise a plurality of switches. The switch may comprise a switch network. The switch may comprise a multiplexer (mux). The switch may comprise a demultiplexer (demux). The switch may comprise a plurality of muxes. The switch may comprise a plurality of demuxes.

When transducer array 2001 receives ultrasonic waves reflected by objects in the region of interest), transducer array 2001 generates RF signals based on the reflected ultrasonic waves. The reflected ultrasonic waves may also be referred to as ultrasonic echoes, or ultrasound echoes, or echoes. The RF signals may also be referred to as raw RF data.

Reception of the ultrasound signals is controlled by a receive (Rx) beamformer 2010. The Rx beamformer can comprise a table 2012. The table can comprise a flag table or a compressed flag table, as discussed herein. The Rx beamformer can comprise a table decoder 2016, as described herein. The table decoder can comprise a flag table decoder, as described herein. The Rx beamformer 2010 can be communicatively coupled to an Rx front-end unit 2014. In some implementations, Rx front-end unit 2014 amplifies and digitizes the RF signals from transducer array 2001 (after the signal is selected in the direction from the transducer 2001 to the Rx front-end unit 2014 by the switch 2002) to provide RF samples, and sends the RF samples to table decoder 2016 of Rx beamformer 2010. The RF samples may also be referred to as digitized RF signals. The Rx front-end unit 2014 may comprise an analog-to-digital (A/D) converter (ADC). The A/D converter may comprise a resolution of at least 2 bits, at least 4 bits, at least 8 bits, at least 16 bits, at least 32 bits, at least 64 bits, or at least 128 bits. The A/D converter may comprise at least 1 channel, at least 2 channels, at least 4 channels, at least 8 channels, at least 16 channels, at least 32 channels, at least 64 channels, or at least 128 channels. In some implementations, Rx front-end unit 2014 amplifies and/or filters the RF signals before digitizing them. In some implementations, the amplifier gain of Rx front-end unit 2014 may vary over time, in order to compensate for ultrasound attenuation.

In various implementations, Rx beamformer 2010 can generate raw image data based on the RF samples, where the Rx beamformer 2010 performs beamforming functions in order to generate the raw image data. The Rx beamformer 2010 can create an intensity map of the reflected ultrasonic waves corresponding to every point in the field of view. Rx beamformer 2010 can map the received signal to a location in an image and coherently sum the signals from all transducer elements for every point in the field of view. Various implementations of Rx beamformer 2010 generating raw image data are described in more detail herein.

Given a high enough sampling rate, one or more of the transducers may receive a plurality of RF samples corresponding to an ultrasound signal emanating from a particular location in a region of interest. In the far field, this may occur when the sampling rate is greater than twice the spacing between pixels in an image line divided by the speed of sound. Each of the plurality of RF samples corresponding to the ultrasound signal from the location may be regarded as conveying information about the location that is at least partially redundant. Thus, any one of the plurality of RF samples corresponding to the ultrasound signal from the location may be sufficient to reconstruct image information for that location. The Rx beamformer may therefore select to utilize only a fraction of the RF samples corresponding to the ultrasound signal from the location. The Rx beamformer may select to utilize one or more of the RF samples in order to reconstruct image information for the location. For instance, the Rx beamformer may select to utilize the RF sample that is closest to the center of a given pixel. Utilizing only a fraction of the RF samples may allow for a reduction in the memory requirements for the handheld ultrasound device.

The Rx beamformer 2010 can determine which of the RF samples are to be used to generate raw image data based on table 2012. As described in more detail herein, table 2012 can indicate which RF samples are to be used to generate raw image data and which RF samples are not to be used to generate raw image data. The table can be predetermined in that information in the table is generated prior to an imaging session. During runtime, the Rx beamformer can check the table during an imaging session in order to determine which RF samples to use to generate raw image data. Implementations of the table are described in more detail herein.

The table 2012 may be predetermined in that information in table 2012 is generated prior to an imaging session, and table 2012 may be pre-loaded in Rx beamformer 2010 or in any other suitable storage location. Table 2012 may also be referred to as predetermined table 2012. During runtime, Rx beamformer 2010 can check table 2012 during an imaging session in order to determine which RF samples to use to generate raw image data. In various implementations, Rx beamformer 2010 generates raw image data based on the RF samples that are to be used to generate raw image data, and then sends the raw image data to image processor 2018.

As indicated herein, image processor 2018 processes the raw image data to provide the processed image data. The processed image data may be referred to as post-processed image data. The processed image data may in turn be used to provide ultrasound images.

As described more detail herein, in various implementations, image processor 2018 determines input values based on the raw image data from Rx beamformer 2010. Image processor 2018 may determine output values based on the input values and a table 2020 (e.g., by using a compression circuitry). In various implementations, image processor 2018 compresses the raw image data such that the dynamic range of the processed image data is smaller than the dynamic range of the raw image data.

In various implementations, table 2020 is predetermined in that information in table 2020 is generated prior to an imaging session, and table 2020 is pre-loaded in image processor 2018 or in any other suitable storage location. Table 2020 may also be referred to as predetermined table 2020. During runtime, image processor 2018 checks table 2020 during an imaging session in order to determine the output values used to generate processed image data. Various implementations of table 2020 are described in more detail herein.

In various implementations, sensors 2022 may include position sensors, rotational sensors, tilt sensors, gyroscopes, accelerometers, etc., for positioning ultrasound device 2000. In some implementations, the position sensors and rotational sensors may be integrated.

In various implementations, peripherals 2026 may include one or more display devices and/or may send processed image data to remote display devices (e.g., a 2D display, a 3D display, a printer, a wearable device, an augmented-reality glass, a virtual-reality glass, etc.). Remote display devices may include stand-alone computers, tablet computers, smartphones, dedicated monitors, etc. In some implementations, peripherals 2026 may also include an electrocardiograph (ECG or EKG device), pulse oximeter, position tracker, needle guide, etc. Peripherals 2026 may include wireless communication circuitry, as described elsewhere herein.

Wireless communication circuitry may comprise a Wi-Fi chip with a buffer. The wireless communication may have an average maximum bandwidth of no more than about 60 megabits per second (Mbps), about 50 Mbps, about 40 Mbps, about 30 Mbps, about 25 Mbps, about 20 Mbps, about 15 Mbps, about 10 Mbps, about 5 Mbps, about 2 Mbps, or about 1 Mbps. The wireless communication may have an average maximum bandwidth that fluctuates during the course of operation due to network congestion, distance of wireless communication transmission, electronic or other electromagnetic interference, etc. The processor may be configured to transmit compressed ultrasound images in real time (e.g., in the range of 5 Hz to 200 Hz) at a bit rate of no more than a maximum average bandwidth of a wireless communication network, (e.g., about 60 Mbps, about 50 Mbps, about 40 Mbps, about 30 Mbps, about 25 Mbps, about 20 Mbps, about 15 Mbps, about 10 Mbps, about 5 Mbps, about 2 Mbps, or about 1 Mbps), without degradation of the spatial resolution and the frame rate of the images. Such real-time compression and transmission of ultrasound images can be achieved without degradation by performing the pixel compression process at a sufficient throughput (e.g., rate).

In various implementations, the ultrasound device may include an energy storage 2028. The energy storage 2028 may comprise one or more batteries, capacitors, or supercapacitors. The energy storage 2028 may be configured to deliver power to the handheld ultrasound probe. At a given time, the energy storage 2028 may be delivering power to one or more components, including the pulse generator 2004, the A/D converter, the wireless communication circuitry or other peripherals, the processor, and/or the processor. The energy storage 2028 may be configured to shut off power to one or more components when not in active use to save energy. The energy storage 2028 may be configured to deliver varying amounts of voltage to each of the components, including the ultrasound transducer array (e.g., through a pulse generator 2004), the A/D converter, the wireless communication circuitry or other peripherals, the processor, and/or the processor. The energy storage 2028 may be configured to deliver varying amounts of power to each of the components, including the ultrasound transducer array (e.g., through a pulse generator 2004), the A/D converter, the wireless communication circuitry or other peripherals, the processor, and/or the processor.

The energy storage 2028 may be configured to operate in one of a plurality of power modes, e.g., normal, high-performance (e.g., with higher power draw), battery-saving (e.g., with lower power draw and performance such as a decreased spatial resolution or frame rate of ultrasound images). The energy storage 2028 may be configured to be recharged from an alternating current (AC) power source (e.g., household AC socket) or from a direct current (DC) power source (e.g., another energy storage unit such as a battery). The energy storage 2028 may be configured to accept one or more non-rechargeable energy storage units (e.g., non-rechargeable batteries) as a power source. The energy storage 2028 may be configured to deliver in a single charge cycle (e.g., a period of operation without recharging) sufficient power to operate the handheld ultrasound probe for a period of time (e.g., a range of 30 minutes to one hour) sufficient to perform a typical ultrasound scan. The energy storage 2028 may be configured to deliver in a single charge cycle (e.g., a period of operation without recharging) sufficient power to operate the handheld ultrasound probe a period of time (e.g., a range of 30 minutes to one hour) sufficient to perform a plurality of typical ultrasound scans during the course of a work day or hospital shift (e.g., 4 hours, 6 hours, 8 hours, 10 hours, 12 hours, 14 hours, 16 hours, 18 hours, 20 hours, 22 hours, or 24 hours).

The handheld ultrasound probe may comprise a housing 2030. The housing 2030 may support one or more of: the ultrasound transducer array 2001, the switch 2002, the pulse generator 2004, the transmit (Tx) beamformer 2008, the receive (Rx) beamformer 2010, the table 2012, the receive (Rx) front-end unit 2014, the table decoder 2016, the image processor 2018, the table 2020, the sensors 2022, the FPGA 2024, the peripherals (e.g., wireless communication circuitry) 2026, and the energy storage device 2028, when the housing 2030 is grasped by a user. The housing 2030 may enclose one or more of: the ultrasound transducer array 2001, the switch 2002, the pulse generator 2004, the transmit (Tx) beamformer 2008, the receive (Rx) beamformer 2010, the table 2012, the receive (Rx) front-end unit 2014, the table decoder 2016, the image processor 2018, the table 2020, the sensors 2022, the FPGA 2024, the peripherals (e.g., wireless communication circuitry) 2026, and the energy storage device 2028, when the housing 2030 is grasped by a user. The housing 2030 may comprise a display for outputting visual information, e.g., ultrasound images or a graphical user interface.

One or more of the components 2001, 2002, 2004, 2008, 2010, 2012, 2014, 2016, 2018, 2020, 2022, and 2026 of the ultrasound device can be implemented on an FPGA 2024. In some cases, all of the components 2001, 2002, 2004, 2008, 2010, 2012, 2014, 2016, 2018, 2020, 2022, and 2026 of the ultrasound device are implemented on an FPGA. In some cases, components 2008, 2010, 2012, 2016, 2018, and 2020 are implemented on an FPGA. One or more of the components 2001, 2002, 2004, 2008, 2010, 2012, 2014, 2016, 2018, 2020, 2022, or 2026 of the ultrasound device can be implemented on an ASIC. In some cases, all of the components 2001, 2002, 2004, 2008, 2010, 2012, 2014, 2016, 2018, 2020, 2022, and 2026 of the ultrasound device are implemented on an ASIC. In some cases, components 2008, 2010, 2012, 2016, 2018, and 2020 are implemented on an ASIC. To enable ease of portability for a handheld ultrasound device, the components of the ultrasound device may be configured such that the handheld probe comprises a weight of no more than about 300 grams.

Although the description has been described with respect to particular embodiments thereof, these particular embodiments are merely illustrative, and not restrictive. Concepts illustrated in the examples may be applied to other examples and implementations.

In various implementations, software is encoded in one or more non-transitory computer-readable media for execution by one or more processors. The software when executed by one or more processors is operable to perform the implementations described herein and other functions.

Any suitable programming language can be used to implement the routines of particular embodiments including C, C++, Java, assembly language, etc. Different programming techniques can be employed such as procedural or object oriented. The routines can execute on a single processing device or multiple processors. Although the steps, operations, or computations may be presented in a specific order, this order may be changed in different particular embodiments. In some particular embodiments, multiple steps shown as sequential in this specification can be performed at the same time.

Particular embodiments may be implemented in a non-transitory computer-readable storage medium (also referred to as a machine-readable storage medium) for use by or in connection with the instruction execution system, apparatus, or device. Particular embodiments can be implemented in the form of control logic in software or hardware or a combination of both. The control logic when executed by one or more processors is operable to perform the implementations described herein and other functions. For example, a tangible medium such as a hardware storage device can be used to store the control logic, which can include executable instructions.

Particular embodiments may be implemented by using a programmable general purpose digital computer, and/or by using application specific integrated circuits, programmable logic devices, field programmable gate arrays, optical, chemical, biological, quantum or nano-engineered systems, components and mechanisms. In general, the functions of particular embodiments can be achieved by any means as is known in the art. Distributed, networked systems, components, and/or circuits can be used. Communication, or transfer, of data may be wired, wireless, or by any other means.

A "processor" may include any suitable hardware and/or software system, mechanism or component that processes data, signals or other information. A processor may include a system with a general-purpose central processing unit, multiple processing units, dedicated circuitry for achieving functionality, or other systems. Processing need not be limited to a geographic location, or have temporal limitations. For example, a processor may perform its functions in "real-time," "offline," in a "batch mode," etc. Portions of processing may be performed at different times and at different locations, by different (or the same) processing systems. A computer may be any processor in communication with a memory. The memory may be any suitable data storage, memory and/or non-transitory computer-readable storage medium, including electronic storage devices such as random-access memory (RAM), read-only memory (ROM), magnetic storage device (hard disk drive or the like), flash, optical storage device (CD, DVD, or the like), magnetic or optical disk, or other tangible media suitable for storing instructions (e.g., program or software instructions) for execution by the processor. For example, a tangible medium such as a hardware storage device can be used to store the control logic, which can include executable instructions. The instructions can also be contained in, and provided as, an electronic signal, for example in the form of software as a service (SaaS) delivered from a server (e.g., a distributed system and/or a cloud computing system).

It will also be appreciated that one or more of the elements depicted in the drawings/figures can also be implemented in a more separated or integrated manner, or even removed or rendered as inoperable in certain cases, as is useful in accordance with a particular application. It is also within the spirit and scope to implement a program or code that can be stored in a machine-readable medium to permit a computer to perform any of the methods described above.

Although reference is made to compression of data on a hand held imaging probe, the methods, apparatus and circuitry disclosed herein will find application in many fields, such as electronics, imaging, automobiles, and telecommunications.

While preferred embodiments of the present invention have been shown and described herein, it will be obvious to those skilled in the art that such embodiments are provided by way of example only. It is not intended that the invention be limited by the specific examples provided within the specification. While the invention has been described with reference to the aforementioned specification, the descriptions and illustrations of the embodiments herein are not meant to be construed in a limiting sense. Numerous variations, changes, and substitutions will now occur to those skilled in the art without departing from the invention. Furthermore, it shall be understood that all aspects of the invention are not limited to the specific depictions, configurations or relative proportions set forth herein which depend upon a variety of conditions and variables. It should be understood that various alternatives to the embodiments of the invention described herein can be employed in practicing the invention. It is therefore contemplated that the invention shall also cover any such alternatives, modifications, variations or equivalents. It is intended that the following claims define the scope of the invention and that methods and structures within the scope of these claims and their equivalents be covered thereby.

What is claimed is:

1. An ultrasound device to generate image data of an object, comprising:
   a plurality of transducer elements, wherein each transducer element is associated with a data channel, and wherein each data channel comprises a transducer that generates radio frequency (RF) signals based on ultrasonic energy reflected by a region of interest of the object;
   a front-end circuitry that digitizes the RF signals received from each data channel to provide RF samples at an RF sampling rate associated with a data clock having a clock cycle, wherein an RF sample of the RF samples is received by each data channel at each clock cycle corresponding to the RF sampling rate, and wherein each RF sample is associated with a location along a scanline defined by a trajectory of a beam of ultrasonic energy through the region of interest; and
   a real-time beamformer having a transmit beamformer and a flag table-based receive beamformer, wherein the transmit beamformer directs a beam of ultrasonic energy at a region of interest, the beam generating ultrasound signals along a scanline defined by a trajectory of the beam through the region of interest, and wherein the flag table-based receive beamformer receives reflected ultrasound signals from portions of the region of interest that lie along the scanline, the flag table-based receive beamformer comprising:
a flag table generated for the beam and for each data channel, the flag table comprising a flag associated with each of the RF samples provided by the front-end circuitry, and wherein each flag comprises a first flag indicator value or a second flag indicator value; and
a processor that generates the image data comprising a set of pixels, the processor performing operations in real-time comprising processing each of the RF samples provided by the front-end circuitry based on the flag table for each of the data channels and for the beam of ultrasonic energy directed at the region of interest, wherein the processing further comprises:
  a. receiving the RF sample of the RF samples at a clock cycle of the data clock, the RF sample associated with the location along the scanline defined by the trajectory of the beam through the region of interest;
  b. sending the received RF sample to a first pixel of the set of pixels in a per-data channel image buffer if the flag associated with the received RF sample comprises the first flag indicator value;
  c. discarding the received RF sample if the flag associated with the received RF sample comprises the second flag indicator value;
  d. processing RF samples corresponding to the first pixel from all of the data channels to generate an image value for the first pixel.

2. The ultrasound device of claim 1, wherein the front-end circuitry further amplifies the RF signals.

3. The ultrasound device of claim 1, further comprising an image processor that processes the image data to provide processed image data.

4. The ultrasound device of claim 1, wherein the flag table is compressed.

5. The ultrasound device of claim 4, wherein the processor performs further operations comprising decoding the compressed flag table.

6. The ultrasound device of claim 1, wherein the processor processes the RF samples provided by the front-end circuitry based on the flag table without using an RF buffer to store the RF samples.

7. The ultrasound device of claim 1, wherein the flag table-based receive beamformer comprises one or more field programmable gate array (FPGA) chips or an application-specific integrated circuit (ASIC).

8. The ultrasound device of claim 7, wherein the one or more FPGA chips or the ASIC comprises an equivalent gate count of no more than about 100,000 gates exclusive of a memory component.

9. A method comprising:
directing a beam of ultrasonic energy at a region of interest, the beam generating ultrasound signals along a scanline defined by a trajectory of the beam through the region of interest;
generating, by a plurality of data channels, radio frequency (RF) signals based on ultrasound signals reflected from portions of the region of interest that lie along the scanline;
digitizing the generated RF signals received from the plurality of data channels to provide RF samples at an RF sampling rate associated with a data clock having a clock cycle, wherein an RF sample of the RF samples is received by each of the plurality of data channels at each clock cycle corresponding to the RF sampling rate, and wherein the RF sample is associated with a location along the scanline defined by the trajectory of the beam through the region of interest;
generating a flag table for the beam and for each data channel, the flag table comprising a flag associated with each of the RF samples, and wherein each flag comprises a first flag indicator value or a second flag indicator value;
generating image data comprising a set of pixels, at least in part by processing each of the RF samples based on the flag table for each of the data channels and for the beam of ultrasonic energy directed at the region of interest, wherein the processing further comprises:
  a. receiving the RF sample of the RF samples at a clock cycle of the data clock, the RF sample associated with the location along the scanline defined by the trajectory of the beam through the region of interest;
  b. sending the received RF sample to a first pixel of the set of pixels in a per-data channel image buffer if the flag associated with the received RF sample comprises the first flag indicator value;
  c. discarding the received RF sample if the flag associated with the received RF sample comprises the second flag indicator value; and
  d. processing RF samples corresponding to the first pixel from all of the data channels to generate an image value for the first pixel.

10. The method of claim 9, further comprising amplifying the RF signals.

11. The method of claim 9, further comprising processing the image data to provide processed image data.

12. The method of claim 9, further comprising compressing the flag table.

13. The method of claim 12, further comprising decoding the compressed flag table.

14. The method of claim 9, further comprising processing the RF samples based on the flag table without using an RF buffer to store the RF samples.

15. A system comprising:
a processor; and
one or more non-transitory computer-readable media comprising instructions which, when executed by the processor, are operable to perform operations comprising:
directing a beam of ultrasonic energy at a region of interest, the beam generating ultrasound signals along a scanline defined by a trajectory of the beam through the region of interest;
generating, by a plurality of data channels, radio frequency (RF) signals based on ultrasound signals reflected from portions of the region of interest that lie along the scanline;
digitizing the generated RF signals received from the plurality of data channels to provide RF samples at an RF sampling rate associated with a data clock having a clock cycle, wherein an RF sample of the RF samples is received by each of the plurality of data channels at each clock cycle corresponding to the RF sampling rate, and wherein the RF sample is associated with a location along the scanline defined by the trajectory of the beam through the region of interest;
generating a flag table for the beam and for each data channel, the flag table comprising a flag associated with each of the RF samples, and wherein each flag comprises a first flag indicator value or a second flag indicator value;

generating image data comprising a set of pixels, at least in part by processing each of the RF samples based on the flag table for each of the data channels and for the beam of ultrasonic energy directed at the region of interest, wherein the processing further comprises:
  a. receiving the RF sample of the RF samples at a clock cycle of the data clock, the RF sample associated with the location along the scanline defined by the trajectory of the beam through the region of interest;
  b. sending the received RF sample to a first pixel of the set of pixels in a per-data channel image buffer if the flag associated with the received RF sample comprises the first flag indicator value;
  c. discarding the received RF sample if the flag associated with the received RF sample comprises the second flag indicator value; and
  d. processing RF samples corresponding to the first pixel from all of the data channels to generate an image value for the first pixel.

16. The system of claim 15, wherein the performed operations further comprise amplifying the RF signals.

17. The system of claim 15, wherein the performed operations further comprise processing the image data to provide processed image data.

18. The system of claim 17, further comprising a memory used to process the image data to provide the processed image data, wherein the memory has a size of no more than 2.5 kilobytes (KB) per data channel.

19. The system of claim 15, wherein the performed operations further comprise compressing the flag table.

20. The system of claim 15, wherein the performed operations further comprise decoding the compressed flag table.

21. The system of claim 15, wherein the system comprises one or more field programmable gate array (FPGA) chips or an application-specific integrated circuit (ASIC).

22. The system of claim 21, wherein the one or more FPGA chips or the ASIC comprises an equivalent gate count of no more than about 100,000 gates exclusive of a memory component.

23. The system of claim 15, wherein the RF samples are processed based on the flag table without using an RF buffer to store the RF samples.

* * * * *